(12) United States Patent
Milton et al.

(10) Patent No.: US 9,121,060 B2
(45) Date of Patent: *Sep. 1, 2015

(54) MODIFIED NUCLEOTIDES

(71) Applicant: ILLUMINA CAMBRIDGE LIMITED, Nr. Saffron Walden, Essex (GB)

(72) Inventors: John Milton, Nr. Saffron Walden (GB); Xiaolin Wu, Nr. Saffron Walden (GB); Mark Smith, Nr. Saffron Walden (GB); Joseph Brennan, Nr. Saffron Walden (GB); Colin Barnes, Nr. Saffron Walden (GB); Xiaohai Liu, Nr. Saffron Walden (GB); Silke Ruediger, Nr. Saffron Walden (GB)

(73) Assignee: Illumina Cambridge Limited, Nr. Saffron Walden (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/791,575

(22) Filed: Mar. 8, 2013

(65) Prior Publication Data

US 2013/0197209 A1 Aug. 1, 2013

Related U.S. Application Data

(60) Division of application No. 13/281,275, filed on Oct. 25, 2011, now Pat. No. 8,597,881, which is a division of application No. 12/804,352, filed on Jul. 20, 2010, now Pat. No. 8,071,739, which is a division of (Continued)

(30) Foreign Application Priority Data

Dec. 23, 2002 (GB) .................................. 0230037.4
Feb. 20, 2003 (GB) .................................. 0303924.5

(51) Int. Cl.
*C12Q 1/68* (2006.01)
*C12P 19/34* (2006.01)
(Continued)

(52) U.S. Cl.
CPC ................ *C12Q 1/6869* (2013.01); *C07H 1/00* (2013.01); *C07H 19/06* (2013.01); *C07H 19/10* (2013.01);
(Continued)

(58) Field of Classification Search
CPC ........... C12Q 1/6869; C12Q 2525/113; C12Q 2525/186; C12Q 2563/107
USPC .......................................... 435/6.2, 6.1, 91.1
See application file for complete search history.

(56) References Cited

U.S. PATENT DOCUMENTS 4,711,955 A 12/1987 Ward et al.
4,772,691 A 9/1988 Herman
(Continued)

FOREIGN PATENT DOCUMENTS

DE 4 141 178 6/1993
EP 0 251 786 B1 11/1994
(Continued)

OTHER PUBLICATIONS

Hayakawa et al. Nucleic Acids Research Symposium Series No. 17, 1986 pp. 97-100.*

(Continued)

*Primary Examiner* — Jezia Riley
(74) *Attorney, Agent, or Firm* — Jones day

(57) ABSTRACT

The invention provides modified nucleotide or nucleoside molecule comprising a purine or pyrimidine base and a ribose or deoxyribose sugar moiety having a removable 3'-OH blocking group covalently attached thereto, such that the 3' carbon atom has attached a group of the structure —O—Z wherein Z is any of —C(R')2-O—R", —C(R')2-N(R")2, —C(R')2-N(H)R", —C(R')2-S—R" and —C(R')2-F, wherein each R" is or is part of a removable protecting group; each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group, or a detectable label attached through a linking group; or (R')2 represents an alkylidene group of formula =C(R''')2 wherein each R''' may be the same or different and is selected from the group comprising hydrogen and halogen atoms and alkyl groups; and wherein said molecule may be reacted to yield an intermediate in which each R" is exchanged for H or, where Z is —C(R')2-F, the F is exchanged for OH, SH or NH2, preferably OH, which intermediate dissociates under aqueous conditions to afford a molecule with a free 3'OH; with the proviso that where Z is —C(R')2-S—R", both R' groups are not H.

15 Claims, 7 Drawing Sheets

Related U.S. Application Data application No. 12/455,397, filed on Jun. 1, 2009, now Pat. No. 7,771,973, which is a division of application No. 10/525,401, filed as application No. PCT/GB03/03686 on Aug. 22, 2003, now Pat. No. 7,541,444, which is a continuation-in-part of application No. 10/227,131, filed on Aug. 23, 2002, now Pat. No. 7,057,026.

(51) Int. Cl.
| | | |
|---|---|---|
| C07H 19/06 | (2006.01) | |
| C07H 19/10 | (2006.01) | |
| C07H 19/16 | (2006.01) | |
| C07H 19/20 | (2006.01) | |
| C07H 21/00 | (2006.01) | |
| C07H 1/00 | (2006.01) | |

(52) U.S. Cl.
CPC ............ *C07H 19/16* (2013.01); *C07H 19/20* (2013.01); *C07H 21/00* (2013.01); *C12Q 2525/186* (2013.01); *C12Q 2535/113* (2013.01)

(56) References Cited

U.S. PATENT DOCUMENTS

| | | | |
|---|---|---|---|
| 4,824,775 A | 4/1989 | Dattagupta et al. | |
| 4,863,849 A | 9/1989 | Melamede | |
| 4,888,274 A | 12/1989 | Radding et al. | |
| 5,047,519 A | 9/1991 | Hobbs, Jr. et al. | |
| 5,118,605 A | 6/1992 | Urdea | |
| 5,174,962 A | 12/1992 | Brennan et al. | |
| 5,175,269 A | 12/1992 | Stavrianopoulos | |
| 5,242,796 A | 9/1993 | Prober et al. | |
| 5,302,509 A | 4/1994 | Cheeseman | |
| 5,328,824 A | 7/1994 | Ward et al. | |
| 5,436,143 A | 7/1995 | Hyman | |
| 5,449,767 A | 9/1995 | Ward et al. | |
| 5,476,928 A | 12/1995 | Ward et al. | |
| 5,516,664 A | 5/1996 | Hyman | |
| 5,534,424 A | 7/1996 | Uhlen | |
| 5,547,839 A | 8/1996 | Dower et al. | |
| 5,547,859 A | 8/1996 | Goodman et al. | |
| 5,602,000 A | 2/1997 | Hyman | |
| 5,712,378 A | 1/1998 | Wang | |
| 5,763,594 A | 6/1998 | Hiatt et al. | |
| 5,770,367 A | 6/1998 | Southern et al. | |
| 5,798,210 A | 8/1998 | Canard et al. | |
| 5,808,045 A | 9/1998 | Hiatt et al. | |
| 5,821,356 A | 10/1998 | Khan et al. | |
| 5,849,542 A | 12/1998 | Reeve et al. | |
| 5,872,244 A | 2/1999 | Hiatt et al. | |
| 5,885,775 A | 3/1999 | Haff et al. | |
| 5,959,089 A | 9/1999 | Hannessian | |
| 6,001,566 A | 12/1999 | Canard et al. | |
| 6,008,379 A | 12/1999 | Benson et al. | |
| 6,013,445 A | 1/2000 | Albrecht et al. | |
| 6,046,005 A | 4/2000 | Ju et al. | |
| 6,074,823 A | 6/2000 | Koster | |
| 6,087,095 A | 7/2000 | Rosenthal et al. | |
| 6,136,543 A | 10/2000 | Anazawa et al. | |
| 6,214,987 B1 | 4/2001 | Hiatt et al. | |
| 6,218,118 B1 | 4/2001 | Sampson et al. | |
| 6,218,530 B1 | 4/2001 | Rothschild et al. | |
| 6,232,465 B1 | 5/2001 | Hiatt et al. | |
| 6,242,193 B1 | 6/2001 | Anazawa et al. | |
| 6,255,083 B1 | 7/2001 | Williams | |
| 6,255,475 B1 | 7/2001 | Kwiatkowski | |
| 6,287,821 B1 | 9/2001 | Shi et al. | |
| 6,309,836 B1 | 10/2001 | Kwiatkowski | |
| 6,310,189 B1 | 10/2001 | Fodor et al. | |
| 6,312,893 B1 | 11/2001 | Van Ness et al. | |
| 6,335,155 B1 | 1/2002 | Wells et al. | |
| 6,380,378 B1 | 4/2002 | Kitamura et al. | |
| 6,485,944 B1 | 11/2002 | Church et al. | |
| 6,524,829 B1 | 2/2003 | Seeger | |
| 6,613,508 B1 | 9/2003 | Van Ness et al. | |
| 6,613,523 B2 | 9/2003 | Fischer | |
| 6,639,088 B2 | 10/2003 | Kwiatkowski | |
| 6,664,079 B2 | 12/2003 | Ju et al. | |
| 6,780,591 B2 | 8/2004 | Williams et al. | |
| 6,787,308 B2 | 9/2004 | Balasubramanian et al. | |
| 6,911,345 B2 | 6/2005 | Quake et al. | |
| 6,982,146 B1 | 1/2006 | Schneider et al. | |
| 7,037,654 B2 | 5/2006 | Chenna et al. | |
| 7,037,687 B2 | 5/2006 | Williams et al. | |
| 7,056,666 B2 | 6/2006 | Dower et al. | |
| 7,057,026 B2 | 6/2006 | Barnes et al. | |
| 7,057,031 B2 | 6/2006 | Olejnik et al. | |
| 7,074,597 B2 | 7/2006 | Ju | |
| 7,078,499 B2 | 7/2006 | Odedra et al. | |
| 7,105,300 B2 | 9/2006 | Parce et al. | |
| 7,279,563 B2 | 10/2007 | Kwiathowski | |
| 7,345,159 B2 | 3/2008 | Ju et al. | |
| 7,393,533 B1 | 7/2008 | Crotty et al. | |
| 7,414,116 B2 | 8/2008 | Milton et al. | |
| 7,427,673 B2 | 9/2008 | Balasubramanian et al. | |
| 7,459,275 B2 | 12/2008 | Dower et al. | |
| 7,541,444 B2* | 6/2009 | Milton et al. | 536/4.1 |
| 7,566,537 B2 | 7/2009 | Balasubramanian et al. | |
| 7,592,435 B2 | 9/2009 | Milton et al. | |
| 7,771,973 B2 | 8/2010 | Milton et al. | |
| 7,772,384 B2 | 8/2010 | Balasubramanian et al. | |
| 7,785,790 B1 | 8/2010 | Church et al. | |
| 7,785,796 B2 | 8/2010 | Balasubramanian et al. | |
| 7,795,424 B2 | 9/2010 | Liu et al. | |
| 7,816,503 B2 | 10/2010 | Milton et al. | |
| 8,071,739 B2 | 12/2011 | Milton et al. | |
| 8,084,590 B2 | 12/2011 | Liu et al. | |
| 8,148,064 B2 | 4/2012 | Balasubramanian et al. | |
| 8,158,346 B2 | 4/2012 | Balasubramanian et al. | |
| 8,394,586 B2 | 3/2013 | Balasubramanian et al. | |
| 2003/0008285 A1 | 1/2003 | Fischer | |
| 2003/0104437 A1 | 6/2003 | Barnes et al. | |
| 2003/0186256 A1 | 10/2003 | Fischer | |
| 2004/0014096 A1 | 1/2004 | Anderson et al. | |
| 2004/0039189 A1* | 2/2004 | Guimil et al. | 536/26.1 |
| 2004/0096825 A1 | 5/2004 | Chenna et al. | |
| 2006/0160081 A1 | 7/2006 | Milton et al. | |
| 2006/0188901 A1 | 8/2006 | Barnes et al. | |
| 2007/0166705 A1 | 7/2007 | Milton et al. | |
| 2010/0159531 A1 | 6/2010 | Gordon et al. | |
| 2010/0292452 A1 | 11/2010 | Milton et al. | |
| 2010/0317531 A1 | 12/2010 | Balasubramanian et al. | |
| 2010/0323350 A1 | 12/2010 | Gordon | |
| 2011/0020827 A1 | 1/2011 | Milton et al. | |
| 2011/0124054 A1 | 5/2011 | Olejnik et al. | |
| 2011/0183327 A1 | 7/2011 | Balasubramanian et al. | |
| 2012/0052489 A1 | 3/2012 | Gordon et al. | |
| 2012/0095201 A1 | 4/2012 | Milton et al. | |
| 2012/0156671 A1 | 6/2012 | Liu et al. | |
| 2012/0202196 A1 | 8/2012 | Balasubramanian et al. | |
| 2012/0252010 A1 | 10/2012 | Balasubramanian et al. | |

FOREIGN PATENT DOCUMENTS

| | | |
|---|---|---|
| EP | 0 992 511 | 4/2000 |
| EP | 1 182 267 | 2/2002 |
| EP | 1 291 354 | 3/2003 |
| EP | 0 808 320 | 4/2003 |
| EP | 2325304 | 9/2004 |
| EP | 1 730 307 | 12/2006 |
| EP | 1 337 541 | 3/2007 |
| EP | 1 218 391 | 4/2007 |
| EP | 1 790 736 | 5/2007 |
| EP | 1 560 838 | 5/2009 |
| EP | 2 119 722 | 11/2009 |
| EP | 2 338 893 | 6/2011 |
| WO | WO 89/09282 | 10/1989 |
| WO | WO89/10977 | 11/1989 |
| WO | WO 90/13666 | 11/1990 |
| WO | WO 91/06678 | 5/1991 |
| WO | WO 92/10587 | 6/1992 |
| WO | WO 93/05183 | 3/1993 |

(56) References Cited

FOREIGN PATENT DOCUMENTS

| WO | WO 93/21340 | 10/1993 |
|---|---|---|
| WO | WO 94/14972 | 7/1994 |
| WO | WO 96/07669 | 3/1996 |
| WO | WO 96/11937 | 4/1996 |
| WO | WO 96/23807 | 8/1996 |
| WO | WO 96/27025 | 9/1996 |
| WO | WO 98/30720 | 7/1998 |
| WO | WO 98/33939 | 8/1998 |
| WO | WO 99/05315 | 2/1999 |
| WO | WO99/49082 | 9/1999 |
| WO | WO 99/57321 | 11/1999 |
| WO | WO 00/02895 | 1/2000 |
| WO | WO 00/06770 | 2/2000 |
| WO | WO 00/15844 | 3/2000 |
| WO | WO 00/18956 | 4/2000 |
| WO | WO 00/21974 | 4/2000 |
| WO | WO 00/50642 | 8/2000 |
| WO | WO 00/53805 | 9/2000 |
| WO | WO 00/53812 | 9/2000 |
| WO | WO 00/70073 | 11/2000 |
| WO | WO 01/16375 | 3/2001 |
| WO | WO 01/23610 | 4/2001 |
| WO | WO 01/25247 | 4/2001 |
| WO | WO 01/32930 | 5/2001 |
| WO | WO 01/57248 | 8/2001 |
| WO | WO 01/57249 | 8/2001 |
| WO | WO 01/92284 | 12/2001 |
| WO | WO 02/02813 | 1/2002 |
| WO | WO 02/22883 | 3/2002 |
| WO | WO 02/29003 | 4/2002 |
| WO | WO 02/072892 | 9/2002 |
| WO | WO 02/079519 | 10/2002 |
| WO | WO 02/088381 | 11/2002 |
| WO | WO 02/088382 | 11/2002 |
| WO | WO 03/002767 | 1/2003 |
| WO | WO 03/020968 | 3/2003 |
| WO | WO 03/048178 | 6/2003 |
| WO | WO 03/048387 | 6/2003 |
| WO | WO 03/085135 | 10/2003 |
| WO | WO 2004/007773 | 1/2004 |
| WO | WO 2004/018493 | 3/2004 |
| WO | WO 2004/018497 | 3/2004 |
| WO | WO 2005/084367 | 9/2005 |

OTHER PUBLICATIONS

"Pierce Chemical Company", Products Catalog, 1999/2000.
Burns, et al., "Selective Reduction of Disulfides by Tris(2-carboxyethyl)phosphine", J. Org. Chem 56, 1991, 2648-2650.
Dawson, et al. "Affinity Isolation of Transcriptionally Active Murine Erythroleukemia Cell DNA Using a Cleavable Biotinylated Nucleotide Analog", The Journal of Biological Chemistry; vol. 264, No. 22, 1989, 12830-12837.
Handlon, et al., "Thiol Reduction of 3'-Azidothymidine to 3'-Aminothymidine: Kinetics and Biomedical Implications", Pharm. Res., 5, 1988, 297-99.
IPR2013-00128, "Proposed Protective Order in the Trustees of Columbia University in the City of New York v. Illumina, Inc.", Dec. 12, 2012.
IPR2013-00128, "Excerpts from the file history of European Patent Application No. 02781434.2", Aug. 16, 2006.
IPR2013-00128, "Illumina Notice of Cross-Examination Deposition of IBS Declarant Dr. Bruce P. Branchaud", Jan. 31, 2014.
IPR2013-00128, "Intelligent Bio-System, Inc.'s Current Exhibit List", Jan. 24, 2014.
IPR2013-00128, "Order Conduct of the Proceeding", Jan. 31, 2014.
IPR2013-00128, "Patent Owner's Unopposed Motion to File Substitute Declarations of Eric Vermaas and Floyd Romesberg, Ph.D., and to File Substitute Motion to Amend", Jan. 31, 2014.
IPR2013-00128, "Petitioner Intelligent Bio-Systems, Inc.'s Motion to Seal", Jan. 24, 2014.
IPR2013-00128, "Petitioner Intelligent Bio-Systems, Inc.'s Opposition to Illumina's Motion to Amend", Jan. 24, 2014.
IPR2013-00128, "Second Declaration of Dr. Bruce Branchaud in Support of Intelligent Bio-Systems, Inc.'s Opposition to Illumina's Motion to Amend", Jan. 24, 2014.
IPR2013-00128, "Substitute Declaration of Floyd Romesberg, Ph.D., in Support of Patent Owner's Motion to Amend", Jan. 24, 2014.
IPR2013-00128, "Transcript of Video Deposition of Floyd Romesberg, Ph.D.", Jan. 24, 2014.
IPR2013-00128, "Trascript of Video Deposition of Eric Vermaas", Jan. 14, 2014.
Klausner, et al., "Dupont's DNA Sequencer Uses New Chemistry", Nature Publishing Group, Bio/technology; vol. 5, Nov. 1987, 1-2.
Letsinger, et al., "2,4-Dinitrobenzenesulfenyl as a Blocking Group for Hydroxyl Functions in Nucleosides", J. Org. Chem. 29, 1964, 2615-2618.
Lukesh, et al., "A Potent, Versatile Disulfide-Reducing Agent from Aspartic Acid", Jounal of the American Chemical Society; 134, 2012, 4057-4059.
Mitra, et al., "Fluorescent in situ sequencing on polymerase colonies", Analytical Biochemistry, Academic Press, San Diego US, vol. 320 No. 1, 2002, 55-65.
Murakami, et al., "Structure of a *Plasmodium yoelii* gene-encoded protein homologiys to the Ca2+-ATPase of rabbit skeletal muscle sarcoplasmic reticulum", J. Cell Sci. 97, 1990, 487-95.
Petition for Inter Partes Review of U.S. Patent No. 7,057,026 (IPR2013-00324), dated Jun. 4, 2013.
Petition for Inter Partes Review of U.S. Patent No. 7,566,537 (IRP2013-00517), dated Aug. 19, 2013.
Petition for Inter Partes Review of U.S. Patent No. 7,566,537 (IPR2013-00518), dated Aug. 19, 2013.
Excerpts from the Deposition transcript of Dr. Xiaohai Liu, taken Mar. 20, 2013.
Excerpts from the file history of European Patent Application No. 02781434.2, 2009.
Executed Declaration of Dr. Bruce P. Branchaud in Support of Petition for *Inter Partes* Review of U.S. Patent No. 7,057,026 (IPR2013-00128), executed on Jan. 28, 2013.
Executed Declaration of Dr. Bruce P. Branchaud in Support of Petition for *Inter Partes* Review of U.S. Patent No. 8,158,346 (IPR2013-00266), executed on May 3, 2013.
Executed Declaration of Dr. Bruce P. Branchaud in Support of Petition for *Inter Partes* Review of U.S. Patent No. 7,056,026 (IPR2013-00324), executed on Jun. 4, 2013.
Executed Declaration of Dr. Bruce P. Branchaud in Support of Petition for *Inter Partes* Review of U.S. Patent No. 7,566,537 (IPR2013-00517), executed on Aug. 16, 2013.
Executed Declaration of Dr. Bruce P. Branchaud in Support of Petition for *Inter Partes* Review of U.S. Patent No. 7,566,537 (IPR2013-00518), executed on Aug. 16, 2013.
Greene, et al., "Protective Groups in Organic Synthesis," John Wiley & Sons, New York, pp. 1-5, 17-27, 30-33, 67-74, 96-99, 190-191, 260-261, 542-543, 701-719, 749-779 (1999).
Loubinoux et al., "Protection of Phenols by the Azidomethylene Group Application to the Synthesis of Unstable Phenols," *Tetrahedron*, 44(19):6055-6064 (1988).
Matsumoto et al., "A Revised Structure of Pederin," *Tetrahedron*, 60:6297-6300 (1968).
Meinwald, "An Approach to the Synthesis of Pederin," *Pure and Appl. Chem.*, 49:1275-1290 (1977).
U.S. Appl. No. 09/684,670, filed Oct. 6, 2000.
Definitions of "VIZ", The Oxford English Dictionary 1989; The Chambers Dictionary 1993; The Longman Dictionary of Contemporary English 2009.
Definition of "VIZ", "Merriam-Webster's Collegiate Dictionary", 10th edition, 1997, 1316.
"Getting published in Nature: the editorial process", Wayback Machine, 2008.
Office Action mailed Dec. 14, 2012 in U.S. Appl. No. 13/437,772.
Bebenek, et al., "Frameshift errors initiated by nucleotide misincorporation", Proc. Natl. Acad. Sci. USA, vol. 87, Jul. 1990, 4946-4950.

(56) References Cited

OTHER PUBLICATIONS

Bebenek, et al., "The Effects of dNTP Pool Imbalances on Frameshift Fidelity during DNA Replication", The Journal of Biological Chemistry, vol. 267, No. 6, Issue of Feb. 25, 1992, 3589-3596.
Bentley, et al., "Accurate whole human genome sequencing using reversible terminator chemistry", Nature, vol. 456, No. 7218, Nov. 6, 2008, 53-59.
Bi, et al., "Design and Synthesis of a Chemically Cleavable Fluorescent Nucleotide, 3'-O-Allyl-dGTP-allyl-Bodipy-FL-510, as a Reversible Terminator for DNA Sequencing by Synthesis", J. Am. chem. Soc., 128, dated Oct. 20, 2005, 2542-2543.
Brown, et al., "Modern machine-aided methods of oligodeoxyribonucleotide synthesis", Oligonucleotides and Analogues, A Practical Approach, 1991, i-ii, 1-11, 255.
C.A. No. 12-376 (GMS), "Videotaped Deposition of Dr Xiaohai Liu", dated Mar. 20, 2013.
Canard, Bruno et al., "DNA polymerase fluorescent substrates with reviersible 3'-tags", Gene. 148, 1994, 1-6.
Christensen, et al., "Specific Chemical Synthesis of Ribonucleoside 0-Benzyl Ethers", J. Org. Chem. vol. 37, No. 22, 1972, 3398-3401.
Dantas, et al., "Stannous chloride mediates single strand breaks in plasmid DNA through reactive oxygen species formation", Toxicology Letters 110, 1999, 129-136.
Fersht, et al., "DNA polymerase accuracy and spontaneous mutation rates: Frequencies of purinepurine, purinepyrimidine, and pyrimidine pyrimidine mismatches during DNA replication", Proc. Natl. Acad. Sci. USA, vol. 78, No. 7, Jul. 1981, 4251-4255.
Fersht, et al., "Fidelity of replication of phage OX174 DNA by DNA polymerase III holoenzyme: Spontaneous mutation by misincorporation", Proc. Natl. Acad. Sci. USA, vol. 76, No. 10, Oct. 1979, 4946-4950.
For Authors, "Getting published in Nature: the editorial process", nature.com, 2014.
Guo, "Molecular Engineering of Novel Nucleotide Analogues for DNA Sequencing and Analysis", Columbia University, 2009.
Guo, J. et al., "Four-color DNA sequencing with 3'-0-modified nucleotide reversible terminators and chemically cleavable fluorescent dideoxynucleotides", PNAS, 105(27), 2008, 9145-9150.
Holtzman, et al., "Electron microscopy of complexes of isolated acetylcholine receptor, biotinyl-toxin, and avidin", Proc. Natl. Acad. Sci. USA, vol. 79, Jan. 1982, 310-314.
IPR2013-00128, "Branchaud Second Depo Transcript", Dated Feb. 11, 2014.
IPR2013-00128, "Branchaud Signature page and Errata for Feb. 11, 2014 Deposition Transcript", dated Mar. 21, 2014.
IPR2013-00128,"Decision", dated Jul. 29, 2013.
IPR2013-00128, "Decision Patent Owner's Motion to File Substitute Declarations and Substitute Motion to Amend", dated Feb. 19, 2014.
IPR2013-00128,"Declaration of Adrienne Stephens", dated Mar. 17, 2014.
IPR2013-00128, File history excerpts from U.S. Appl. No. 10/285,010, dated Feb. 24, 2014.
IPR2013-00128, "Illumina Appendix of Authority for Its Opposition to IBS Motion to Exclude Evidence", dated Mar. 31, 2014.
IPR2013-00128, "Illumina Appendix of Authority for Its Reply to IBS Opposition to Illumina Motion to Exclude Evidence", dated Apr. 7, 2014.
IPR2013-00128, "Illumina Demonstratives for Oral Argument", dated Apr. 21, 2014.
IPR2013-00128, "Illumina Notice of Filing Its Demonstratives for Oral Hearing", dated Apr. 21, 2014.
IPR2013-00128, "Illumina Reply to IBS Opposition to Motion to Exclude", dated Apr. 7, 2014.
IPR2013-00128, "Illumina Updated Exhibit List", dated Apr. 21, 2014.
IPR2013-00128, "Illumina Updated Exhibit List", dated Feb. 19, 2014.
IPR2013-00128, "Illumina Updated Exhibit List", dated Feb. 24, 2014.
IPR2013-00128, "Illumina Updated Exhibit List", dated Mar. 18, 2014.
IPR2013-00128, "Illumina's Motion to Exclude IBS Evidence", dated Mar. 18, 2014.
IPR2013-00128, "Illumina's Request for Oral Argument", dated Mar. 18, 2014.
IPR2013-00128, "Illumina's Substitute Motion to Amend Under 37 C.F.R. § 42.121", dated Feb. 19, 2014.
IPR2013-00128, "Intelligent Bio-System, Inc.'s Current Exhibit List Under 37 C.F.R. § 42.63", dated Mar. 18, 2014.
IPR2013-00128,"Intelligent Bio-System, Inc.'s Current Exhibit List Under 37 C.F.R. § 42.63", dated Mar. 31, 2014.
IPR2013-00128, "Intelligent Bio-System, Inc.'s Current Exhibit List", dated Apr. 16, 2014.
IPR2013-00128, "Intelligent Bio-System, Inc.'s Current Exhibit List Under 37 C.F.R. § 42.63", dated Apr. 16, 2014.
IPR2013-00128, "Intelligent Bio-System, Inc.'s Current Exhibit List Under 37 C.F.R. § 42.63", dated Jan. 24, 2014.
IPR2013-00128, "Intelligent Bio-System's Objections to Illumina's Exhibits Submitted With Its Reply to Petitioner's Opposition to Illumina's Motion to Amend", dated Mar. 3, 2014.
IPR2013-00128, "Intelligent Bio-Systems, Inc.'s Opposition to Illumina's Motion to Exclude IBS Evidence", dated Mar. 31, 2014.
IPR2013-00128,"Intelligent Bio-Systems, Inc.'s Demonstratives for Apr. 23, 2014 Oral Argument", dated Apr. 16, 2014.
IPR2013-00128,"Inter Partes Review—Petitioner Power of Attorney", dated Apr. 15, 2014.
IPR2013-00128,"Order Conduct of the Proceeding", dated Apr. 11, 2014.
IPR2013-00128, "Order Trial Hearing", dated Mar. 31, 2014.
IPR2013-00128, "Patent Owner Illumina's Reply to Petitioner's Opposition to Illumina's Motion to Amend", dated Feb. 24, 2014.
IPR2013-00128, "Petitioner Intelligent Bio-Systems, Inc.'s Motion to Exclude Evidence", dated Mar. 18, 2014.
IPR2013-00128, "Petitioner Intelligent Bio-Systems, Inc.'s Reply to Illumina's Opposition to Intelligent Bio-Systems, Inc.'s Motion to Exclude Evidence", dated Apr. 7, 2014.
IPR2013-00128,"Petitioner Intelligent Bio-Systems, Inc.'s Request for Oral Argument", dated Mar. 18, 2014.
IPR2013-00128, "Petitioner Intelligent Bio-Systems, Inc.'s Supplemental Mandatory Notice: Additional Backup Counsel", dated Apr. 4, 2014.
IPR2013-00128, "Power of Attorney and Certificate of Service", dated Apr. 4, 2014.
IPR2013-00128, "Redlined Version—Illumina Motion to Amend", dated Feb. 19, 2014.
IPR2013-00128, "Redlined Version—Redacted Vermaas Declaration", dated Feb. 19, 2014.
IPR2013-00128, "Redlined Version—Romesberg Declaration", dated Feb. 19, 2014.
IPR2013-00128, "Romesberg signature page and errata for Jan. 14, 2014 depo transcriipt", dated Feb. 23, 2014.
IPR2013-00128,"ScanArray Express Brochure", 2002, 11 pages.
IPR2013-00128, "Second Declaration of Dr. Bruce Branchaud in Support of Intelligent Bio-Systems, Inc.'s Opposition to Illumina's Motion to Amend", dated Jan. 24, 2014.
IPR2013-00128, "Substitute Declaration of Eric Vermaas Accompanying Patent Owner's Motion to Amend—Redacted", dated Jan. 24, 2014.
IPR2013-00128, "Substitute Declaration of Floyd Romesberg, Ph.D., in Support of Patent Owner's Motion to Amend", dated Feb. 19, 2014.
IPR2013-00128, "Substitute Declaratton of Erjc Vermaas Accompanying Patent Owner's Motion to Amend", dated Feb. 19, 2014.
IPR2013-00128, "Supplemental Information for Exhibit 1032", dated Jan. 27, 2014.
IPR2013-00128, "Vermaas signature page and errata for Jan. 13, 2014 depo transcript", dated Feb. 19, 2014.
IPR2013-00266, "Branchaud Deposition Transcript", dated Mar. 11, 2014.
IPR2013-00266, "Demonstrative Exhibits of Intelligent Bio-Systems, Inc. for Oral Hearing", dated May 28, 2014.

(56) References Cited

OTHER PUBLICATIONS

IPR2013-00266, "Errata Sheet for Bruce Branchaud, Ph.D. Deposition Taken: March 11, 2014", dated May 16, 2014.
IPR2013-00266, "Excerpts from Branchaud Deposition Transcript in related IPR2013-00128", dated Oct. 3, 2013.
IPR2013-00266, "Illumina Appendix of Authority", dated May 2, 2014.
IPR2013-00266, "Illumina Motion to Exclude IBS Evidence", dated Apr. 18, 2014.
IPR2013-00266, "Illumina Notice of Cross-Examination Deposition of IBS Declarant Dr. Bruce Branchaud", dated Mar. 4, 2013.
IPR2013-00266, "Illumina Objections to the Admissibility of IBS Evidence Served on Feb. 28, 2014", dated Mar. 7, 2014.
IPR2013-00266, "Illumina Opposition to IBS Motion to Exclude Illumina Evidence", dated May 2, 2014.
IPR2013-00266, "Illumina Reply to IBS Opposition to Motion to Exclude", dated May 9, 2014.
IPR2013-00266, "Illumina Request for Oral Argument", dated Apr. 18, 2014.
IPR2013-00266, "Illumina Response to IBS Mot. for Observations on Romesberg Testimony", dated May 2, 2014.
IPR2013-00266, "Illumina Updated Exhibit List", dated Apr. 18, 2014.
IPR2013-00266, "Illumina Updated Exhibit List", dated Mar. 21, 2014.
IPR2013-00266, "Illumina's Notice of Filing Its Demonstratives (Exhibit 2060) for May 28, 2014 Oral Argument", dated May 22, 2014.
IPR2013-00266, "Illumina'S Third Supplemental Mandatory Notice Re Backup Counsel—37 C.F.R. § 42.8 (a)(3)", dated May 21, 2014.
IPR2013-00266, "Illumina's Additional Power of Attorney", dated May 22, 2014.
IPR2013-00266, "Illumina's Demonstratives for Oral Agument", dated May 28, 2014.
IPR2013-00266,"Illumina's Updated Exhibit List", dated May 22, 2014.
IPR2013-00266, "Intelligent Bio-System, Inc.'s Current Exhibit List Under 37 C.F.R. § 42.63", dated May, 2 2014.
IPR2013-00266, "Intelligent Bio-System, Inc.'s Current Exhibit List Under 37 C.F.R. § 42.63", dated May 22, 2014.
IPR2013-00266, "Intelligent Bio-System, Inc.'s Current Exhibit List Under 37 C.F.R. § 42.63", dated Apr. 18, 2014.
IPR2013-00266, "Intelligent Bio-System, Inc.'s Current Exhibit List Under 37 C.F.R. § 42.63", dated Feb. 28, 2014.
IPR2013-00266, "Intelligent Bio-System, Inc.'s Current Exhibit List Under 37 C.F.R. § 42.63", dated May 16, 2014.
IPR2013-00266, "Intelligent Bio-System, Inc.'s Notice of Filing Its Demonstratives (Ex. 1045) for May 28, 2014 Oral Argument", dated May 22, 2014.
IPR2013-00266, "Intelligent Bio-System's Objections to Illumina's Exhibits Submitted With Its Reply to Petitioner's Opposition to Illumina's Motion to Amend", dated Mar. 28, 2014.
IPR2013-00266, "Intelligent Bio-Systems, Inc.'s Opposition to Illumina's Motion to Exclude IBS Evidence", dated May 2, 2014.
IPR2013-00266, "Intelligent Bio-Systems' Notice of Cross-Examination Deposition of Illumina's Declarant Dr. Floyd Romesberg", dated Apr. 3, 2014.
IPR2013-00266, "Inter Partes Review—Petitioner Power of Attorney", dated Apr. 4, 2014.
IPR2013-00266, "Order Revised Scheduling Order 37 C.F.R. § 42.5", dated Apr. 4, 2014.
IPR2013-00266, "Order Trial Hearing", Apr. 29, 2014.
IPR2013-00266, "Patent Owner Illumina's Reply to Petitioner's Opposition to Illumina's Motion to Amend", dated Mar. 21, 2014.
IPR2013-00266, "Petitioner Intelligent Bio-Systems, Inc.'s Motion for Observations on the Cross-Examination Testimony of Floyd Romesberg, Ph.D.", dated Apr. 18, 2014.
IPR2013-00266, "Petitioner Intelligent Bio-Systems, Inc.'s Motion to Exclude Evidence", dated Apr. 18, 2014.
IPR2013-00266, "Petitioner Intelligent Bio-Systems, Inc.'s Motion to Seal Under 37 C.F.R. § 42.54", dated Feb. 28, 2014.
IPR2013-00266, "Petitioner Intelligent Bio-Systems, Inc.'s Opposition to Illumina's Motion to Amend", dated Feb. 28, 2014.
IPR2013-00266, "Petitioner Intelligent Bio-Systems, Inc.'s Request for Oral Argument", dated Apr. 18, 2014.
IPR2013-00266, "Petitioner Intelligent Bio-Systems, Inc.'s Supplemental Mandatory Notice: Additional Backup Counsel", dated Apr. 4, 2014.
IPR2013-00266,"Proposed Protective Order", dated Dec. 21, 2012.
IPR2013-00266,"Romesberg Errata and Signature Page", dated Apr. 10, 2014.
IPR2013-00266, "Second Declaration of Bruce Branchaud in related IPR2013-00128", dated Jan. 24, 2014.
IPR2013-00266, "Second Declaration of Dr. Bruce Branchaud in Support of Intelligent Bio-Systems, Inc.'s Opposition to Illumina's Motion to Amend", dated Feb. 28, 2014.
IPR2013-00266, "Second Declaration of Floyd Romesberg, Ph.D.", dated Mar. 21, 2014.
IPR2013-00266, "Second Declaration of Jason P. Grier", dated Mar. 21, 2014.
IPR2013-00266, "Video Deposition of Eric Vermaas in IPR2013-00128", dated Jan. 13, 2014.
IPR2013-00266, "Video Deposition of Floyd Romesberg, Ph.D.", dated Apr. 10, 2014.
IPR2013-00266, "Video Deposition of Floyd Romesberg, Ph.D. in IPR2013-00128", dated Jan. 14, 2014.
IPR2013-00517, "[Proposed] Protective Order", dated Dec. 21, 2012.
IPR2013-00517, "Curriculum Vitae Dr. Kevin Burgess", dated May 5, 2014.
IPR2013-00517, "Decision—Institution of Inter Partes Review—37 CFR 42.108", dated Feb. 13, 2014.
IPR2013-00517, "Declaration of Floyd Romesberg, Ph.D.", dated May 5, 2014.
IPR2013-00517, "Declaration of Kevin Burgess, Ph.D.", dated May 5, 2014.
IPR2013-00517, "Declaration of Rosalyn M. Espejo Regarding Fed. R. Evid. 902(11) Certification of Records", dated May 5, 2014.
IPR2013-00517, "Declaration of William R. Zimmerman in Support of Motion to Appear Pro Hac Vice on Behalf of Patent Owner Illumina Cambridge Ltd.", dated Feb. 13, 2014.
IPR2013-00517, "Facile Conversion of Adenosine Into New 2'-Substitlited-2'-Deoxy-Arabinofijrarosyladenine Derivatives: Stereospecific Syntheses of 2'-Azido-2'-Deoxy-,2'-Amino-Z'-Deoxy-, and Z'-Mercapto-Z'-Deoxy-O-D-Arabinofuranosilade", Tetrahedron Letters No. 45, 1978, 4341-4344.
IPR2013-00517, "Illumina Additional Power of Attorney", dated May 5, 2014.
IPR2013-00517, "Illumina Exhibit List", dated Mar. 13, 2014.
IPR2013-00517, "Illumina Motion to Seal Under 37 C.F.R. § 42.54", dated May 5, 2014.
IPR2013-00517, "Illumina Notice of Cross-Examination Deposition of IBS Declarant Dr. Bruce P. Branchaud", dated Mar. 25, 2014.
IPR2013-00517, "Illumina Updated Exhibit List", dated May 5, 2014.
IPR2013-00517, "Illumina Updated Mandatory Notice Regarding Designated Counsel", dated May 5, 2014.
IPR2013-00517, "Intelligent Bio-Systems Inc.'s List of Proposed Motions", dated Feb. 27, 2014.
IPR2013-00517, "Motion for William R. Zimmerman to AppearPro Hac Vice on Behalf of Patent Owner Illumina Cambridge Ltd.", dated Mar. 13, 2014.
IPR2013-00517, Notice of Allowance in U.S. Appl. No. 11/301,578, dated Apr. 30, 2009.
IPR2013-00517, "Notice of Stip to Change Due Dates 1 and 2", dated Apr. 7, 2014.
IPR2013-00517, "Order—Conduct of the Proceedings", dated Mar. 6, 2014.
IPR2013-00517, "Order Conduct of the Proceedings 37 .F.R. § 42.5", dated May 6, 2014.
IPR2013-00517, "Order Conduct of the Proceedings 37 .F.R. § 42.5", dated May 7, 2014.

(56) References Cited

OTHER PUBLICATIONS

IPR2013-00517, "Order—Patent Owner's Motion for William R. Zimmerman to Appear Pro Hac Vice", dated Apr. 2, 2014.
IPR2013-00517, "Patent Owner Illumina's Proposed Motions", dated Feb. 27, 2014.
IPR2013-00517, "Petitioner Intelligent Bio-Systems, Inc.'s Supplemental Mandatory Notice: Additional Backup Counsel", dated Apr. 4, 2014.
IPR2013-00517, "Press Release—Illumina to acquire Solexa", dated 2006.
IPR2013-00517, "Qiagen's Dietrich Hauffe on Bringing Next-Generation Sequencing to clinical Research and Molecular Dx", Interview; http://www.genomeweb.com/print/1254496, dated Jul. 7, 2013.
IPR2013-00517,Response to Office Action in U.S. Appl. No. 13/305,415, dated Aug. 14, 2013.
IPR2013-00517, "Scheduling Order", dated Feb. 13, 2014.
IPR2013-00517, "Transcript of Videotaped Deposition of Bruce Branchaud, Ph.D. in IPR-2013-00128", dated Oct. 3, 2013.
IPR2013-00517, "Transcript of Videotaped Deposition of Bruce P. Branchaud in IPR-2013-000128", dated Feb. 11, 2014.
IPR2013-00517, "Transcript of Videotaped Deposition of Bruce P. Branchaud in IPR2013-00266", dated Mar. 11, 2014.
IPR2013-00517,"Videotaped Deposition of: Bruce P. Branchaud, Ph.D.", dated Apr. 8, 2014.
IPR2013-00517, "Yu, Sequencing by Synthesis with Cleavable Fluorescent Nucleotide Reversible Terminators (C-F-NRTs)", dated Oct. 20, 2008.
IPR2013-00518, "Decision—Institution of Inter Partes Review—37 CFR 42.108", dated Feb. 13, 2014.
IPR2013-00518, "Declaration of William R. Zimmerman in Support of Motion to Appear Pro Hac Vice on Behalf of Patent Owner Illumina Cambridge Ltd.", dated Mar. 11, 2014.
IPR2013-00518, "Illumina Exhibit List", dated Feb. 13, 2014.
IPR2013-00518, "Illumina Notice of Cross-Examination Deposition of IBS Declarant Dr. Bruce P. Branchaud", dated Mar. 25, 2014.
IPR2013-00518, "Illumina Request for Adverse Judgment Under 37 CFR § 42.73(b)(2)", dated May 5, 2014.
IPR2013-00518, "Intelligent Bio-Systems Inc.'s List of Proposed Motions", dated Feb. 27, 2014.
IPR2013-00518,"Inter Partes Review—Petitioner Power of Attorney", dated Apr. 4, 2014.
IPR2013-00518, "Judgment Request for Adverse Judgment 37 C.F.R. § 42.73(b)", dated May 6, 2014.
IPR2013-00518, "Motion for William R. Zimmerman to Appear Pro Hac Vice on Behalf of Patent Owner Illumina Cambridge Ltd.", dated Mar. 13, 2014.
IPR2013-00518, "Notice of Stipulation to Change Due Dates 1 and 2", dated Apr. 7, 2014.
IPR2013-00518, "Order—Conduct of the Proceedings", dated Mar. 6, 2014.
IPR2013-00518, "Order—Patent Owner's Motion for William R. Zimmerman to Appear Pro Hac Vice", dated Apr. 2, 2014.
IPR2013-00518, "Patent Owner Illumina's Proposed Motions", dated Feb. 27, 2014.
IPR2013-00518, "Petitioner Intelligent Bio-Systems, Inc.'s Supplemental Mandatory Notice: Additional Backup Counsel", dated Apr. 4, 2014.
IPR2013-00518, "Scheduling Order", dated Feb. 13, 2014.
IPR2013-00518, "Substitute Declaration of Floyd Romesberg, Ph.D., in Support of Patent Owner's Motion to Amend", dated Jan. 24, 2014.
Iye, et al., "Nucleoside Oxazaphospholidines as Novel Synthons in Oligonucleotide Synthesis", J. Org. Chem, 60, 1995, 5388-5389.
Ju, et al., "Four-color DNA sequencing by synthesis using cleavable fluorescent nucleotide reversible terminators", PNAS; vol. 103; No. 52, dated Dec. 26, 2006.
Ju, et al., "Four-color DNA sequencing by synthesis using cleavable fluorescent nucleotide reversible terminators", Columbia Genome Center, Columbia University College of Physicians and Surgeons; Department of chemical Engineering and Biomedical Engineering, Oct. 26, 2006, 19635-19640.
Jung, et al., "Conversion of Alky Carbamates into Amines via Treatment With Trimethylsilyl Iodide", Chem. Comm. (7), 1978, 315-316.
Kim, Dae H., "Four-Color DNA Sequencing by Synthesis on a Chip Using Cleavable Fluorescent Nucleotide Reversible Terminators", Columbia University, 2008.
Kit, Saul, "Deoxyribonucleic Acids", Division of Biochemical Virology, Baylor University College of Medicine, Houston Texas, Annu. Rev. Biochem, 1963, 43-82.
Lee, et al., "Unwinding of double-stranded DNA helix y dehydration", Proc. Natl. Acad. Sci. USA, vol. 78, No. 5, May 1981, 2838-2842.
Mardis, Elaine R., "A decade's perspective on DNA sequencing technology", Nature; vol. 470, Perspective; doi:10.1038/nature09796, Feb. 10, 2011, 198-203.
Meng, et al., "Design and Synthesis of a Photocleavable Fluorescent Nucleotide 3'-O-Allyl-dGTP-PC-Bodipy-FL-510 as a Reversible Terminator for DNA Sequencing by Synthesis", JOC; 71, 2006, 3248-3252.
Meng, Qinglin, "PartI. Tandem Aldol-Allylation Reactions Promoted by Strained Silacycles", PartII. Design and Synthesis of Modified Fluorescent Nucleotides for DNA Sequencing by Synthesis, ColumbiaUniversity, 2006.
Mitra, et al., "Supplementary Information for Fluorescent in situ Sequencing on Polymerase Colonies", Analytical Biochemistry, 2003, 1-19.
Mullis, K.B. et al., "Specific Synthesis of DNA in Vitro via a Polymerase-Catalyzed Chain Reaction", Methods in Enzymology, vol. 155, Recmbinant DNA, part F, 1987, 19 pages.
Mungall, et al., "Use of the Azido Group in the Synthesis of 5' Terminal Aminodeoxythymidine Oligonucleotides", J. Org. Chem., vol. 40, No. 11, 1975.
O'Neil, et al., "The Merk Index", An Encyclopedia of Chemicals, Drugs, and Biologicals, Thirteenth Edition, 2001, 9815.
Pilard, et al., "A stereospecific synthesis of (±) α-conhydrine and (±)β-conhydrine.", Tetrahedron Letters, vol. 25, No. 15, 1984, 1555-1556.
Pugliese, et al., "Three-dimensional Structure of the Tetragonal Crystal Form of Egg-white Avidin in its Functional Complex with Biotin at 2 7 A Resolution", J. Mol. Biol., 1993, 698-710.
Qui, Chunmei, "Novel Molecular Engineering Approaches for Genotyping and DNA Sequencing", Columbia University, 2011.
Rigas, et al., "Rapid plasmid library screening using RecA-coated biotinylated probes", Proc. Natl. Acad. Sci. USA vol. 83, Genetics, Dec. 1986, 9591-9595.
Ruparel, et al., "Design and synthesis of a 3-O-allyl photocleavable fluorescent nucleotide as a reversible terminator for DNA sequencing by synthesis", PNAS, vol. 102, No. 17, dated Apr. 26, 2005, 5932-5937.
Shen, et al., "RNA structure at high resolution", The FASEB Journal, vol. 9, Aug. 1995, 1023-1033.
Shendure, et al., "Advanced sequencing technologies: methods and goals", Nature Rev. Genet., 5, 2004, 335-344.
Taylor, et al., "Rise per base pair in helices of double-stranded rotavirus RNA determined by electron microscopy", Virus Research, 2, 1985, 175-182.
Tietze, et al., "Synthesis of a Novel Stable GM.-Lactone Analogue as Hapten for a Possible Immunization Against Cancer", Angew. Chem. Int. Ed. Engl. 36, No. 15, 1997, 1615-1617.
Watkins, et al., "Synthesis of Oligodeoxyribonucleotides Using N-Benzyloxycarbonyl-Blocked Nucleosides", J. Am. Chem. Soc. 104, 1982, 5702-5708.
Watson, et al., "Molecular Biology of the Gene; 5th edition", The Structures of DNA and RNA; Chapter 6, 2004, 97-128.
Welch, et al., "Syntheses of Nucleosides Designed for Combinatorial DNA Sequencing", Chem. Eur. J., 5, 1999, 951-960.
Westheimer, F.H., "Why Nature Chose Phosphates", Science, vol. 235, www.sciencemag.org, Mar. 6, 1987, 1174-1178.
Wu, et al., "3-O-modified nucleotides as reversible terminators for pyrosequencing", PNAS; vol. 104; No. 42, Oct. 16, 2007, 16462-16467.

(56) References Cited

OTHER PUBLICATIONS

Wu, et al., "Termination of DNA synthesis by N6-alkylated, not 3'-O-alkylated, photocleavable 2'-deoxyadenosine triphosphates", Nucleic Acids Research, vol. 35, No. 19, 2007, 6339-6349.
Wu, Jian, "Molecular Engineering of Novel Nucleotide Analogues for DNA Sequencing by Synthesis", Columbia University, 2008.
Yoshimoto, et al., "Tris(2,4,6-trimethoxyphenyl)phosphine (TTMPP): A Novel Catalyst for Selective Deacetylation", Chemistry Letters, Department of Chemistry, Faculty of Science, Kobe University, Kobe 657-8501, 2001, 934-935.
Zhang, Shenlong, "Development of New DNA Sequencing Approaches and Investigation of Vision-related Proteins Using Synthetic Chemistry", Columbia University, 2008.
Zimmerman, Eilene, "The Smartest Company in the World. And It's Not Google", MIT Tech Review vol. 117, No. 2, dated Mar./Apr. 2014, 27-29.
U.S. Appl. No. 90/008,152, filed Aug. 3, 2006, Hiatt et al., reexam requested by Gitten.
U.S. Appl. No. 90/008,149, filed Aug. 3, 2006, Hiatt et al., reexam requested by Gitten.
U.S. Appl. No. 13/791,597, filed Mar. 8, 2013, Balasubramanian et al.
Bergmann, et al., "Allyl as Internucleotide Protecting Group in DNA Synthesis to Be Cleaved Off by Ammonia", Tetrahedron, 51(25):6971-6976 (1995).
Brunckova, et al., "Intramolecular Hydrogen Atom Abstraction in Carbohydrates and Nucleosides: Inversion of an α- to β-Manopyranoside and Generation of Thymidine C-4' Radicals", Tetrahedron Letters 35:6619-6622 (1994).
Burgess, et al., "An Approach to Photolabile, Fluorescent Protecting Groups", J. Org. Chem., 62:5165-5168 (1997).
Buschmann, et al., "Spectroscopic Study and Evaluation of Red-Absorbing Fluorescent Dyes", Bioconjugate Chem. 14:195-204 (2003).
Canard, et al., "Catalytic Editing Properties of DNA Polymerases", Proc. Natl. Acad. Sci., 92:10859-10863 (1995).
Canard, et al., "DNA Polymerase Fluorescent Substrates with Reversible 3'-Tags", Gene, 148:1-6 (1994).
Crespo-Hernandez, et al., "Part 1. Photochemical and Photophysical Studies of Guanine Derivatives: Intermediates Contributing to its Photodestruction Mechanism in Aqueous Solution and the Participation of the Electron Adduct", Photochemistry and Photobiology, 71(5):534-543 (2000).
"Gene Characterization Kits", p. 39, Stratagene Catalog (1988).
Greene, et al., "Protective Groups in Organic Synthesis", John Wiley & Sons, New York, pp. 67-74 & 574-576 (1999).
Greene, et al., "Protective Groups in Organic Synthesis", John Wiley & Sons, New York, pp. 17-21, 31-33, 35-39, 42-45, 114-115, 413, & 417 (1991).
Guibe, et al., "Allylic Protecting Groups and Their Use in a Complex Environment, Part I: Allylic Protection of Alcohols", Tetrahedron, 53(40):13509-13556 (1997).
Guibe, et al., "Allylic Protecting Groups and Their Use in a Complex Environment, Part II: Allylic Protecting Groups and Their Removal Through Catalytic Palladium pi-Allyl Methodology", Tetrahedron, 54(13):2967-3042 (1998).
Hayakawa, et al., "O-Allyl Protection of Guanine and Thymine Residues in Oligodeoxyribonucleotides", J. Organometallic Chemistry, 58:5551-5555 (1993).
Henner, et al., "Enzyme Action at 3' Termini of Ionizing Radiation-Induced DNA Strand Breaks", J. Biological Chemistry, 258:15198-15205 (1983).
Hovinen et al., "Synthesis of 3'-O-(ω-Aminoalkoxymethyl)thymidine 5-Triphosphates, Terminators of DNA Synthesis that Enable 3'-Labelling", JCS Perkin Trans I, 211-217 (1994).
Ikeda, et al., "A Non-Radioactive DNA Sequencing Method Using Biotinylated Dideoxynucleoside Triphospates and ΔTth DNA Polymerase", DNA Research, 2:225-227 (1995).

Kamal et al., "A Mild and Rapid Regeneration of Alcohols from Their Allylic Ethers by Chlorotrimethylsilane/Sodium Iodide", Tetrahedron Letters, 40:371-372 (1999).
Kitamura, et al., "(P($C_6H_5$)$_3$)CpRu$^+$-Catalyzed Deprotection of Allyl Carboxylic Esters", J. Organic Chemistry, 67(14): 4975-4977 (2002).
Kloosterman, et al., "The Relative Stability of Allyl Ether, Allyloxycarbonyl Ester and Prop-2 Enylidene Acetal Protective Groups Toward Iridium, Rhodium and Palladium Catalysts", Tetrahedron Letters, 26(41):5045-5048 (1985).
Kocienski, "Protecting Groups", Georg Tieme Verlag, Stuttgart, 61-68 (1994).
Kraevskii, et al., "Substrate Inhibitors of DNA Biosynthesis", Translated from Molekulyarnaya Biologiya (Moscow) (Molecular Biology) 21(1):33-38 (1987).
Krecmerova, et al., "Synthesis of 5' -O-Phosphonomethyl Derivatives of Pyrimidine 2'-Deoxynucleosides", Collect. Czech. Chem. Commun. 55:2521-2536 (1990).
Kurata, et al., "Fluorescent Quenching-Based Quantitative Detection of Specific DNA/RNA Using a BODIPY® FL-Labeled Probe or Primer", Nucleic Acids Research, 29(6): E34 (2001).
Kvam, et al., "Characterization of Singlet Oxygen-Induced Guanine Residue Damage After Photochemical Treatment of Free Nucleosides and DNA", Biochimica et Biophysica Acta., 1217:9-15 (1994).
Li, et al., "A Photocleavable Fluorescent Nucleotide for DNA Sequencing and Analysis", Proc. Natl. Acad. Sci. 100:414-419 (2003).
Maier, et al., "Synthesis and Properties of New Fluorescein-Labeled Oligonucleotides", Nucleosides & Nucleotides, 14:961-965 (1995).
Markiewicz, et al., "A New Method of Synthesis of Fluorescently Labelled Oligonucleotides and Their Application in DNA Sequencing", Nucleic Acids Research, 25:3672-3680 (1997).
Marquez, et al., "Selective Fluorescence Quenching of 2,3-Diazabicyclo(2.2.2)oct-2-ene by Nucleotides", Organic Letters, 5:3911-3914 (2003).
Metzker, "Termination of DNA Synthesis by Novel 3'-Modified-Deoxyribonucleoside 5'-Triphosphases", Nucleic Acids Research, 22(20):4259-4267 (1994).
Nazarenko, et al., "Effect of Primary and Secondary Structure of Oligodeoxyribonucleotides on the Fluorescent Properties of Conjugated Dyes", Nucleic Acids Research, 30:2089-2095 (2002).
Nishino, et al., "Efficient Deanilidation of Phosphoranilidates by the Use of Nitrites and Acetic /Anhydride", Heteroatom Chemistry, 2:187-196 (1991).
Olejnik, et al., "Photocleavable Biotin Derivatives: A Versatile Approach for the Isolation of Biomolecules", Proc. Natl. Acad. Sci. 92:7590-7594 (1995).
Oksman, et al., "Conformation of 3'-Substituted 2', 3'-Dideoxyribonucleosides in Aqueous Solution: Nucleoside Analogs with Potential Antiviral Activity", Nucleosides & Nucleotides, 10(1-3):567-568 (1991).
Oksman, et al., "Solution Conformations and Hydrolytic Stability of 2'- and 3'-Substituted 2', 3'-Dideoxyribonucleosides, Including Some Potential Inhibitors of Human Immunodeficiency Virus", Journal of Physical Organic Chemistry, 5(22):741-747 (1992).
Prober et al., "System for Rapid DNA Sequencing with Fluroescent Chain-Terminating Dideoxynucleotides," Science, 238:336-341 (1987).
Quaedflieg, et al., "An Alternative Approach Towards the Synthesis of (3'→5') Methylene Acetal Linked Dinucleosides", Tetrahedron Letters, 33(21):3081-3084 (1992).
Rao, et al., "Four Color FRET Dye Nucleotide Terminators for DNA Sequencing", Nucleosides, Nucleotides, & Nucleic Acids, 20:673-676 (2001).
Rasolonjatovo, et al., "6-N-(N-Methylanthranylamido)-4-Oxo-Hexanoic Acid: A New Fluorescent Protecting Group Applicable to a New DNA Sequencing Method", Nucleosides & Nucleotides, 17:2021-2025 (1998).
Sarfati, et al., "Synthesis of Fluorescent Derivatives of 3'-O-(6-Aminohexanoyl)-pyrimidine Nucleosides 5'-Triphosphates that Act as DNA Polymerase Substrates Reversibly Tagged at C-3'", JCS Perkin Trans I, 1163-1171 (1995).

(56) References Cited

OTHER PUBLICATIONS

Seeger, "Single Molecule Fluorescence: High-Performance Molecular Diagnosis and Screening", Bioforum, Git Verlag, Darmstadt, DE, 21(4):179-185 (German text and English translation) (1998).
Torimura, et al., "Fluorescence-Quenching Phenomenon by Photoinduced Electron Transfer Between a Fluorescent Dye and Nucleotide Base", Analytical Sciences, 17:155-160 (2001).
Veeneman, et al., "An Efficient Approach to the Synthesis of Thymidine Derivatives Containing Phosphate-Isosteric Methylene Acetal Linkages", Tetrahedron, 47:1547-1562 (1991).
Wada, et al., "2-(Azidomethyl)benzoyl as a New Protecting Group in Nucleosides", Tetrahedron Letters, 42:1069-1072 (2001).
Welch, et al., "Syntheses of Nucleosides Designed for Combinatorial DNA Sequencing", Chemistry, European Journal, 5:951-960 (1999).
Yamashita, et al., "Studies of Antitumor Agents, VII. Antitumor Activities of O-Alkoxyalkyl Derivatives of 2'-Deoxy-5-trifluoromethyluridine", Chem. Pharm. Bull., 35:2373-2381 (1987).
Zavgorodny, et al., "1-Alkylthioalkylation of Nucleoside Hydroxyl Functions and its Synthetic Applications", Tetrahedron Letters, 32(51):7593-7596 (1991).
Zavgorodny, et al., "S,X-Acetals in Nucleoside Chemistry III. Synthesis of 2' and 3'-O-Azidomethyl Derivatives of Ribonucleosides", Nucleosides, Nucleotides & Nucleic Acids, 19(10-12):1977-1991 (2000).
Notice of Allowance mailed Nov. 8, 2012 in U.S. Appl. No. 13/281,275.
Notice of Allowance mailed Jan. 17, 2013 in U.S. Appl. No. 13/432,989.
Office Action mailed Apr. 22, 2013 in U.S. Appl. No. 13/437,772.
Jung, et al., "Conversion of Alkyl Carbamates into Amines via Treatment with Trimethylsilyl Iodide", J.C.S. Chem. Comm., 7:315-316 (1978).
Beckman Coulter CEQ(TM) 2000 DNA Analysis System User's Guide, 606913-AC, dated Jun. 2000.
Petition for Inter Partes Review of U.S. Patent No. 7,057,026, dated Jan. 29, 2013.
Revised Petition for Inter Partes Review of U.S. Patent No. 7,057,026, dated Feb. 7, 2013.
Petition for Inter Partes Review of U.S. Patent No. 8,158,346, dated May 4, 2013.
Bystrom, et al., "ATP Analogs With Non-Transferable Groups in the Y Position as Inhibitors of Glycerol Kinase", Bioorganic & Medicinal Chemistry Letters, vol. 7, No. 20, 1997, 2613-2616.
Fuchs, "Handbook of Reagents for Organic Synthesis, Reagents for Silicon-Mediated Organic Synthesis", Purdue University, West Lafayette, IN, USA John Wiley & Sons Ltd, 2011, i-iv, 325-336.
Gitten, "U.S. Re-Examination Application No. 90/008,149, filed Aug. 3, 2006, Re-Exam Certificate Issued on Dec 30, 2008", Aug. 3, 2006.
Gitten, "U.S. Re-Examination Application No. 90/008,152, filed Aug 3, 2006, Re-Exam Certificate Issued on Aug. 12, 2008", Aug. 3, 2006.
Green, T.W. et al., "Protective Groups in organic synthesis", A Wiley-Interscience Publications, Jan. 1, 1999, 67-74, 474.
Greene, et al., "Protective Groups in Organic Synthesis", John Wiley & Sons, New York, 1991, 42-45, and 417.
Greene, et al., "Protective Groups in Organic Synthesis", John Willey & Sons, New York, 1-316, 1999.
Greene, et al., "Protective Groups in Organic Synthesis", Third Edition, 1999, 17-245, 700-723.
Guiller, et al., "Linkers and cleavage Strategies in Solid-Phase Organic Synthesis and Combinatorial Chemistry", Chem. Rev. 100, 2000, 2091-2157.
Hayakawa, Y. et al., "A general approach to nucleoside 3' - and 5'-monophosphates", Tetrahedron Letters, vol. 28, 1987, 2259-2262.
IPR2013-00128, "Amended Complaint for Patent Infringement", dated Apr. 11, 2012.
IPR2013-00128, "Columbia University's Answer to Illumina's Amended Counterclaims for Declaratory Judgment", dated Jan. 7, 2013.
IPR2013-00128, "Columbia University's Response to Illumina's Requests for Admission", dated Apr. 8, 2013.
IPR2013-00128, "Curriculum Vitae Floyd Eric Romesberg", dated Aug. 2013.
IPR2013-00128, "Decision IBS's Motion for Pro Hac Vice Admission of Jason P. Grier", dated Jan. 10, 2014.
IPR2013-00128, "Decision Illumina's Motion for Pro Hac Vice Admission of William R. Zimmerman", dated Oct. 1, 2013.
IPR2013-00128, "Decision Institution of Inter Partes Review", dated Jul. 29, 2013.
IPR2013-00128, "Decision Motion to Withdraw", dated Sep. 10, 2013.
IPR2013-00128, "Decision", dated Apr. 26, 2013.
IPR2013-00128, "Declaration of Dr. Bruce Branchaud in Support of Petition for Inter Partes Review of U.S. Patent No. 7,057,026", Jan. 28, 2013, 1-41.
IPR2013-00128, "Declaration of Dr. Bruce P. Branchaud in Support of Petition for Inter Partes Review of U.S. Patent No. 7,057,026", dated Jun. 4, 2013.
IPR2013-00128, "Declaration of Eric Vermaas Accompanying Patent Owner's Motion to Amend", dated Oct. 24, 2013.
IPR2013-00128, "Declaration of Floyd Romesberg, Ph.D.", dated Oct. 24, 2013.
IPR2013-00128, "Declaration of Jason P. Grier in Support of Petitioner's Motion for Admission Pro Hac Vice of Jason P. Grier", dated Dec. 23, 2013.
IPR2013-00128, "Declaration of Ryan Drost", dated Sep. 12, 2012.
IPR2013-00128, "Declaration of William R. Zimmerman in Support of Motion to Appear Pro Hac Vice on Behalf of Patent Owner Illumina Cambridge Ltd.", dated Sep. 11, 2013.
IPR2013-00128, "Deposition Transcript of Bruce Branchaud, Ph.D. held on Oct. 3, 2013", dated Oct. 24, 2013.
IPR2013-00128, "English Translation of WO98/33939", dated Aug. 6, 1998.
IPR2013-00128, "ERRATA", dated Feb. 1, 2013.
IPR2013-00128, "Excerpts from the '026 file history", 2013.
IPR2013-00128, "Exhibit List", dated Jan. 29, 2013.
IPR2013-00128, "Illumina Cambridge Limited Mandatory Notices", Feb. 18, 2013.
IPR2013-00128, "Illumina Cambridge Limited's Power of Attorney in an Inter Partes Review", dated Feb. 18, 2013.
IPR2013-00128, "Illumina Cambridge Limited's Updated Power of Attorney in an Inter Partes Review", dated Sep. 16, 2013.
IPR2013-00128, "Illumina Cambridge Ltd Preliminary Response", dated May 1, 2013.
IPR2013-00128, "Illumina Motion for Counsel to Withdraw From the Proceeding to Permit Substitution of Counsel", dated Aug. 30, 2013.
IPR2013-00128, "Illumina Motion to Seal", dated Oct. 24, 2013.
IPR2013-00128, "Illumina Notice of Cross-Examination Deposition of IBS Declarant Dr. Bruce P. Branchaud", dated Sep. 19, 2013.
IPR2013-00128, "Illumina Supplemental Mandatory Notice: Additional Backup Counsel", dated Oct. 1, 2013.
IPR2013-00128, "Illumina Updated Exhibit List", dated Oct. 24, 2013.
IPR2013-00128, "Illumina Updated Exhibit List", dated Sep. 23, 2013.
IPR2013-00128, "Illumina's Motion to Amend", dated Oct. 24, 2013.
IPR2013-00128, "Illumina's First Supplemental Mandatory Notices", dated Sep. 11, 2013.
IPR2013-00128, "Illumina's Second Supplemental Mandatory Notices", dated Sep. 17, 2013.
IPR2013-00128, "Intelligent Bio-System, Inc.'s Current Exhibit List", dated Dec. 23, 2013.
IPR2013-00128, "Intelligent Bio-System, Inc.'s Current Exhibit List", dated Sep. 17, 2013.
IPR2013-00128, "Intelligent Bio-Systems Inc.'s List of Proposed Motions", dated Aug. 27, 2013.
IPR2013-00128, "Intelligent Bio-Systems, Inc.'s Responses to Illumina, Inc.'s First Set of Requests for Admission to IBS", dated Apr. 8, 2013.

(56) References Cited

OTHER PUBLICATIONS

IPR2013-00128, "Intelligent Bio-Systems' Notice of Cross-Examination Deposition of Illumina's Declarant Dr. Floyd Romesberg", dated Dec. 23, 2013.
IPR2013-00128, "Intelligent Bio-Systems' Notice of Cross-Examination Deposition of Illumina's Declarant Mr. Eric Vermaas", dated Dec. 23, 2013.
IPR2013-00128, "Intelligent Bio-Systems' Response to Order", dated Feb. 7, 2013.
IPR2013-00128, "List of Documents Considered by Floyd Romesberg, Ph.D., in Preparing Declaration", dated Oct. 24, 2013.
IPR2013-00128, "Motion for William R. Zimmerman to Appear Pro Hac Vice on Behalf of Patent Owner Illumina Cambridge Ltd.", dated Sep. 23, 2013.
IPR2013-00128, "Notice of Filing Date Accorded to Petition and Time for Filing Patent Owner Preliminary Response", dated Feb. 1, 2013.
IPR2013-00128, "Order (Regarding Conference Call)", dated Jan. 31, 2013.
IPR2013-00128, "Order Conduct of the Proceeding", dated Aug. 14, 2013.
IPR2013-00128, "Order Conduct of the Proceeding", dated Aug. 29, 2013.
IPR2013-00128, "Order Conduct of the Proceeding", dated Oct. 22, 2013.
IPR2013-00128, "Order Conduct of the Proceeding", dated Sep. 16, 2013.
IPR2013-00128, "Patent Owner Illumina's Additional Power of Attorney", dated Sep. 23, 2013.
IPR2013-00128, "Patent Owner Illumina's Proposed Motions", dated Aug. 27, 2013.
IPR2013-00128, "Petition for Inter Partes Review of U.S. Pat. No. 7,057,026", dated Jan. 29, 2013.
IPR2013-00128, "Petition for Inter Partes Review of U.S. Pat. No. 7,713,698", dated Sep. 16, 2012.
IPR2013-00128, "Petition for Inter Partes Review of U.S. Pat. No. 7,790,869", dated Sep. 16, 2012.
IPR2013-00128, "Petition for Inter Partes Review of U.S. Pat. No. 8,088,575", dated Oct. 3, 2012.
IPR2013-00128, "Petitioner's Motion for Admission Pro Hac Vice of Jason P. Grier", dated Dec. 23, 2013.
IPR2013-00128, "Petitioner's Motion for Admission Pro Hac Vice of Robert R. Baron, Jr.", dated Apr. 16, 2013.
IPR2013-00128, "Power of Attorney and Certificate of Service", dated Jan. 29, 2013.
IPR2013-00128, "Revised Petition for Inter Partes Review of U.S. Pat. No. 7,057,026", dated Feb. 7, 2013.
IPR2013-00128, "Scheduling Order", dated Jul. 29, 2013.
IPR2013-00128, "Signed Deposition Transcript of Dr. Bruce Branchaud", dated Oct. 3, 2013.
IPR2013-00128, "Transcript of Initial Conference Call Held on Aug. 29, 2013", dated Sep. 17, 2013.
IPR2013-00128, U.S. Appl. No. 10/227,131, dated Aug. 23, 2002.
IPR2013-00128, "USP 7,057,026 File History", dated Oct. 24, 2013.
IPR2013-00266, "Curriculum Vitae Floyd Eric Romesberg", dated Dec. 30, 2013.
IPR2013-00266, "Decision IBS's Motion for Pro Hac Vice Admission of Jason P. Grier", dated Jan. 10, 2014.
IPR2013-00266, "Decision Illumina's Motion for Pro Hac Vice Admission of William R. Zimmerman", Dated Dec. 7, 2013.
IPR2013-00266, "Decision Institution of Inter Partes Review", dated Oct. 28, 2013.
IPR2013-00266, "Decision Intelligent Bio-Systems' Motion for Pro Hac Vice Admission of Robert R. Baron, Jr.", dated Aug. 9, 2013.
IPR2013-00266, "Decision Motion to Withdraw", dated Sep. 10, 2013.
IPR2013-00266, "Declaration of Dr. Bruce P. Branchaud in Support of Petition for Inter Partes Review of U.S. Patent No. 8,158,346", dated May 3, 2013.
IPR2013-00266, "Declaration of Floyd Romesberg, Ph.D., in Support of Patent Owner's Motion to Amend", dated Dec. 30, 2013.
IPR2013-00266, "Declaration of Jason P. Grier in Support of Petitioner's Motion for Admission Pro Hac Vice of Jason P. Grier", dated Dec. 23, 2013.
IPR2013-00266, "Declaration of Robert R. Baron, Jr. in Support of Petitioner'S Motion for Admission Pro Hac Vice of Robert R. Baron, Jr.", dated Jul. 19, 2013.
IPR2013-00266, "Declaration of William R. Zimmerman in Support of Motion to Appear Pro Hac Vice on Behalf of Patent Owner Illumina Cambridge Ltd.", dated Nov. 21, 2013.
IPR2013-00266, "Excerpts from the '346 Patent File History", dated May 4, 2013.
IPR2013-00266, "Excerpts from the file history of European Patent Application No. 02781434.2", dated May 4, 2013.
IPR2013-00266, "Exhibit List", dated May 4, 2013.
IPR2013-00266, "Illumina Cambridge Limited Mandatory Notices", dated May 24, 2013.
IPR2013-00266, "Illumina Cambridge Limited's Power of Attorney in an Inter Partes Review", dated May 24, 2013.
IPR2013-00266, "Illumina Cambridge Limited's Updated Power of Attorney in an Inter Partes Review", dated Sep. 16, 2013.
IPR2013-00266, "Illumina Cambridge Ltd Preliminary Response", dated Aug. 5, 2013.
IPR2013-00266, "Illumina Motion for Counsel to Withdraw From the Proceeding to Permit Substitution of Counsel", dated Aug. 30, 2013.
IPR2013-00266, "Illumina Motion to Seal", dated Dec. 30, 2013.
IPR2013-00266, "Illumina Updated Exhibit List", dated Dec. 30, 2013.
IPR2013-00266, "Illumina Updated Exhibit List", dated Nov. 21, 2013.
IPR2013-00266, "Illumina's Motion to Amend", dated Dec. 30, 2013.
IPR2013-00266, "Illumina's First Supplemental Mandatory Notices", dated Sep. 11, 2013.
IPR2013-00266, "Illumina's Second Supplemental Mandatory Notices", dated Sep. 17, 2013.
IPR2013-00266, "Intelligent Bio-System, Inc.'s Current Exhibit List", dated Dec. 23, 2013.
IPR2013-00266, "Intelligent Bio-Systems Inc.'s List of Proposed Motions", dated Nov. 14, 2013.
IPR2013-00266, "Inter Partes Review—Petitioner Power of Attorney", dated May 4, 2013.
IPR2013-00266, "List of Documents Considered by Floyd Romesberg, Ph.D., in Preparing Declaration", Dec. 30, 2013.
IPR2013-00266, "Motion for William R. Zimmerman to Appear Pro Hac Vice on Behalf of Patent Owner Illumina Cambridge Ltd", dated Nov. 21, 2013.
IPR2013-00266, "Notice of Filing Date Accorded to Petition and Time for Filing Patent Owner Preliminary Response", dated May 8, 2013.
IPR2013-00266, "Order Conduct of Proceeding", dated Aug. 29, 2013.
IPR2013-00266, "Order Conduct of the Proceeding", dated Nov. 26, 2013.
IPR2013-00266, "Patent Owner Illumina's Additional Power of Attorney", dated Nov. 21, 2013.
IPR2013-00266, "Patent Owner Illumina's Proposed Motions", dated Nov. 14, 2013.
IPR2013-00266, "Petition for Inter Partes Review of U.S. Pat. No. 7,713,698", dated Sep. 16, 2012.
IPR2013-00266, "Petition for Inter Partes Review of U.S. Pat. No. 7,790,869", dated Sep. 16, 2012.
IPR2013-00266, "Petition for Inter Partes Review of U.S. Pat. No. 8,088,575", dated Oct. 3, 2012.
IPR2013-00266, "Petition for Inter Partes Review of U.S. Pat. No. 8,158,346", dated May 4, 2013.
IPR2013-00266, "Petitioner's Motion for Admission Pro Hac Vice of Jason P. Grier", dated Dec. 23, 2013.
IPR2013-00266, "Petitioner's Motion for Admission Pro Hac Vice of Robert R. Baron, Jr", dated Jul. 19, 2013.

(56) References Cited

OTHER PUBLICATIONS

IPR2013-00266, "Redacted Declaration of Eric Vermaas Accompanying Patent Owner's Motion to Amend", dated Dec. 20, 2013.
IPR2013-00266, "Scheduling Order", dated Oct. 28, 2013.
IPR2013-00266, "*The Trustees of Columbia University in the City of New York* v. *Illumina, Inc.*", 1:12-cv-00376-GMS (D.Del.) Columbia's Answer to Illumina's Amended Counterclaims for Declaratory Judgment, Doc. 72, Jan. 7, 2013.
IPR2013-00266, "*The Trustees of Columbia University in the City of New York* v. *Illumina, Inc.*", 1:12-cv-00376-GMS (D.Del.), Columbia's Amended Complaint, Doc. 5, dated Apr. 11, 2012.
IPR2013-00324, "Decision Denying Institution of Inter Partes Review", dated Nov. 21, 2013.
IPR2013-00324, "Decision Intelligent Bio-Systems' Motion for Pro Hac Vice Admission of Robert R. Baron, Jr.", dated Aug. 9, 2013.
IPR2013-00324, "Decision Motion to Withdraw", dated Sep. 10, 2013.
IPR2013-00324, "Declaration of Dr. Bruce P. Branchaud in Support of Petition for Inter Partes Review of U.S. Patent No. 7,057,026", dated Jun. 4, 2013.
IPR2013-00324, "Declaration of Robert R. Baron, Jr. in Support of Petitioner's Motion for Admission Pro Hac Vice of Robert R. Baron, Jr.", dated Jul. 19, 2013.
IPR2013-00324, "Excerpts from the '026 file history", dated Jun. 4, 2013.
IPR2013-00324, "Excerpts from the EP 02781434.2 File History", Oct. 13, 2008.
IPR2013-00324, "Exhibit List", dated Jun. 4, 2013.
IPR2013-00324, "Illumina Cambridge Limited Mandatory Notices", dated Jun. 24, 2013.
IPR2013-00324, "Illumina Cambridge Limited's Power of Attorney in an Inter Partes Review", dated Jun. 24, 2013.
IPR2013-00324, "Illumina Cambridge Limited's Updated Power of Attorney in an Inter Partes Review", dated Sep. 16, 2013.
IPR2013-00324, "Illumina Motion for Counsel to Withdraw From the Proceeding to Permit Substitution of Counsel", dated Aug. 30, 2013.
IPR2013-00324, "Illumina Notice of Waiver of Patent Owner Preliminary Response", dated Sep. 9, 2013.
IPR2013-00324, "Illumina's First Supplemental Mandatory Notices", dated Sep. 11, 2013.
IPR2013-00324, "Illumina's Second Supplemental Mandatory Notices", dated Sep. 17, 2013.
IPR2013-00324, "Intelligent Bio-System, Inc.'s Current Exhibit List", dated Jul. 19, 2013.
IPR2013-00324, "Inter Partes Review—Petitioner Power of Attorney", dated Jun. 4, 2013.
IPR2013-00324, "Notice of Filing Date Accorded to Petition and Time for Filing Patent Owner Preliminary Response", dated Jun. 4, 2013.
IPR2013-00324, "Notice of Filing Date Accorded to Petition and Time for Filing Patent Owner Preliminary Response", dated Jun. 6, 2013.
IPR2013-00324, "Order Conduct of the Proceeding", dated Aug. 29, 2013.
IPR2013-00324, "Petition for Inter Partes Review of U.S. Pat. No. 7,057,026", dated Jun. 4, 2013.
IPR2013-00324, "Petitioner's Motion for Admission Pro Hac Vice of Robert R. Baron, Jr.", dated Jul. 19, 2013.
IPR2013-00517, "Decision IBS's Motion for Pro Hac Vice Admission of Jason P. Grier", dated Dec. 23, 2013.
IPR2013-00517, "Decision IBS's Motion for Pro Hac Vice Admission of Jason P. Grier", dated Jan. 10, 2014.
IPR2013-00517, "Decision IBS's Motion for Pro Hac Vice Admission of Robert R. Baron, Jr.", dated Jan. 10, 2014.
IPR2013-00517, "Declaration of Dr. Bruce P. Branchaud in Support of Petition for Inter Partes Review of U.S. Patent No. 7,566,537", dated Aug. 16, 2013.
IPR2013-00517, "Declaration of Jason P. Grier in Support of Petitioner's Motion for Admission Pro Hac Vice of Jason P. Grier", dated Dec. 23, 2013.
IPR2013-00517, "Declaration of Robert R. Baron, Jr. in Support of Petitioner's Motion for Admission Pro Hac Vice of Robert R. Baron, Jr.", dated Dec. 23, 2013.
IPR2013-00517, "Excerpts from the Deposition Transcript of Dr. Xiaohai Liu", dated Mar. 20, 2013.
IPR2013-00517, "Exhibit List", dated Aug. 19, 2013.
IPR2013-00517, "Illumina Notice of Waiver of Patent Owner Preliminary Response", dated Nov. 26, 2013.
IPR2013-00517, "Intelligent Bio-System, Inc.'s Current Exhibit List", dated Dec. 23, 2013.
IPR2013-00517, "Intelligent Bio-Systems, Inc.'s Response to Notice of Filing Date Accorded to Petition and Time for Filing Patent Owner Preliminary Response", dated Aug. 30, 2013.
IPR2013-00517, "Inter Partes Review—Petitioner Power of Attorney", dated Aug. 19, 2013.
IPR2013-00517, "Notice of Filing Date Accorded to Petition and Time for Filing Patent Owner Preliminary Response", dated Aug. 26, 2013.
IPR2013-00517, "Patent Owner Illumina's Power of Attorney", dated Sep. 9, 2013.
IPR2013-00517, "Patent Owner Submission of Mandatory Notice Information", dated Sep. 9, 2013.
IPR2013-00517, "Petition for Inter Partes Review of U.S. Pat. No. 7,566,537", dated Aug. 19, 2013.
IPR2013-00517, "Petition for Inter Partes Review of U.S. Pat. No. 7,713,698", dated Sep. 16, 2012.
IPR2013-00517, "Petition for Inter Partes Review of U.S. Pat. No. 7,790,869", dated Sep. 16, 2012.
IPR2013-00517, "Petition for Inter Partes Review of U.S. Pat. No. 8,088,575", dated Oct. 3, 2012.
IPR2013-00517, "Petitioner's Motion for Admission Pro Hac Vice of Jason P. Grier", dated Dec. 23, 2013.
IPR2013-00517, "Petitioner's Motion for Admission Pro Hac Vice of Robert R. Baron, Jr.", dated Dec. 23, 2013.
IPR2013-00517, "Revised Petition for Inter Partes Review of U.S. Pat. No. 7,566,537", dated Aug. 30, 2013.
IPR2013-00517, "Translation Affadavit for Loubinoux", Mar. 18, 2013.
IPR2013-00517, U.S. Appl. No. 09/684,670, dated Oct. 6, 2000.
IPR2013-00518, "Decision IBS's Motion for Pro Hac Vice Admission of Jason P. Grier", dated Jan. 10, 2014.
IPR2013-00518, "Decision IBS's Motion for Pro Hac Vice Admission of Robert R. Baron, Jr.", dated Jan. 10, 2014.
IPR2013-00518, "Declaration of Dr. Bruce P. Branchaud in Support of Petition for Inter Partes Review of U.S. Patent No. 7,566,537", dated Aug. 16, 2013.
IPR2013-00518, "Declaration of Jason P. Grier in Support of Petitioner's Motion for Admission Pro Hac Vice of Jason P. Grier", dated Dec. 23, 2013.
IPR2013-00518, "Declaration of Robert R. Baron, Jr. in Support of Petitioner'S Motion for Admission Pro Hac Vice of Robert R. Baron, Jr.", dated Dec. 23, 2013.
IPR2013-00518, "Excerpts from the '537 Patent File History", dated Aug. 19, 2013.
IPR2013-00518, "Excerpts from the file history of European Patent Application No. 02781434.2", dated Aug. 9, 2013.
IPR2013-00518, "Exhibit List", dated Aug. 19, 2013.
IPR2013-00518, "Illumina Notice of Waiver of Patent Owner Preliminary Response", dated Nov. 26, 2013.
IPR2013-00518, "Intelligent Bio-System, Inc.'s Current Exhibit List", dated Dec. 23, 2013.
IPR2013-00518, "Inter Partes Review—Petitioner Power of Attorney", dated Aug. 19, 2013.
IPR2013-00518, "Notice of Filing Date Accorded to Petition and Time for Filing Patent Owner Preliminary Response", dated Aug. 26, 2013.
IPR2013-00518, "Patent Owner Illumina's Power of Attorney", dated Sep. 9, 2013.
IPR2013-00518, "Patent Owner Submission of Mandatory Notice Information", dated Sep. 9, 2013.

(56) References Cited

OTHER PUBLICATIONS

IPR2013-00518, "Petition for Inter Partes Review of U.S. Pat. No. 7,566,537", dated Aug. 19, 2013.
IPR2013-00518, "Petition for Inter Partes Review of U.S. Pat. No. 7,713,698", dated Sep. 16, 2013.
IPR2013-00518, "Petition for Inter Partes Review of U.S. Pat. No. 7,790,869", dated Sep. 16, 2012.
IPR2013-00518, "Petition for Inter Partes Review of U.S. Pat. No. 8,088,575", dated Oct. 3, 2013.
IPR2013-00518, "Petitioner's Motion for Admission Pro Hac Vice of Jason P. Grier", dated Dec. 23, 2013.
IPR2013-00518, "Petitioner's Motion for Admission Pro Hac Vice of Robert R. Baron, Jr.", dated Dec. 23, 2013.
IPR2013-00518, U.S. Appl. No. 09/684,670, dated Oct. 6, 2000.
Katagiri, et al., "Selective Protection of the Primary Hydroxyl Groups of Oxetanocn A and Conformational Analysis of O-Protected Oxetanocin A1", Chem. Pharm. Bull., vol. 43, No. 5,, 1995, 884-886.
Maxam, et al., "A new method for sequencing DNA", Proceedings of the National Academy of Sciences, vol. 74, No. 2, Feb. 1, 1977, 560-564.
Ruby, et al., "Affinity Chromatography with Biotynlated RNAs", Methods in Enxymology, vol. 181, 1990, 97-121.
Sanger, et al., "DNA sequencing with chain-terminating inhibitors", Proc. Natl. Acad. Sci. USA, vol. 74, No. 12, Biochemistry, Dec. 1977, 5463-5467.
Welch, et al., "Synthesis of Fluorescent, Photolabile 3'-O-Protected Nucleoside Triphosphates for the Base Addition Sequencing Scheme", Nucleosides & Nucleotides, 18(2), 1999, 197-201.
IPR2013-00128 # 1, "Proceedings", Apr. 23, 2014.
IPR2013-00128 # 2, "Decision, Motion to Seal", Jun. 4, 2014.
IPR2013-00128 # 3, "Petitioner Intelligent Bio-Systems, Inc.'s Updated Mandatory Notice of Counsel", Jun. 6, 2014.
IPR2013-00128 # 4, "Final ritten Decision", Jul. 25, 2014.
IPR2013-00128 # 5, "Decision, Request to Preserve Recording Pending Appeal", Sep. 10, 2014.
IPR2013-00128 # 6, "Renewed Motion for Attorneys to Withdraw as Backup Counsel for Illumina", Sep. 23, 2014.
IPR2013-00128 # 7, "Illumina Notice of Appeal in the U.S. Court of Appeals for the Federal Circuit", Sep. 24, 2014.
IPR2013-00128 # 8, "Decision, Motion to Withdraw", Oct. 7, 2014.
IPR2013-00128 # 9, "Petitioner Intelligent Bio-Systems, Inc.'s Supplemental Mandatory Notice: Additional Backup Counsel", Jun. 3, 2014.
IPR2013-00128 # 10, "Illumina Revocation of Power of Attorney for James G. Morrow and James D. Borchardt", Oct. 27, 2014.
IPR2013-00266 # 1, "Petitioner Intelligent Bio-Systems, Inc.'s Updated Mandatory Notice of Counsel", Jun. 6, 2014.
IPR2013-00266 # 2, "Decision, Motion to Seal", Jun. 16, 2014.
IPR2013-00266 # 3, "Proceedings", Jul. 8, 2014.
IPR2013-00266 # 4, "Renewed Motion for Attorneys to Withdraw as Backup Counsel for Illumina", Jul. 29, 2014.
IPR2013-00266 # 5, "Decision, Motion to Withdraw", Oct. 7, 2014.
IPR2013-00266 # 6, "Illumina Revocation of Power of Attorney for James G. Morrow and James D. Borchardt", Oct. 27, 2014.
IPR2013-00266 # 7, "Final Written Decision", Oct. 28, 2014.
IPR2013-00266 # 8, "Erratum", Oct. 28, 2014.
IPR2013-00324 # 1, "Intelligent Bio-Systems, Inc. Request for Refund of Post-Institution Fee", Mar. 3, 2014.
IPR2013-00324 # 2, "Notice of Refund", Mar. 4, 2014.
IPR2013-00517 # 1, "Petitioner Intelligent Bio-Systems, Inc.'s Supplemental Mandatory Notice: Additional Backup Counsel", Jun. 3, 2014.
IPR2013-00517 # 2, "Power of Attorney", Jun. 3, 2014.
IPR2013-00517 # 3, "Petitioner Intelligent Bio-Systems, Inc.'s Corrected Supplemental Mandatory Notice: Additional Backup Counsel", Jun. 3, 2014.
IPR2013-00517 # 4, "Petitioner Intelligent Bio-Systems, Inc.'s Response to Illumina's Motion to Seal", Jun. 5, 2014.
IPR2013-00517 # 5, "Petitioner Intelligent Bio-Systems, Inc.'s Updated Mandatory Notice of Counsel", Jun. 3, 2014.
IPR2013-00517 # 6, "Notice of Stipulation to Change Due Date 2", Jun. 23, 2014.
IPR2013-00517 # 7, "Intelligent Bio-System's Notice of Cross-Examination Deposition of Illumina's Declarant Dr. Floyd Romesberg", Jun. 26, 2014.
IPR2013-00517 # 8, "Intelligent Bio-Systems' Notice of Cross-Examination Deposition of Illumina's Declarant Dr. Kevin Burgess", Jun. 27, 2014.
IPR2013-00517 # 9, "Declaration of Derek C. Walter in Support of Motion to Appear Pro Hac Vice on Behalf of Patent Owner Illumina Cambridge Ltd.", Jun. 23, 2014.
IPR2013-00517 # 10, "Illumina Updated Exhibit List", Jul. 7, 2014.
IPR2013-00517 # 11, "Motion for Derek C. Walter to Appear Pro Hac Vice on Behalf of Patent Owner Illumina Cambridge Ltd.", Jul. 7, 2014.
IPR2013-00517 # 12, "Illumina Reply to IBS Opposition to Illumina Motion to File Under Seal", Jul. 7, 2014.
IPR2013-00517 # 13, "Illumina Updated Mandatory Notice Adding Sheila N. Swaroop as Additional Backup Counsel", Jul. 7, 2014.
IPR2013-00517 # 14, "Illumina Additional Power of Attorney", Jul. 11, 2014.
IPR2013-00517 # 15, "Decision Illumina's Motion for Pro Hac Vice Admission of Derek C. Water", Jul. 15, 2014.
IPR2013-00517 # 16, "Illumina Updated Mandatory Notice Adding Derek C. Walter as Additional Backup Counsel", Jul. 18, 2014.
IPR2013-00517 # 17, "Liu Transcript p. 295, Exhibit 1022", Jul. 28, 2014.
IPR2013-00517 # 18, "Biophysical Society, Abstracts, Sixth Annual Meeting", Feb. 14-16, 1962.
IPR2013-00517 # 19, Ireland, et al., "Approach to the Total Synthesis of Chlorothricolide: Synthesis of (#)-19,20-Dihydro-24-O-metylchlorothricolide. Methyl Ester, Ethyl Carbonate", J. Org. Chem. 51, 1986, Jul. 28, 2014, 685-648.
IPR2013-00517 # 20, Kamal et al., "A Mild and Rapid Regeneration of Alcohols from their Allylic Ethers by Chlorotrimethylsilane/Sodium Iodide", Tetrahedrom Letters 40, 1999, Jul. 28, 2014, 31-372.
IPR2013-00517 # 21, "Videotaped Deposition of Kevin Burgess, Ph.D., taken before Greg S. Weiland, CSR, RMR, CRR, pursuant to the Applicable Rules Pertaining to the Taking of Depositions", Jul. 28, 2014.
IPR2013-00517 # 22, "Video Deposition of Floyd Romesberg, Ph.D.", Jul. 8, 2014.
IPR2013-00517 # 23, "Prosecution History Excerpt, Restriction Requirement", Jul. 12, 2007.
IPR2013-00517 # 24, "The American Heritage College Dictionary, Third Edition", Jul. 28, 2014.
IPR2013-00517 # 25, Faucher et al., "Tris(2-Carboxyethyl)phosphine (TECP) for the Reduction of Sulfoxides, Sulfonylchlorides, N-Oxides, and Azides", Synthetic Communications vol. 33, No. 22, 3503-3511.
IPR2013-00517 # 26, Variagenics, Inc., "U.S. Appl. No. 02/210,098", Mar. 14, 2002.
IPR2013-00517 # 27, Saxon et al., "Cell Surface Engineering by a Modified Staudinger Reaction", Science vol. 287, Mar. 17, 2000.
IPR2013-00517 # 28, Furniss et al., "Vogel's Textbook of Practical Organic Chemistry, Fifth Edition", 1989.
IPR2013-00517 # 29, Gololobov et al., "Recent Advances in the Staudinger Reaction", Tetrahedron, vol. 48, No. 8, 1992, 1353-1406.
IPR2013-00517 # 30, "Second Declaration of Dr. Bruce Branchaud in Support of Intelligent Bio-Systems, Inc.'s Reply to Illumina's Patent Owner Response", Jul. 28, 2014.
IPR2013-00517 # 31, Hyman, "US Patent No. 5,602,000", Feb. 11, 1997.
IPR2013-00517 # 32, Chen, "DNA polymerases drive DNA sequencing-by-synthesis technologies: both past and present", Frontiers in Microbiology, Review Article, Jun. 24, 2014.
IPR2013-00517 # 33, Chang et al., "Molecular Biology of Terminal Transferase", CRC Critical Reviews in Biochemistry, vol. 21, Issue 1, Jul. 28, 2014, 27- 52.
IPR2013-00517 # 34, Mag et al., "Synthesis and selective cleavage of oligodeoxyribonucleotides containing non-chiral internucleotide phosphoramidate linkages", Nucleic Acids Research, vol. 17, No. 15, 1989.

(56) References Cited

OTHER PUBLICATIONS

IPR2013-00517 # 35, Laidler et al., "Chemical Kinetics, Third Edition", 1987, 10-11.
IPR2013-00517 # 36, "Park IP Translations", Jun. 30, 2014.
IPR2013-00517 # 37, Knouzi et al., "English Translation", Aug. 2, 1985.
IPR2013-00517 # 38, Knouzi et al., "Reduction d'azides par la triphenylphosphine en presence d'eau: une methode generale et chimioselective d'acces auz amines primaires", Feb. 8, 1985, 815-819.
IPR2013-00517 # 39, Smith et al., "US Patent Application Publication No. 2006/0240439", Oct. 26, 2006.
IPR2013-00517 # 40, Bentley, "Supplemental Information", Nature, doi: 10.1038/nature07517, Jul. 28, 2014.
IPR2013-00517 # 41, Kirby, "A New Method for the Isolation of Deoxyribonucleic Acids: Evidence on the Nature of Bonds between Deoxyribonucleic Acid and Protein", Renal Clearance of 17-oxo Steroid Conjugates, vol. 66, 1957, 495-504.
IPR2013-00517 # 42, Efimov et al., "An Azidomethyl Protective Group in the Synthesis of Oligoribonucleotides by the Phosphotriester Method", Letters to the Editor, Russian Journal of Bioorganic Chemistry, vol. 35, No. 2, 2009, 250-253.
IPR2013-00517 # 43, Levine et al., "The Relationship of Structure to the Effectiveness of Denaturing Agents for Deoxyribonucleic Acid", Biochemistry, vol. 2, No. 1, Jan.-Feb. 1963, 168-175.
1PR2013-00517 # 44, Leberton et al., "Structure-Immunosuppressive Activity Relationships of New Analogues of 15-Deoxysperqualin. 2. Structural Modifications of the Spermidine Moiety", J. Med. Chem. 42, 1999, 4749-4763.
IPR2013-00517 # 45, "Declaration of Dr. Michael Metzker in Support of Intelligent Bio-Systems, Inc.'s Reply to Illumina's Patent Owner Response", Jul. 28, 2014.
IPR2013-00517 # 46, "Petitioner Intelligent Bio-Systems, Inc.'s Motion to Seal Under 37 C.F.R. 42.54", Jul. 28, 2014.
IPR2013-00517 # 47, "Intelligent Bio-System, Inc.'s Current Exhibit List Under 37 C.F.R., 42.63", Jul. 28, 2014.
IPR2013-00517 # 48, "Petitioner Intelligent Bio-Systems' Reply to Illumina's Patent Owner Response", Jul. 28, 2014.
IPR2013-00517 # 49, "Order Conduct of the Proceeding", Jul. 29, 2014.
IPR2013-00517 # 50, "Illumina Notice of Cross-Examination Deposition of IBS Declarant Dr. Michael L. Metzker", Aug. 1, 2014.
IPR2013-00517 # 51, "Illumina Notice of Cross-Examination Deposition of IBS Declarant Dr. Bruce P. Branchaud", Aug. 12, 2014.
IPR2013-00517 # 52, "Patent Owner's email for request for Authorization to File IBS v Illumina", Aug. 20, 2014.
IPR2013-00517 # 53, "Intelligent Bio-System's Objections to Illumina's Exhibits Marked at Dr. Branchaud's Deposition", Sep. 2, 2014.
IPR2013-00517 # 54, "Intelligent Bio-System's Objections to Illumina's Exhibits Marked at Dr. Metzker's Deposition", Aug. 19, 2014.
IPR2013-00517 # 55, "Intelligent Bio-System's Objections to Illumina's Exhibits Submitted with its Patent Owner Response", May 19, 2014.
IPR2013-00517 # 56, "Intelligent Bio-System, Inc.'s Current Exhibit List Under 37 C.F.R., 42.63", Sep. 2, 2014.
IPR2013-00517 # 57, "Petitioner Intelligent Bio-Systems, Inc.'s Request for Oral Argument", Sep. 2, 2014.
IPR2013-00517 # 58, "Petitioner Intelligent Bio-Systems, Inc.'s Motion to Exclude Evidence", Sep. 2, 2014.
IPR2013-00517 # 59, "Illumina's Motion for Observations on the Cross-Examination Testimony of Bruce Branchaud, Ph.D. and Michael Metzker, Ph.D.", Sep. 2, 2014.
IPR2013-00517 # 60, "Illumina Motion to Seal Under 37 C.F.R. 42.54", Sep. 2, 2014.
IPR2013-00517 # 61, "Illumina's Motion to Exclude evidence Pursuant to 37 C.R.F., 42.64(c)", Sep. 2, 2014.
IPR2013-00517 # 62, "Illumina Request for Oral Argument", Sep. 2, 2014.
IPR2013-00517 # 63, "Illumina Updated Exhibit List", Sep. 2, 2014.
IPR2013-00517 # 64, "Videotaped sworn testimony of Bruce P. Branchaud, Ph.D.", Sep. 2, 2014.
IPR2013-00517 # 65, "Videotaped Deposition of Michael L. Metzker, Ph.D.", Aug. 12, 2014.
IPR2013-00517 # 66, "Illumina Objections to Admissibility of IBS Evidence Served With Reply", Aug. 4, 2014.
IPR2013-00517 # 67, Reardon et al., "Reduction of 3'-Azido-3-deoxythymidine (AZT) and AZT Nucleotides by Thiols", The Journal of Biological Chemistry, vol. 269, No. 23, Jun. 10, 1994, 15999-16008.
IPR2013-00517 # 68, Sebastian et al., "Dendrimers With N,N-Disubstituted Hydrazines as End Groups, Useful Precursors for the Synthesis of Water-Soluble Dendrimers Capped With Carbohydrate, Carboxylic or Boronic Acid Derivatives", Tetrahedron 56, 2000, 6269-6277.
IPR2013-00517 # 69, Aldrich, "Fine Chemicals", Aldrich Chemical Company, Inc, 1986.
IPR2013-00517 # 70, Wu et al., "Termination of DNA synthesis by N6- alkylated, not 3'-0- alkylated, photocleavable 2'-deoxyadenosine triphosphates", Nucleic Acids Research, vol. 35, No. 19, 2007, 6339-6349.
IPR2013-00517 # 71, "Initial sequencing and analysis of the human genome", Nature, vol. 409, 2001, 850-921.
IPR2013-00517 # 72, Gardner et al., "Rapid incorporation kinetics and improved fidelity of a novel class of 3'-OH unblocked reversible terminators", Nucleic Acids Research, vol. 40, No. 15, May 8, 2012, 7404-7415.
IPR2013-00517 # 73, Mussini et al., "Criteria for Standardization of pH Measurements in Organic Solvents and Water + Organic Solvent Mixtures of Moderate to High Permittivities", Pure & Appl. Chem., vol. 57, No. 6, 1985, 865-876.
IPR2013-00517 # 74, O'Neil, et al., "The Merck Index, An Encyclopedia of Chemicals, Drugs, and Biologicals, Thirteenth Edition", 2001.
IPR2013-00517 # 75, Metzker, "US Publication No. 2003/0180769", Sep. 25, 2003.
IPR2013-00517 # 76, Hanlon, "The importance of London dispersion forces in the maintenance of the deoxyribonuleic acid helix", Biochemical and Biophysical Research Communications, vol. 23, No. 6, 1966.
IPR2013-00517 # 77, Treinin, "General and theoretical aspects, Chapter I, The Chemistry of the Azido Group, Edited by Saul Patai", 1971.
IPR2013-00517 # 78, Tsai et al., "Versatile and Efficient Synthesis of a New Class of Aza-Based Phosphinic Amide Ligands via Unusual P-C Cleavage", Helvetica Chimica Acta, vol. 89, 2006, 3007-3017.
IPR2013-00517 # 79, Metzker, "Sequencing technologies- the next generation", Nature Reviews, Genetics, vol. 11, Jan. 2010, 31-46.
IPR2013-00517 # 80, "Intelligent Bio-Systems, Inc.'s Opposition to Illumina's Motion to Exclude Evidence", Sep. 15, 2014.
IPR2013-00517 # 81, "IBS's response to Illumina's motion for observations on the cross-examination testimony of Bruce Branchaud, Ph.D., and Michael Metzker, Ph.D.", Sep. 15, 2014.
IPR2013-00517 # 82, "Answer and Counterclaims of Defendant Intelligent Bio-Systems, Inc.", Sep. 18, 2013.
IPR2013-00517 # 83, "Declaration of Rosalyn M. Espejo Regarding Fed.R. Evid. 902(11) Certification of Records", Jun. 2, 2014.
IPR2013-00517 # 84, "Illumina Updated Exhibit List", Sep. 15, 2014.
IPR2013-00517 # 85, "Illumina's Opposition to IBS Motion to Exclude Evidence", Sep. 15, 2014.
IPR2013-00517 # 86, "Illumina Motion to Seal Under 37 C.F.R. 42.54", Sep. 15, 2014.
IPR2013-00517 # 86, "Order, Trial Hearing", Sep. 17, 2014.
IPR2013-00517 # 88, "Illumina's Reply to IBS's Opposition to Illumina's Motion to Exclude", Sep. 22, 2014.
IPR2013-00517 # 89, "Emails re IBS withdrawing its hearsay objections", Jul. 31, 2014.
IPR2013-00517 # 90, "Errata Sheet for Bruce Branchaud, Ph.D. Deposition", Taken: Aug. 26, 2014.
IPR2013-00517 # 91, "Errata Sheet for Michael L. Metzker, Ph.D. Deposition", Taken: Aug. 12, 2014.

(56) References Cited

OTHER PUBLICATIONS

IPR2013-00517 # 92, "Petitioner Intelligent Bio-Systems, Inc.'s Reply to Illumina's Opposition to Intelligent Bio-Systems, Inc.'s Motion to Exclude Evidence", Sep. 22, 2014.
IPR2013-00517 # 93, "Intelligent Bio-System, Inc.'s Current Exhibit List Under 37 C.F.R. 42.63", Sep. 22, 2014.
IPR2013-00517 # 94, Judge Lora M. Green et al., "Illumina's Demonstratives for Oral Hearing", Oct. 10, 2014.
IPR2013-00517 # 95, "Illumina Updated Exhibit List", Oct. 3, 2014.
IPR2013-00517 # 96, "Illumina Notice of Filing and Serving Its Demonstratives (Ex. 2156) for Oral Argument", Oct. 3, 2014.
IPR2013-00517 # 97, "Illumina Additional Power of Attorney for Jeff Costakos", Oct. 3, 2014.
IPR2013-00517 # 98, "Illumina Updated mandatory Notice Adding Jeffrey N. Costakos as Additional Backup Counsel", Oct. 3, 2014.
IPR2013-00517 # 99, Judge Lora M. Green et al., "Demonstrative Exhibits of Intelligent Bio-Systems, Inc. for Oral Hearing", Oct. 10, 2014.
IPR2013-00517 # 100, "Intelligent Bio-System, Inc.'s Notice of Filing Its Demonstratives (Ex. 1062) for Oct. 10, 2014 Oral Argument", Oct. 3, 2014.
IPR2013-00517 # 101, "Intelligent Bio-System, Inc.'s Current Exhibit List Under 37 C.F.R. 42.63", Oct. 3, 2014.
IPR2013-00517 # 102, Intelligent Bio-Systems, Inc.'S Answer, Affirmative Defenses & Counterclaims to Illumina, Inc. and Illumina Cambridge Ltd.'S Second Amended Counterclaims to Amended Complaint, dated Jan. 7, 2013.
IPR2013-00517 # 103, "Dae H. Kim Thesis Proposal Presentation", dated Jun. 28, 2007.
IPR2013-00517 # 104, "Draft to Cao article", dated Sep. 18, 2008.
IPR2013-00517 # 105, "Email chain from Jerzy Olejnik to Andrew Gardner", dated Oct. 2, 2007.
IPR2013-00517 # 106, "Email Chain from Jerzy Olejnik to z179", dated Jun. 29, 2007.
IPR2013-00517 # 107, "Email chain from Jerzy Olenik to hc228 and Shiv Kumar", dated Feb. 1, 2008.
IPR2013-00517 # 108, "Email chain from Jerzy Olenik to msm2137", dated Jun. 3, 2007.
IPR2013-00517 # 109, "Email chain from Jim Russo to hc2278, Jia guo, Dae Kim, 1x2109, Zengmin Li, qm6, ly2141, Jingyue Ju, Christine Rupp, Petra Lee Forde, Irina Morozova and John Edwards", dated Nov. 4, 2007.
IPR2013-00517 # 109, "Email chain from Steven Gordon to Jingyue Ju", dated Oct. 29, 2007.
IPR2013-00517 # 110, "Email chain from Steven Gordon to Jeffrey Arnold", dated Jun. 3, 2007.
IPR2013-00517 # 112, "Email from Bert Vogelstein to jre, Devin, jw2231, Jingyue Ju, Nickolas Papadopoulos and K8", dated Mar. 11, 2008.
IPR2013-00517 # 113, "Email from Bert Vogelstein to mysworld1982, dj222 and jre13", dated Mar. 3, 2008.
IPR2013-00517 # 114, "Email from Huanyan Cao to Huanyan Cao, Jerzy Olejnik, Mong Sano Marma, Waldemar Szczepanik and Wojciech Czardybon", dated Mar. 4, 2009.
IPR2013-00517 # 115, "Email from Jerzay Olejnik to Evan Guggenheim, Visa Visalakshi, Selase Metewo Enuameh, Mong Sano Marma, Huanyan Cao, Lei O'Malley and Alisha Perelta", dated Nov. 11, 2008.
IPR2013-00517 # 116, "Email from Jerzy Olejnik to Stephen Buchwald and Steven Gordon", dated Aug. 10, 2007.
IPR2013-00517 # 117, "Email from Jingyue Ju to Jingue Ju and Christine Rupp", dated Jun. 5, 2008.
IPR2013-00517 # 118, "Email from msm2137 to Jingyue Ju", dated Mar. 8, 2007.
IPR2013-00517 # 119, "Email from Shiv Kumar to Jerzy Olejnik and Jinguyue Ju", dated Jul. 5, 2012.
IPR2013-00517 # 120, "Intelligent Bio-Systems, Inc., Cleavage", dated Aug. 2009.
IPR2013-00517 # 121, "Intelligent Bio-Systems, Inc., Custom Synthesis of Nucleotide Analogs", dated Aug. 1, 2012.
IPR2013-00517 # 122, "Intelligent Bio-Systems, Inc., Custom Synthesis of Nucleotide Analogs", dated May 6, 2008.
IPR2013-00517 # 123, "Intelligent Bio-Systems, Inc., Nucleotides", dated Jun. 15, 2011.
IPR2013-00517 # 124, "Inter Partes Review—Petitioner Power of Attorney", dated Apr. 4, 2014.
IPR2013-00517 # 125, "Invention Disclosure Form", dated Aug. 17, 2007.
IPR2013-00517 # 126, "Ju Lab Thesis Proposal", dated Mar. 19, 2007.
IPR2013-00517 # 127, "Ju Proposal", dated Nov. 6, 2007.
IPR2013-00517 # 128, "Ju Proposal", dated Nov. 29, 2006.
IPR2013-00517 # 129, "Lin Yu 3rd Year Research Presentation", dated May 2, 2008.
IPR2013-00517 # 130, "Note regarding Ju's Chemistry", dated May 5, 2014.
IPR2013-00517 # 131, "Research Plan", dated Feb. 2, 2006.
IPR2013-00518 # 1, "Judgment, Request for Adverse Judgment", May 6, 2014.
Greene, et al., "Protective Groups in Organic Synthesis", John Willey & Sons, New York, 1999, 1-316.
IPR2013-00128, "Excerpts from the '026 file history", 2004-2005.
IPR2013-00517, "Final Written Decision", dated Feb. 11, 2015.
IPR2013-00517, "Record of Oral Hearing held Friday, Oct. 10, 2014", dated Feb. 2, 2015.

* cited by examiner

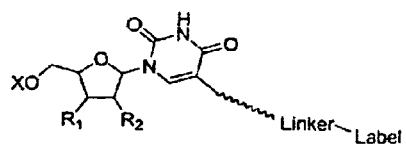

Uridine C5-linker

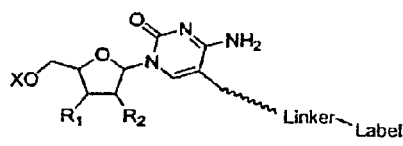

Cytidine C5-linker

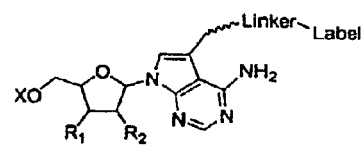

N7 Deazaadenosine C7-linker

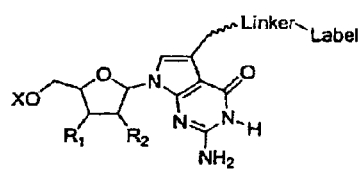

N7 Deazaguanosine C7-linker

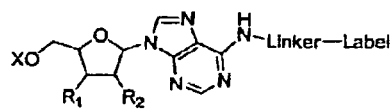

Adenosine N6-linker

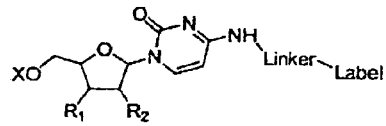

Cytidine N4-linker where $R_1$ and $R_2$, which may be the same or different, are each selected from H, OH, or any group which can be transformed into an OH. Suitable groups for $R_1$ and $R_2$ are described in Figure 3

X = H, phosphate, diphosphate or triphosphate

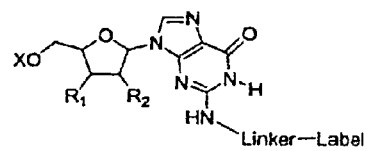

Guanosine N2-linker

Fig. 1

Protected hemiacetals:
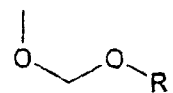
Protected hemithioacetals:
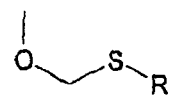
Protected hemiaminals:
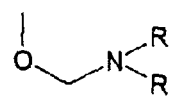
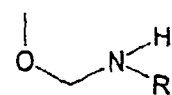
Fig. 4

MODIFIED NUCLEOTIDES

This application is a divisional application of U.S. patent application Ser. No. 13/281,275, filed Oct. 25, 2011, which is a divisional application of U.S. patent application Ser. No. 12/804,352, filed Jul. 20, 2010, now U.S. Pat. No. 8,071,739, which is a divisional application of U.S. patent application Ser. No. 12/455,397, filed Jun. 1, 2009, now U.S. Pat. No. 7,771,973, which is a divisional application of U.S. patent application Ser. No. 10/525,401, filed Jun. 1, 2006, now U.S. Pat. No. 7,541,444, which is a 371 National Stage Application of PCT Patent Application No. PCT/GB2003/003686, filed Aug. 22, 2003, which claims priority to Great Britain Patent Application No. 0303924.5, filed Feb. 20, 2003, Great Britain Patent Application No. 0230037.4, filed Dec. 23, 2002, and which is a continuation-in-part of U.S. patent application Ser. No. 10/227,131, filed Aug. 23, 2002, now U.S. Pat. No. 7,057,026, the contents of each of which are incorporated by reference herein in their entireties.

The invention relates to modified nucleotides. In particular, this invention discloses nucleotides having a removable protecting group, their use in polynucleotide sequencing methods and a method for chemical deprotection of the protecting group.

Advances in the study of molecules have been led, in part, by improvement in technologies used to characterise the molecules or their biological reactions. In particular, the study of the nucleic acids DNA and RNA has benefited from developing technologies used for sequence analysis and the study of hybridisation events.

An example of the technologies that have improved the study of nucleic acids is the development of fabricated arrays of immobilised nucleic acids. These arrays consist typically of a high-density matrix of polynucleotides immobilised onto a solid support material. See, e.g., Fodor et al., *Trends Biotech.* 12:19-26, 1994, which describes ways of assembling the nucleic acids using a chemically sensitized glass surface protected by a mask, but exposed at defined areas to allow attachment of suitably modified nucleotide phosphoramidites. Fabricated arrays can also be manufactured by the technique of "spotting" known polynucleotides onto a solid support at predetermined positions (e.g., Stimpson et al., *Proc. Natl. Acad. Sci. USA* 92:6379-6383, 1995).

Sequencing by synthesis of DNA ideally requires the controlled (i.e. one at a time) incorporation of the correct complementary nucleotide opposite the oligonucleotide being sequenced. This allows for accurate sequencing by adding nucleotides in multiple cycles as each nucleotide residue is sequenced one at a time, thus preventing an uncontrolled series of incorporations occurring. The incorporated nucleotide is read using an appropriate label attached thereto before removal of the label moiety and the subsequent next round of sequencing. In order to ensure only a single incorporation occurs, a structural modification ("blocking group") of the sequencing nucleotides is required to ensure a single nucleotide incorporation but which then prevents any further nucleotide incorporation into the polynucleotide chain. The blocking group must then be removable, under reaction conditions which do not interfere with the integrity of the DNA being sequenced. The sequencing cycle can then continue with the incorporation of the next blocked, labelled nucleotide. In order to be of practical use, the entire process should consist of high yielding, highly specific chemical and enzymatic steps to facilitate multiple cycles of sequencing.

To be useful in DNA sequencing, nucleotide, and more usually nucleotide triphosphates, generally require a 3'OH-blocking group so as to prevent the polymerase used to incorporate it into a polynucleotide chain from continuing to replicate once the base on the nucleotide is added. There are many limitations on the suitability of a molecule as a blocking group. It must be such that it prevents additional nucleotide molecules from being added to the polynucleotide chain whilst simultaneously being easily removable from the sugar moiety without causing damage to the polynucleotide chain. Furthermore, the modified nucleotide must be tolerated by the polymerase or other appropriate enzyme used to incorporate it into the polynucleotide chain. The ideal blocking group will therefore exhibit long term stability, be efficiently incorporated by the polymerase enzyme, cause total blocking of secondary or further incorporation and have the ability to be removed under mild conditions that do not cause damage to the polynucleotide structure, preferably under aqueous conditions. These stringent requirements are formidable obstacles to the design and synthesis of the requisite modified nucleotides.

Reversible blocking groups for this purpose have been described previously but none of them generally meet the above criteria for polynucleotide, e.g. DNA-compatible, chemistry.

Metzker et al., (*Nucleic Acids Research*, 22(20): 4259-4267, 1994) discloses the synthesis and use of eight 3'-modified 2-deoxyribonucleoside 5'-triphosphates (3'-modified dNTPs) and testing in two DNA template assays for incorporation activity. The 3'-modified dNTPs included 3'allyl deoxyriboadenosine 5'-triphosphate (3'-allyl dATP). However, the 3'allyl blocked compound was not used to demonstrate a complete cycle of termination, deprotection and reinitiation of DNA synthesis: the only test results presented were those which showed the ability of this compound to terminate DNA synthesis in a single termination assay, out of eight such assays conducted, each conducted with a different DNA polymerase.

WO02/29003 (The Trustees of Columbia University in the City of New York) describes a sequencing method which, may include the use of an allyl protecting group to cap the 3'-OH group on a growing strand of DNA in a polymerase reaction. The allyl group is introduced according to the procedure of Metzker (infra) and is said to be removed by using methodology reported by Kamal et al (*Tet. Let,* 40, 371-372, 1999).

The Kamal deprotection methodology employs sodium iodide and chlorotrimethylsilane so as to generate in situ iodotrimethylsilane, in acetonitrile solvent, quenching with sodium thiosulfate. After extraction into ethyl acetate and drying (sodium sulfate), then concentration under reduced pressure and column chromatography (ethyl acetate:hexane; 2:3 as eluant), free alcohols were obtained in 90-98% yield.

In WO02/29003, the Kamal allyl deprotection is suggested as being directly applicable in DNA sequencing without modification, the Kamal conditions being mild and specific.

While Metzker reports on the preparation of a 3'allyl-blocked nucleotide or nucleoside and WO02/29003 suggests the use of the allyl functionality as a 3'-OH cap during sequencing, neither of these documents actually teaches the deprotection of 3'-allylated hydroxyl group in the context of a sequencing protocol. Whilst the use of an allyl group as a hydroxyl protecting group is well known—it is easy to introduce and is stable across the whole pH range and to elevated temperatures—there is to date, no concrete embodiment of the successful cleavage of a 3'-allyl group under DNA compatible conditions, i.e. conditions under which the integrity of the DNA is not wholly or partially destroyed. In other words, it has not been possible hitherto to conduct DNA sequencing using 3'OH allyl-blocked nucleotides.

The Kamal methodology is inappropriate to conduct in aqueous media since the TMS chloride will hydrolyse preventing the in situ generation of TMS iodide. Attempts to carry out the Kamal deprotection (in acetonitrile) in sequencing have proven unsuccessful in our hands.

The present invention is based on the surprising development of a number of reversible blocking groups and methods of deprotecting them under DNA compatible conditions. Some of these blocking groups are novel per se; others have been disclosed in the prior art but, as noted above, it has not proved possible to utilised these blocking groups in DNA sequencing.

One feature of the invention derives from the development of a completely new method of allyl deprotection. Our procedure is of broad applicability to the deprotection of virtually all allyl-protected hydroxyl functionality and may be effected in aqueous solution, in contrast to the methodology of Kamal et al. (which is effected in acetonitrile) and to the other methods known generally in the prior art which are highly oxygen- and moisture-sensitive. A further feature of the invention derives from the development of a new class of protecting groups. These are based upon acetals and related protecting groups but do not suffer from some of the disadvantages of acetal deprotection known in the prior art.

The allyl deprotection methodology makes use of a water-soluble transition metal catalyst formed from a transition metal and at least partially water-soluble ligands. In aqueous solution these form at least partially water-soluble transition metal complexes. By aqueous solution herein is meant a liquid comprising at least 20 vol %, preferably at least 50%, for example at least 75 vol %, particularly at least 95 vol % and especially greater than above 98 vol %, ideally 100 vol % of water as the continuous phase.

As those skilled in the art will appreciate, the allyl group may be used to protect not only the hydroxyl group but also thiol and amine functionalities. Moreover allylic esters may be formed from the reaction between carboxylic acids and allyl halides, for example. Primary or secondary amides may also be protected using methods known in the art. The novel deprotection methodology described herein may be used in the deprotection of all these allylated compounds, e.g. allyl esters and mono- or bisallylated primary amines or allylated amides, or in the deprotection of allylated secondary amines. The method is also suitable in the deprotection of allyl esters and thioethers.

Protecting groups which comprise the acetal functionality have been used previously as blocking groups. However, removal of such groups and ethers requires strongly acidic deprotections detrimental to DNA molecules. The hydrolysis of an acetal however, results in the formation of an unstable hemiacetal intermediate which hydrolyses under aqueous conditions to the natural hydroxyl group. The inventors have utilised this concept and applied it further such that this feature of the invention resides in utilising blocking groups that include protecting groups to protect intermediate molecules that would normally hydrolyse under aqueous conditions. These protecting groups comprise a second functional group that stabilises the structure of the intermediate but which can be removed at a later stage following incorporation into the polynucleotide. Protecting groups have been used in organic synthesis reactions to temporarily mask the characteristic chemistry of a functional group because it interferes with another reaction.

Therefore, according to a first aspect of the invention there is provided a modified nucleotide or nucleoside molecule comprising a purine or pyrimidine base and a ribose or deoxyribose sugar moiety having a removable 3'-OH blocking group covalently attached thereto, such that the 3' carbon atom has attached a group of the structure

—O—Z wherein Z is any of —C(R')$_2$—O—R", —C(R')$_2$—N(R")$_2$, —C(R')$_2$—N(H)R", —C(R')$_2$—S—R" and —C(R')$_2$—F, wherein each R" is or is part of a removable protecting group;

each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group, or a detectable label attached through a linking group; or (R')$_2$ represents an alkylidene group of formula =C(R''')$_2$ wherein each R''' may be the same or different and is selected from the group comprising hydrogen and halogen atoms and alkyl groups; and wherein said molecule may be reacted to yield an intermediate in which each R" is exchanged for H or, where Z is —C(R')$_2$—F, the F is exchanged for OH, SH or NH$_2$, preferably OH, which intermediate dissociates under aqueous conditions to afford a molecule with a free 3'OH;

with the proviso that where Z is —C(R')$_2$—S—R", both R' groups are not H.

Viewed from another aspect, the invention provides a 3'-O-allyl nucleotide or nucleoside which nucleotide or nucleoside comprises a detectable label linked to the base of the nucleoside or nucleotide, preferably by a cleavable linker.

In a further aspect, the invention provides a polynucleotide comprising a 3'-O-allyl nucleotide or nucleoside which nucleotide or nucleoside comprises a detectable label linked to the base of the nucleoside or nucleotide, preferably by a cleavable linker.

Viewed from a still further aspect, the invention provides a method of converting a compound of formula R—O-allyl, R$_2$N(allyl), RNH(allyl), RN(allyl)$_2$ or R—S-allyl to a corresponding compound in which the allyl group is removed and replaced by hydrogen, said method comprising the steps of reacting a compound of formula R—O-allyl, R$_2$N(allyl), RNH(allyl), RN(allyl)$_2$ or R—S-allyl in aqueous solution with a transition metal comprising a transition metal and one or more ligands selected from the group comprising water-soluble phosphine and water-soluble nitrogen-containing phosphine ligands, wherein the or each R is a water-soluble biological molecule.

In a further aspect the invention provides a method of controlling the incorporation of a nucleotide molecule complementary to the nucleotide in a target single-stranded polynucleotide in a synthesis or sequencing reaction comprising incorporating into the growing complementary polynucleotide a molecule according to the invention, the incorporation of said molecule preventing or blocking introduction of subsequent nucleoside or nucleotide molecules into said growing complementary polynucleotide.

In a further aspect, the invention provides a method for determining the sequence of a target single-stranded polynucleotide, comprising monitoring the sequential incorporation of complementary nucleotides, wherein at least one incorporation, and preferably all of the incorporations is of a nucleotide according to the invention as hereinbefore described which preferably comprises a detectable label linked to the base of the nucleoside or nucleotide by a cleavable linker and wherein the identity of the nucleotide incorporated is determined by detecting the label, said blocking group and said label being removed prior to introduction of the next complementary nucleotide.

From a further aspect, the invention provides a method for determining the sequence of a target single-stranded polynucleotide, comprising:

(a) providing a plurality of different nucleotides according to the hereinbefore described invention which nucleotides are preferably linked from the base to a detectable label by a cleavable linker and wherein the detectable label linked to each type of nucleotide can be distinguished upon detection from the detectable label used for other types of nucleotides;

(b) incorporating the nucleotide into the complement of the target single-stranded polynucleotide;

(c) detecting the label of the nucleotide of (b), thereby determining the type of nucleotide incorporated;

(d) removing the label of the nucleotide of (b) and the blocking group; and (e) optionally repeating steps (b)-(d) one or more times;

thereby determining the sequence of a target single-stranded polynucleotide.

Additionally, in another aspect, the invention provides a kit, comprising:

(a) a plurality of different individual nucleotides of the invention; and (b) packaging materials therefor.

The nucleosides or nucleotides according to or used in the methods of the present invention comprise a purine or pyrimidine base and a ribose or deoxyribose sugar moiety which has a blocking group covalently attached thereto, preferably at the 3'O position, which renders the molecules useful in techniques requiring blocking of the 3'-OH group to prevent incorporation of additional nucleotides, such as for example in sequencing reactions, polynucleotide synthesis, nucleic acid amplification, nucleic acid hybridisation assays, single nucleotide polymorphism studies, and other such techniques.

Where the term "blocking group" is used herein in the context of the invention, this embraces both the allyl and "Z" blocking groups described herein. However, it will be appreciated that, in the methods of the invention as described and claimed herein, where mixtures of nucleotides are used, these very preferably each comprise the same type of blocking, i.e. allyl-blocked or "Z"-blocked. Where "Z"-blocked nucleotides are used, each "Z" group will generally be the same group, except in those cases where the detectable label forms part of the "Z" group, i.e. is not attached to the base.

Once the blocking group has been removed, it is possible to incorporate another nucleotide to the free 3'-OH group.

The molecule can be linked via the base to a detectable label by a desirable linker, which label may be a fluorophore, for example. The detectable label may instead, if desirable, be incorporated into the blocking groups of formula "Z". The linker can be acid labile, photolabile or contain a disulfide linkage. Other linkages, in particular phosphine-cleavable azide-containing linkers, may be employed in the invention as described in greater detail.

Preferred labels and linkages included those disclosed in WO 03/048387.

In the methods where nucleotides are incorporated, e.g. where the incorporation of a nucleotide molecule complementary to the nucleotide in a target single stranded polynucleotide is controlled in a synthesis or sequencing reaction of the invention, the incorporation of the molecule may be accomplished via a terminal transferase, a polymerase or a reverse transcriptase.

Preferably, the molecule is incorporated by a polymerase and particularly from *Thermococcus* sp., such as 9°N. Even more preferably, the polymerase is a mutant 9°N A485L and even more preferably is a double mutant Y409V and A485L.

In the methods for determining the sequence of a target single-stranded polynucleotide comprising monitoring the sequential incorporation of complementary nucleotides of the invention, it is preferred that the blocking group and the label may be removed in a single chemical treatment step. Thus, in a preferred embodiment of the invention, the blocking group is cleaved simultaneously with the label. This will of course be a feature inherent to those blocking groups of formula Z which incorporate a detectable label.

Furthermore, preferably the blocked and labelled modified nucleotide constructs of the nucleotide bases A, T, C and G are recognised as substrates by the same polymerase enzyme.

In the methods described herein, each of the nucleotides can be brought into contact with the target sequentially, with removal of non-incorporated nucleotides prior to addition of the next nucleotide, where detection and removal of the label and the blocking group is carried out either after addition of each nucleotide, or after addition of all four nucleotides.

In the methods, all of the nucleotides can be brought into contact with the target simultaneously, i.e., a composition comprising all of the different nucleotides is brought into contact with the target, and non-incorporated nucleotides are removed prior to detection and subsequent to removal of the label and the blocking group.

The methods can comprise a first step and a second step, where in the first step, a first composition comprising two of the four types of modified nucleotides is brought into contact with the target, and non-incorporated nucleotides are removed prior to detection and subsequent to removal of the label and the blocking group, and where in the second step, a second composition comprising the two nucleotides not included in the first composition is brought into contact with the target, and non-incorporated nucleotides are removed prior to detection and subsequent to removal of the label and blocking group, and where the first steps and the second step can be optionally repeated one or more times.

The methods described herein can also comprise a first step and a second step, where in the first step, a composition comprising one of the four nucleotides is brought into contact with the target, and non-incorporated nucleotides are removed prior to detection and subsequent to removal of the label and blocking group, and where in the second step, a second composition, comprising the three nucleotides not included in the first composition is brought into contact with the target, and non-incorporated nucleotides are removed prior to detection and subsequent to removal of the label and blocking group, and where the first steps and the second step can be optionally repeated one or more times.

The methods described herein can also comprise a first step and a second step, where in the first step, a first composition comprising three of the four nucleotides is brought into contact with the target, and non-incorporated nucleotides are removed prior to detection and subsequent to removal of the label and blocking group and where in the second step, a composition comprising the nucleotide not included in the first composition is brought into contact with the target, and non-incorporated nucleotides are removed prior to detection and subsequent to removal of the label and blocking group, and where the first steps and the second step can be optionally repeated one or more times.

The incorporating step in the methods of the invention can be accomplished via a terminal transferase, a polymerase or a reverse transcriptase as hereinbefore defined. The detectable label and/or the cleavable linker can be of a size sufficient to prevent the incorporation of a second nucleotide or nucleoside into the nucleic acid molecule.

In certain methods described herein for determining the sequence of a target single-stranded polynucleotide, each of the four nucleotides, one of which will be complementary to the first unpaired base in the target polynucleotide, can be brought into contact with the target sequentially, optionally with removal of non-incorporated nucleotides prior to addition of the next nucleotide. Determination of the success of the incorporation may be carried out either after provision of each nucleotide, or after the addition of all of the nucleotides added. If it is determined after addition of fewer than four nucleotides that one has been incorporated, it is not necessary to provide further nucleotides in order to detect the nucleotides complementary to the incorporated nucleotide.

Alternatively, all of the nucleotides can be brought into contact with the target simultaneously, i.e., a composition comprising all of the different nucleotide (i.e. A, T, C and G or A, U, C and G) is brought into contact with the target, and non-incorporated nucleotides removed prior to detection and removal of the label(s). The methods involving sequential addition of nucleotides may comprise a first substep and optionally one or more subsequent substeps. In the first substep a composition comprising one, two or three of the four possible nucleotides is provided, i.e. brought into contact with, the target. Thereafter any unincorporated nucleotides may be removed and a detecting step may be conducted to determine whether one of the nucleotides has been incorporated. If one has been incorporated, the cleavage of the linker may be effected. In this way the identity of a nucleotide in the target polynucleotide may be determined. The nascent polynucleotide may then be extended to determine the identity of the next unpaired nucleotide in the target oligonucleotide.

If the first substep above does not lead to incorporation of a nucleotide, or if this is not known, since the presence of incorporated nucleotides is not sought immediately after the first substep, one or more subsequent substeps may be conducted in which some or all of those nucleotides not provided in the first substep are provided either, as appropriate, simultaneously or subsequently. Thereafter any unincorporated nucleotides may be removed and a detecting step conducted to determine whether one of the classes of nucleotide has been incorporated. If one has been incorporated, cleavage of the linker may be effected. In this way the identity of a nucleotide in the target polynucleotide may be determined. The nascent polynucleotide may then be extended to determine the identity of the next unpaired nucleotide in the target oligonucleotide. If necessary, a third and optionally a fourth substep may be effected in a similar manner to the second substep. Obviously, once four substeps have been effected, all four possible nucleotides will have been provided and one will have been incorporated.

It is desirable to determine whether a type or class of nucleotide has been incorporated after any particular combination comprising one, two or three nucleotides has been provided. In this way the unnecessary cost and time expended in providing the other nucleotide(s) is obviated. This is not a required feature of the invention, however.

It is also desirable, where the method for sequencing comprises one or more substeps, to remove any unincorporated nucleotides before further nucleotide are provided. Again, this is not a required feature of the invention. Obviously, it is necessary that at least some and preferably as many as practicable of the unincorporated nucleotides are removed prior to the detection of the incorporated nucleotide.

The kits of the invention include: (a) individual nucleotides according to the hereinbefore described invention, where each nucleotide has a base that is linked to a detectable label via a cleavable linker, or a detectable label linked via an optionally cleavable liner to a blocking group of formula Z, and where the detectable label linked to each nucleotide can be distinguished upon detection from the detectable label used for other three nucleotides; and (b) packaging materials therefor. The kit can further include an enzyme for incorporating the nucleotide into the complementary nucleotide chain and buffers appropriate for the action of the enzyme in addition to appropriate chemicals for removal of the blocking group and the detectable label, which can preferably be removed by the same chemical treatment step.

The nucleotides/nucleosides are suitable for use in many different DNA-based methodologies, including DNA synthesis and DNA sequencing protocols.

The invention may be understood with reference to the attached drawings in which:

FIG. 1 shows exemplary nucleotide structures useful in the invention. For each structure, X can be H, phosphate, diphosphate or triphosphate. $R_1$ and $R_2$ can be the same or different, and can be selected from H, OH, or any group which can be transformed into an OH, including, but not limited to, a carbonyl. Some suitable functional groups for $R_1$ and $R_2$ include the structures shown in FIG. 3 and FIG. 4.

FIG. 2 shows structures of linkers useful in certain aspects of the invention, including (1) disulfide linkers and acid labile linkers, (2) dialkoxybenzyl linkers, (3) Sieber linkers, (4) indole linkers and (5) t-butyl Sieber linkers.

FIG. 3 shows some functional molecules useful in the invention, including some cleavable linkers and some suitable hydroxyl protecting groups. In these structures, $R_1$ and $R_2$ may be the same of different, and can be H, OH, or any group which can be transformed into an OH group, including a carbonyl. $R_3$ represents one or more substituents independently selected from alkyl, alkoxyl, amino or halogen groups. $R_4$ and $R_5$ can be H or alkyl, and $R_6$ can be alkyl, cycloalkyl, alkenyl, cycloalkenyl or benzyl. X can be H, phosphate, diphosphate or triphosphate.

FIG. 4 is a schematic illustration of some of the Z blocking groups that can be used according to the invention.

Figure 2:
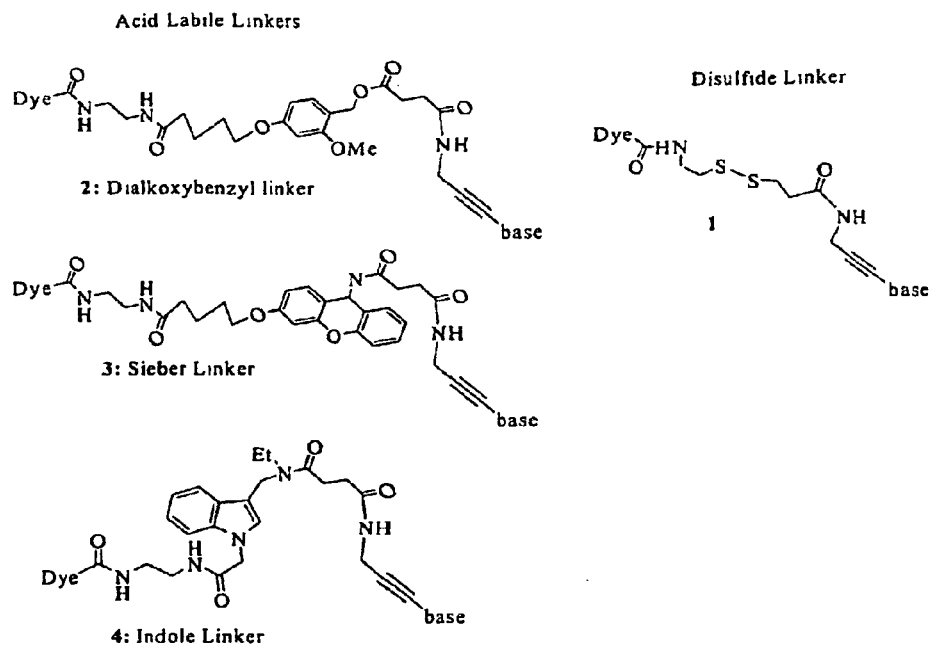

The present invention relates to nucleotide or nucleoside molecules that are modified by the reversible covalent attachment of a 3'-OH blocking groups thereto, and which molecules may be used in reactions where blocked nucleotide or nucleoside molecules are required, such as in sequencing reactions, polynucleotide synthesis and the like.

Where the blocking group is an allyl group, it may be introduced into the 3'-position using standard literature procedures such as that used by Metzker (infra).

The allyl groups are removed by reacting in aqueous solution a compound of formula R—O-allyl, $R_2$N(allyl), RNH(allyl), RN(allyl)$_2$ or R—S-allyl (wherein R is a water-soluble biological molecule) with a transition metal, wherein said transition metal is capable of forming a metal allyl complex, in the presence of one or more ligands selected from the group comprising water-soluble phosphine and water-soluble mixed nitrogen-phosphine ligands.

The water-soluble biological molecule is not particularly restricted provided, of course, it contains one or more hydroxyl, acid, amino, amide or thiol functionalities protected with an allyl group. Allyl esters are examples of compounds of formula R—O-allyl. Preferred functionalities are hydroxyl and amino.

As used herein the term biological molecule is used to embrace any molecules or class of Molecule which performs a biological role. Such molecules include for example, polynucleotides such as DNA and RNA, oligonucleotides and single nucleotides. In addition, peptides and peptide mimetics, such as enzymes and hormones etc., are embraced by the invention. Compounds which comprise a secondary amide linkage, such as peptides, or a secondary amine, where such compounds are allylated on the nitrogen atom of the secondary amine or amide, are examples of compounds of formula $R_2N(allyl)$ in which both R groups belong to the same biological molecule. Particularly preferred compounds however are polynucleotides, (including oligonucleotides) and nucleotides and nucleosides, preferably those which contain one base to which is attached a detectable label linked through a cleavable linker. Such compounds are useful in the determination of sequences of oligonucleotides as described herein.

Transition metals of use in the invention are any which may form metal allyl complexes, for example platinum, palladium, rhodium, ruthenium, osmium and iridium. Palladium is preferred.

The transition metal, e.g. palladium, is conveniently introduced as a salt, e.g. as a halide. Mixed salts such as $Na_2PdCl_4$ may also be used. Other appropriate salts and compounds will be readily determined by the skilled person and are commercially available, e.g. from Aldrich Chemical Company.

Suitable ligands are any phosphine or mixed nitrogen-phosphine ligands known to those skilled in the art, characterised in that the ligands are derivatised so as to render them water-soluble, e.g. by introducing one or more sulfonate, amine, hydroxyl (preferably a plurality of hydroxyl) or carboxylate residues. Where amine residues are present, formation of amine salts may assist the soublisation of the ligand and thus the metal-allyl complex. Examples of appropriate ligands are triaryl phosphines, e.g. triphenyl phosphine, derivatised so as to make them water-soluble. Also preferred are trialkyl phosphines, e.g. tri-$C_{1-6}$-alkyl phosphines such as triethyl phosphines; such trialkyl phosphines are likewise derivatised so as to make them water-soluble. Sulfonate-containing and carboxylate-containing phosphines are particularly preferred; an example of the former 3,3',3"-phosphinidynetris(benzenesulfonic acid) which is commercially available from Aldrich Chemical Company as the trisodium salt; and a preferred example of the latter is tris(2-carboxyethyl)phosphine which is available from Aldrich as the hydrochloride salt.

The derivatised water-soluble phosphines and nitrogen-containing phosphines described herein may be used as their salts (e.g. as the hydrochloride or sodium salts) or, for example, in the case of the sulfonic and carboxylic acid-containing phosphines described herein, as the free acids. Thus 3,3',3"-phosphinidynetris(benzenesulfonic acid) and tris(2-carboxyethyl)phosphines may be introduced either as the triacids or the trisodium salts. Other appropriate salts will be evident to those skilled in the art. The existence in salt form is not particularly important provided the phosphines are soluble in aqueous solution.

Other ligands which may be used to include the following:

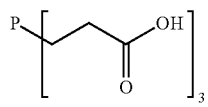

as the hydrochloride salt, neutral compound and the trisodium salt

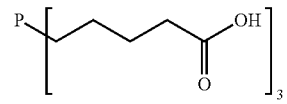

as the hydrochloride salt, neutral compound and the trisodium salt

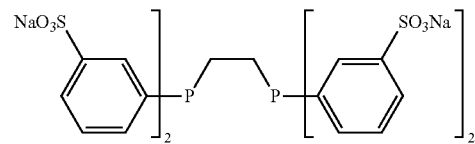

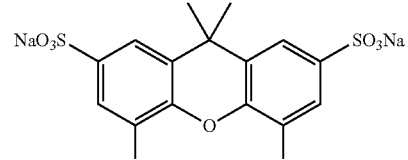

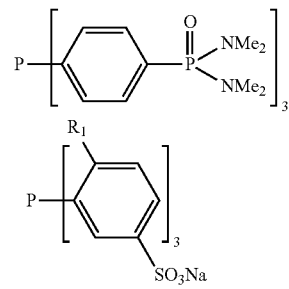

R1 = OMe, CO2H, CO2Na

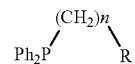

n = 1-5
R = PO3Na2,
CO2Na,
SO3Na,
OH

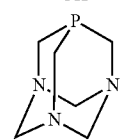

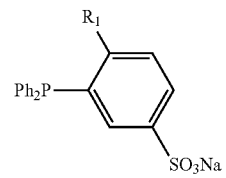

R1 = OMe, CO2H, CO2Na

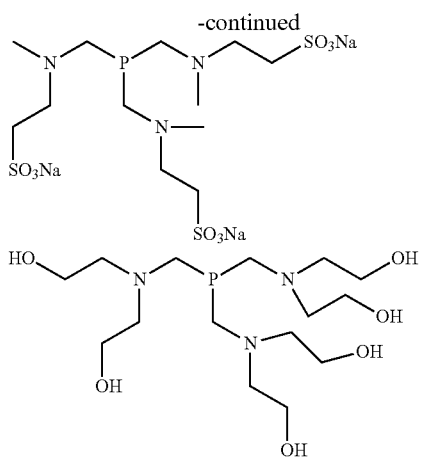

The skilled person will be aware that the atoms chelated to the transition metal in the water soluble complex may be part of mono- or polydentate ligands. Some such polydentate ligands are shown above. Whilst monodentate ligands are preferred, the invention thus also embraces methods which use water-soluble bi-, tri-, tetra-, penta- and hexadentate water-soluble phosphine and water-soluble nitrogen-containing phosphine ligands The various aspects of the invention relating to allyl blocking groups are of particular utility in sequencing polynucleotides wherein the 3'-OH is allylated. However, when present, the 2'-OH is equally amenable to allylation, and to deprotection according to the method of the invention if necessary. In fact any allylated alcohol may be deprotected according to the method of the invention. Preferred allylated alcohols, however, are those derived from primary and secondary alcohols. Particularly preferred are allylated nucleosides and nucleotides as described herein. It is possible to deprotect tertiary allylated alcohols—the reaction is simply slower (although deprotection may be in such, and other deprotections of this invention, accelerated if necessary by heating the solution, e.g. to 40° C., preferably 50° C. or higher such as approximately 60° C. or even up to 80° C.).

It is also possible to deprotect allylated primary or secondary amines and allylated thiols.

As noted earlier, the aqueous solution in which allyl deprotection is effected need not be 100% (as the continuous phase). However, substantially pure water (e.g. at least 98 vol % preferably about 100 vol %) is preferred. Cosolvents are generally not required although they can assist in the solubilisation of the allylated substrate for the deallylation. Generally, biomolecules are readily soluble in water (e.g. pure water) in which the deprotection reaction described herein may be effected. If desirable, one or more water-miscible cosolvents may be employed. Appropriate solvents include acetonitrile or dimethylsulfoxide, methanol, ethanol and acetone, methanol being preferred. Less preferred solvents include tetrahydrofuran (THF) and dioxane.

In the method of allyl deprotection according to the invention, a soluble metal complex is formed comprising a transition metal and one or more water-soluble phosphine and water-soluble nitrogen-containing phosphine ligands. More than one type of water-soluble phosphine/nitrogen-containing phosphine ligand may be used in a deallylation reaction although generally only one type of these classes of ligand will be used in a given reaction. We believe the deallylation reaction to be catalytic. Accordingly, the quantity of transition metal, e.g. palladium, may be less than 1 mol % (calculated relative to the allyl-protected compound to be deprotected). Advantageously the amount of catalyst may be much less than 1 mol %, e.g. <0.50 mol %, preferably <0.10 mol %, particularly <0.05 mol %. Even lower quantities of metal may be used, for example <0.03 or even <0.01 mol %. As those skilled in the art will be aware, however, as quantity of catalyst ds reduced, so too is the speed of the reaction. The skilled person will be able to judge, in any instance, the precise quantity of transition metal and thus catalyst most optimally suited to any particular deallylation reaction.

In contrast to the amount of metal required in forming the active catalyst, the quantity of water-soluble phosphorus-containing ligand(s) used must be greater than 1 molar equivalent (again calculated relative to the allyl-protected compound to be deprotected). Preferably greater than 4, e.g. greater than 6, for example 8-12 molar equivalents of ligand may be used. Even higher quantities of ligand e.g. >20 mole equivalents may be used if desired.

The skilled person will be able to determine the quantity of ligand best suited to any individual reaction.

Where the blocking group is any of —C(R')$_2$—O—R", —C(R')$_2$—N(R")$_2$, —C(R')$_2$—N(H)R", —C(R')$_2$—S—R" and —C(R')$_2$—F, i.e. of formula Z, each R' may be independently H or an alkyl The intermediates produced advantageously spontaneously dissociate under aqueous conditions back to the natural 3' hydroxy structure, which permits further incorporation of another nucleotide. Any appropriate protecting group may be used, as discussed herein. Preferably, Z is of formula —C(R')$_2$—O—R", —C(R')$_2$—N(R")$_2$, —C(R')$_2$—N(H)R" and —C(R')$_2$—SR". Particularly preferably, Z is of the formula —C(R')$_2$—O—R", —C(R')$_2$—N(R")$_2$, and —C(R')$_2$—SR". R" may be a benzyl group or a substituted benzyl group.

One example of groups of structure —O—Z wherein Z is —C(R')$_2$—N(R")$_2$ are those in which —N(R")$_2$ is azido (—N$_3$). One preferred such example is azidomethyl wherein each R' is H. Alternatively, R' in Z groups of formula —C(R')$_2$—N$_3$ and other Z groups may be any of the other groups discussed herein.

Examples of typical R' groups include C$_{1-6}$ alkyl, particularly methyl and ethyl, and the following (in which each structure shows the bond which connects the R' moiety to the carbon atom to which it is attached in the Z groups; the asterisks (*) indicate the points of attachment):

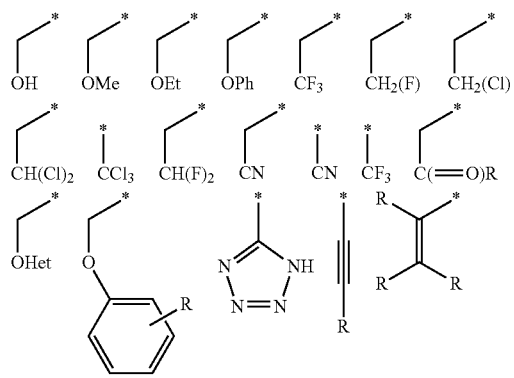

(wherein each R is an optionally substituted C$_{1-10}$ alkyl group, an optionally substituted alkoxy group, a halogen atom or functional group such as hydroxyl, amino, cyano, nitro, carboxyl and the like) and "Het" is a heterocyclic (which may for example be a heteroaryl group). These R' groups shown above are preferred where the other R' group is the same as the first or is hydrogen. Preferred Z groups are of formula C(R')$_2$N$_3$ in which the R' groups are selected from the structures given above and hydrogen; or in which (R')$_2$ represents an alkylidene group of formula =C(R''')$_2$, e.g. =C(Me)$_2$.

Where molecules contain Z groups of formula C(R')$_2$N$_3$, the azido group may be converted to amino by contacting such molecules with the phosphine or nitrogen-containing phosphines ligands described in detail in connection with the transition metal complexes which serve to cleave the allyl groups from compounds of formula PN—O-allyl, formula R—O-allyl, R$_2$N(allyl), RNH(allyl), RN(allyl)$_2$ and R—S-allyl. When transforming azido to amino, however, no transition metal is necessary. Alternatively, the azido group in Z groups of formula C(R')$_2$N$_3$ may be converted to amino by contacting such molecules with the thiols, in particular water-soluble thiols such as dithiothreitol (DTT).

Where an R' group represents a detectable label attached through a linking group, the other R' group or any other part of "Z" will generally not contain a detectable label, nor will the base of the nucleoside or nucleotide contain a detectable label. Appropriate linking groups for connecting the detectable label to the 3'blocking group will be known to the skilled person and examples of such groups are described in greater detail hereinafter.

Exemplary of linkages in R' groups containing detectable labels are those which contain one or more amide bonds. Such linkers may also contain an arylene, e.g. phenylene, group in the chain (i.e. a linking moiety —Ar— where the phenyl ring is part of the linker by way of its 1,4-disposed carbon atoms). The phenyl ring may be substituted at its non-bonded position with one or more substituents such as alkyl, hydroxyl, alkyloxy, halide, nitro, carboxyl or cyano and the like, particularly electron-withdrawing groups, which electron-withdrawing is either by induction or resonance. The linkage in the R' group may also include moieties such a —O—, —S(O)$_q$, wherein $q$ is 0, 1 or 2 or NH or Nalkyl. Examples of such Z groups are as follows:

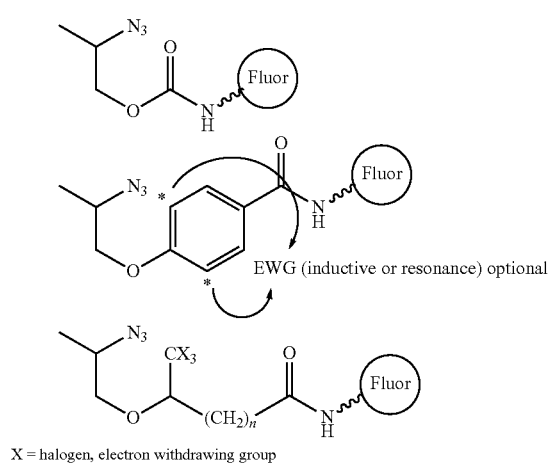

X = halogen, electron withdrawing group (wherein EWG stands for electron-withdrawing group; n is an integer of from 1 to 50, preferably 2-20, e.g. 3 to 10; and fluor indicates a fluorophore). An example of an electron-withdrawing group by resonance is nitro; a group which acts through induction is fluoro. The skilled person will be aware of other appropriate electron-withdrawing groups. In addition, it will be understood that whilst a fluorophore is indicated as being the detectable label present, other detectable groups as discussed in greater detail hereinafter may be included instead.

Where a detectable label is attached to a nucleotide at the 3'-blocking position, the linker need not be cleavable to have utility in those reactions, such as DNA sequencing, described herein which require the label to be "read" and removed before the next step of the reaction. This is because the label, when attached to the 3'block, will become separated from the nucleotide when the intermediate compounds described herein collapse so as to replace the "Z" group with a hydrogen atom. As noted above, each R" is or is part of a removable protecting group. R" may be a benzyl group or is substituted benzyl group is an alternative embodiment.

It will be appreciated that where it is possible to incorporate a detectable label onto a group R", the invention embraces this possibility. Thus, where R" is a benzyl group, the phenyl ring may bear a linker group to which is attached a fluorophore or other detectable group. Introduction of such groups does not prevent the ability to remove such R"s and they do not prevent the generation of the desired unstable intermediates during deprotection of blocking groups of formula Z.

As is known in the art, a "nucleotide" consists of a nitrogenous base, a sugar, and one or more phosphate groups. They are monomeric units of a nucleic acid sequence. In RNA, the sugar is a ribose, and in DNA a deoxyribose, i.e. a sugar lacking a hydroxyl group that is present in ribose. The nitrogenous base is a derivative of purine or pyrimidine. The purines are adenine (A) and guanine (G), and the pyrimidines are cytosine (C) and thymine (T) (or in the context of RNA, uracil (U)). The C-1 atom of deoxyribose is bonded to N-1 of a pyrimidine or N-9 of a purine. A nucleotide is also a phosphate ester or a nucleoside, with esterification occurring on the hydroxyl group attached to C-5 of the sugar. Nucleotides are usually mono, di- or triphosphates.

A "nucleoside" is structurally similar to a nucleotide, but is missing the phosphate moieties. An example of a nucleoside analogue would be one in which the label is linked to the base and there is no phosphate group attached to the sugar molecule.

Although the base is usually referred to as a purine or pyrimidine, the skilled person will appreciate that derivatives and analogues are available which do not alter the capability of the nucleotide or nucleoside to undergo Watson-Crick base pairing. "Derivative" or "analogue" means a compound or molecule whose core structure is the same as, or closely resembles that of, a parent compound, but which has a chemical or physical modification, such as a different or additional side group, or 2' and or 3' blocking groups, which allows the derivative nucleotide or nucleoside to be linked to another molecule. For example, the base can be a deazapurine. The derivatives should be capable of undergoing Watson-Crick pairing. "Derivative" and "analogue" also mean a synthetic nucleotide or nucleoside derivative having modified base moieties and/or modified sugar moieties. Such derivatives and analogs are discussed in, e.g., Scheit, Nucleotide Analogs (John Wiley & Son, 1980) and Uhlman et al., Chemical Reviews 90:543-584, 1990. Nucleotide analogs can also comprise modified phosphodiester linkages, including phosphorothioate, phosphorodithioate, alkyl-phosphonate, phosphoranilidate and phosphoramidate linkages. The analogs should be capable of undergoing Watson-Crick base pairing. "Derivative", "analog" and "modified" as used herein, may be used interchangeably, and are encompassed by the terms "nucleotide" and "nucleoside" defined herein.

In the context of the present invention, the term "incorporating" means becoming part of a nucleic acid (eg DNA)

molecule or oligonucleotide or primer. An oligonucleotide refers to a synthetic or natural molecule comprising a covalently linked sequence of nucleotides which are formed by a phosphodiester or modified phosphodiester bond between the 3' position of the pentose on one nucleotide and the 5' position of the pentose on an adjacent nucleotide.

The term "alkyl" covers straight chain, branched chain and cycloalkyl groups. Unless the context indicates otherwise, the term "alkyl" refers to groups having 1 to 10 carbon atoms, for example 1 to 8 carbon atoms, and typically from 1 to 6 carbon atoms, for example from 1 to 4 carbon atoms. Examples of alkyl groups include methyl, ethyl, propyl, isopropyl, n-butyl, isobutyl, tert-butyl, n-pentyl, 2-pentyl, 3-pentyl, 2-methyl butyl, 3-methyl butyl, and n-hexyl and its isomers.

Examples of cycloalkyl groups are those having from 3 to 10 ring atoms, particular examples including those derived from cyclopropane, cyclobutane, cyclopentane, cyclohexane and cycloheptane, bicycloheptane and decalin.

Where alkyl (including cycloalkyl) groups are substituted, particularly where these form either both of the R' groups of the molecules of the invention, examples of appropriate substituents include halogen substituents or functional groups such as hydroxyl, amino, cyano, nitro, carboxyl and the like. Such groups may also be substituents, where appropriate, of the other R' groups in the molecules of the invention.

The term amino refers to groups of type NR*R**, wherein R* and R** are independently selected from hydrogen, a $C_{1-6}$ alkyl group (also referred to as $C_{1-6}$ alkylamino or di-$C_{1-6}$ alkylamino).

The term "halogen" as used herein includes fluorine, chlorine, bromine and iodine.

The nucleotide molecules of the present invention are suitable for use in many different methods where the detection of nucleotides is required.

DNA sequencing methods, such as those outlined in U.S. Pat. No. 5,302,509 can be carried out using the nucleotides.

The present invention can make use of conventional detectable labels. Detection can be carried out by any suitable method, including fluorescence spectroscopy or by other optical means. The preferred label is a fluorophore, which, after absorption of energy, emits radiation at a defined wavelength. Many suitable fluorescent labels are known. For example, Welch et al. (*Chem. Eur. J.* 5(3):951-960, 1999) discloses dansyl-functionalised fluorescent moieties that can be used in the present invention. Zhu et al. (*Cytometry* 28:206-211, 1997) describes the use of the fluorescent labels Cy3 and Cy5, which can also be used in the present invention. Labels suitable for use are also disclosed in Prober et al. (*Science* 238:336-341, 1987); Connell et al. (*BioTechniques* 5(4):342-384, 1987), Ansorge et al. (*Nucl. Acids Res.* 15(11): 4593-4602, 1987) and Smith et al. (*Nature* 321:674, 1986). Other commercially available fluorescent labels include, but are not limited to, fluorescein, rhodamine (including TMR, texas red and Rox), alexa, bodipy, acridine, coumarin, pyrene, benzanthracene and the cyanins.

Multiple labels can also be used in the invention. For example, bi-fluorophore FRET cassettes (*Tet. Let.* 46:8867-8871, 2000) are well known in the art and can be utilised in the present invention. Multi-fluor dendrimeric systems (*J. Amer. Chem. Soc.* 123:8101-8108, 2001) can also be used.

Although fluorescent labels are preferred, other forms of detectable labels will be apparent as useful to those of ordinary skill. For example, microparticles, including quantum dots (Empodocles et al., *Nature* 399:126-130, 1999), gold nanoparticles (Reichert et al., *Anal. Chem.* 72:6025-6029, 2000) and microbeads (Lacoste et al., *Proc. Natl. Acad. Sci USA* 97(17):9461-9466, 2000) can all be used.

Multi-component labels can also be used in the invention. A multi-component label is one which is dependent on the interaction with a further compound for detection. The most common multi-component label used in biology is the biotin-streptavidin system. Biotin is used as the label attached to the nucleotide base. Streptavidin is then added separately to enable detection to occur. Other multi-component systems are available. For example, dinitrophenol has a commercially available fluorescent antibody that can be used for detection.

The invention has been and will be further described with reference to nucleotides. However, unless indicated otherwise, the reference to nucleotides is also intended to be applicable to nucleosides. The invention will also be further described with reference to DNA, although the description will also be applicable to RNA, PNA, and other nucleic acids, unless otherwise indicated.

The modified nucleotides of the invention may use a cleavable linker to attach the label to the nucleotide. The use of a cleavable linker ensures that the label can, if required, be removed after detection, avoiding any interfering signal with any labelled nucleotide incorporated subsequently.

Generally, the use of cleavable linkers is preferable, particularly in the methods of the invention hereinbefore described except where the detectable label is attached to the nucleotide by forming part of the "Z" group.

Those skilled in the art will be aware of the utility of dideoxynucleoside triphosphates in so-called Sanger sequencing methods, and related protocols (Sanger-type), which rely upon randomised chain-termination at a particular type of nucleotide. An example of a Sanger-type sequencing protocol is the BASS method described by Metzker (infra). Other Sanger-type sequencing methods will be known to those skilled in the art.

Sanger and Sanger-type methods generally operate by the conducting of an experiment in which eight types of nucleotides are provided, four of which contain a 3'OH group; and four of which omit the OH group and which are labeled differently from each other. The nucleotides used which omit the 3'OH group—dideoxy nucleotides—are conventionally abbreviated to ddNTPs. As is known by the skilled person, since the ddNTPs are labeled differently, by determining the positions of the terminal nucleotides incorporated, and combining this information, the sequence of the target oligonucleotide may be determined.

The nucleotides of the present invention, it will be recognized, may be of utility in Sanger methods and related protocols since the same effect achieved by using ddNTPs may be achieved by using the novel 3'-OH blocking groups described herein: both prevent incorporation of subsequent nucleotides.

The use of the nucleotides according to the present invention in Sanger and Sanger-type sequencing methods, wherein the linker connecting the detectable label to the nucleotide may or may not be cleavable, forms a still further aspect of this invention. Viewed from this aspect, the invention provides the use of such nucleotides in a Sanger or a Sanger-type sequencing method.

Where 3'-OH Z-blocked nucleotides according to the present invention are used, it will be appreciated that the detectable labels attached to the nucleotides need not be connected via cleavable linkers, since in each instance where a labelled nucleotide of the invention is incorporated, no nucleotides need to be subsequently incorporated and thus the label need not be removed from the nucleotide.

Moreover, it will be appreciated that monitoring of the incorporation of 3'OH blocked nucleotides may be determined by use of radioactive $^{32}P$ in the phosphate groups attached. These may be present in either the ddNTPs themselves or in the primers used for extension. Where the blocking groups are of formula "Z", this represents a further aspect of the invention.

Viewed from this aspect, the invention provides the use of a nucleotide having a 3'OH group blocked with a "Z" group in a Sanger or a Sanger-type sequencing method. In this embodiment, a $^{32}$P detectable label may be present in either the ddNTPs used in the primer used for extension.

Cleavable linkers are known in the art, and conventional chemistry can be applied to attach a linker to a nucleotide base and a label. The linker can be cleaved by any suitable method, including exposure to acids, bases, nucleophiles, electrophiles, radicals, metals, reducing or oxidising agents, light, temperature, enzymes etc. The linker as discussed herein may also be cleaved with the same catalyst used to cleave the 3'O-blocking group bond. Suitable linkers can be adapted from standard chemical blocking groups, as disclosed in Greene & Wuts, Protective Groups in Organic Synthesis, John Wiley & Sons. Further suitable cleavable linkers used in solid-phase synthesis are disclosed in Guillier et al. (Chem. Rev. 100:2092-2157, 2000).

The use of the term "cleavable linker" is not meant to imply that the whole linker is required to be removed from e.g., the nucleotide base. Where the detectable label is attached to the base, the nucleoside cleavage site can be located at a position on the linker that ensures that part of the linker remains attached to the nucleotide base after cleavage.

Where the detectable label is attached to the base, the linker can be attached at any position on the nucleotide base provided that Watson-Crick base pairing can still be carried out. In the context of purine bases, it is preferred if the linker is attached via the 7-position of the purine or the preferred deazapurine analogue, via an 8-modified purine, via an N-6 modified adenosine or an N-2 modified guanine. For pyrimidines, attachment is preferably via the 5-position on cytosine, thymidine or uracil and the N-4 position on cytosine. Suitable nucleotide structures are shown in FIG. 1. For each structure in FIG. 1 X can be H, phosphate, diphosphate or triphosphate. $R_1$ and $R_2$ can be the same or different, and are selected from H, OH, O-allyl, or formula Z as described herein or any other group which can be transformed into an OH, including, but not limited to, a carbonyl, provided that at least one of $R_1$ and $R_2$ is O-allyl or formula Z as described herein. Some suitable functional groups for $R_1$ and $R_2$ include the structures shown in FIGS. 3 and 4.

Figure 3:
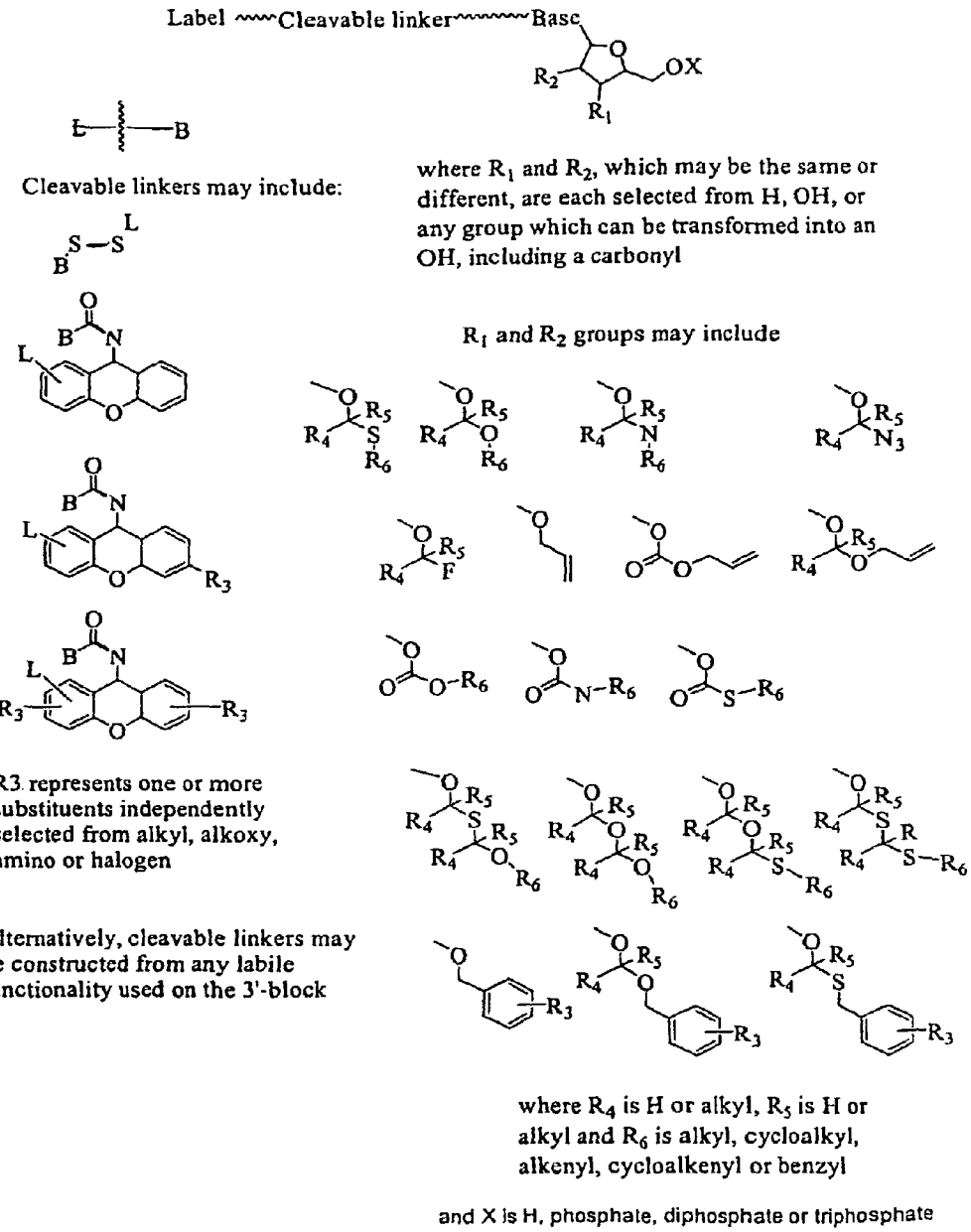

Suitable linkers are shown in FIG. 3 and include, but are not limited to, disulfide linkers (1), acid labile linkers (2, 3, 4 and 5; including dialkoxybenzyl linkers (e.g., 2), Sieber linkers (e.g., 3), indole linkers (e.g., 4), t-butyl Sieber linkers (e.g., 5)), electrophilically cleavable linkers, nucleophilically cleavable linkers, photocleavable linkers, cleavage under reductive conditions, oxidative conditions, cleavage via use of safety-catch linkers, and cleavage by elimination mechanisms.

A. Electrophilically Cleaved Linkers.

Electrophilically cleaved linkers are typically cleaved by protons and include cleavages sensitive to acids. Suitable linkers include the modified benzylic systems such as trityl, p-alkoxybenzyl esters and p-alkoxybenzyl amides. Other suitable linkers include tert-butyloxycarbonyl (Boc) groups and the acetal system.

The use of thiophilic metals, such as nickel, silver or mercury, in the cleavage of thioacetal or other sulfur-containing protecting groups can also be considered for the preparation of suitable linker molecules.

B. Nucleophilically Cleaved Linkers.

Nucleophilic cleavage is also a well recognised method in the preparation of linker molecules. Groups such as esters that are labile in water (i.e., can be cleaved simply at basic pH) and groups that are labile to non-aqueous nucleophiles, can be used. Fluoride ions can be used to cleave silicon-oxygen bonds in groups such as triisopropyl silane (TIPS) or t-butyldimethyl silane (TBDMS).

C. Photocleavable Linkers.

Photocleavable linkers have been used widely in carbohydrate chemistry. It is preferable that the light required to activate cleavage does not affect the other components of the modified nucleotides. For example, if a fluorophore is used as the label, it is preferable if this absorbs light of a different wavelength to that required to cleave the linker molecule. Suitable linkers include those based on O-nitrobenzyl compounds and nitroveratryl compounds. Linkers based on benzoin chemistry can also be used (Lee et al., J. Org. Chem. 64:3454-3460, 1999).

D. Cleavage Under Reductive Conditions

There are many linkers known that are susceptible to reductive cleavage. Catalytic hydrogenation using palladium-based catalysts has been used to cleave benzyl and benzyloxycarbonyl groups. Disulfide bond reduction is also known in the art.

E. Cleavage Under Oxidative Conditions

Oxidation-based approaches are well known in the art. These include oxidation of p-alkoxybenzyl groups and the oxidation of sulfur and selenium linkers. The use of aqueous iodine to cleave disulfides and other sulfur or selenium-based linkers is also within the scope of the invention.

F. Safety-Catch Linkers

Safety-catch linkers are those that cleave in two steps. In a preferred system the first step is the generation of a reactive nucleophilic center followed by a second step involving an intra-molecular cyclization that results in cleavage. For example, levulinic ester linkages can be treated with hydrazine or photochemistry to release an active amine, which can then be cyclised to cleave an ester elsewhere in the molecule (Burgess et al., J. Org. Chem. 62:5165-5168, 1997).

G. Cleavage by Elimination Mechanisms

Elimination reactions can also be used. For example, the base-catalysed elimination of groups such as Fmoc and cyanoethyl, and palladium-catalysed reductive elimination of allylic systems, can be used.

As well as the cleavage site, the linker can comprise a spacer unit. The spacer distances e.g., the nucleotide base from the cleavage site or label. The length of the linker is unimportant provided that the label is held a sufficient distance from the nucleotide so as not to interfere with any interaction between the nucleotide and an enzyme.

In a preferred embodiment the linker may consist of the same functionality as the block. This will make the deprotection and deblocking process more efficient, as only a single treatment will be required to remove both the label and the block.

Particularly preferred linkers are phosphine-cleavable azide containing linkers.

A method for determining the sequence of a target polynucleotide can be carried out by contacting the target polynucleotide separately with the different nucleotides to form the complement to that of the target polynucleotide, and detecting the incorporation of the nucleotides. Such a method makes use of polymerisation, whereby a polymerase enzyme extends the complementary strand by incorporating the correct nucleotide complementary to that on the target. The polymerisation reaction also requires a specific primer to initiate polymerisation.

For each cycle, the incorporation of the modified nucleotide is carried out by the polymerase enzyme, and the incorporation event is then determined. Many different polymerase enzymes exist, and it will be evident to the person of ordinary skill which is most appropriate to use. Preferred enzymes include DNA polymerase I, the Klenow fragment, DNA polymerase III, T4 or T7 DNA polymerase, Taq polymerase or Vent polymerase. Polymerases engineered to have specific properties can also be used. As noted earlier, the molecule is preferably incorporated by a polymerase and particularly from *Thermococcus* sp., such as 9°N. Even more preferably, the polymerase is a mutant 9°N A485L and even more preferably is a double mutant Y409V and A485L. An example of one such preferred enzyme is *Thermococcus* sp. 9°N exo −Y409V A485L available from New England Biolabs. Examples of such appropriate polymerases are disclosed in *Proc. Natl. Acad. Sci. USA*, 1996 (93), pp 5281-5285, *Nucleic Acids Research*, 1999 (27), pp 2454-2553 and *Acids Research*, 2002 (30), pp 605-613.

The sequencing methods are preferably carried out with the target polynucleotide arrayed on a solid support. Multiple target polynucleotides can be immobilised on the solid support through linker molecules, or can be attached to particles, e.g., microspheres, which can also be attached to a solid support material. The polynucleotides can be attached to the solid support by a number of means, including the use of biotin-avidin interactions. Methods for immobilizing polynucleotides on a solid support are well known in the art, and include lithographic techniques and "spotting" individual polynucleotides in defined positions on a solid support. Suitable solid supports are known in the art, and include glass slides and beads, ceramic and silicon surfaces and plastic materials. The support is usually a flat surface although microscopic beads (microspheres) can also be used and can in turn be attached to another solid support by known means. The microspheres can be of any suitable size, typically in the range of from 10 nm to 100 nm in diameter. In a preferred embodiment, the polynucleotides are attached directly onto a planar surface, preferably a planar glass surface. Attachment will preferably be by means of a covalent linkage. Preferably, the arrays that are used are single molecule arrays that comprise polynucleotides in distinct optically resolvable areas, e.g., as disclosed in International Application No. WO00/06770.

The sequencing method can be carried out on both single polynucleotide molecule and multi-polynucleotide molecule arrays, i.e., arrays of distinct individual polynucleotide molecules and arrays of distinct regions comprising multiple copies of one individual polynucleotide molecule. Single molecule arrays allow each individual polynucleotide to be resolved separately. The use of single molecule arrays is preferred. Sequencing single molecule arrays non-destructively allows a spatially addressable array to be formed.

The method makes use of the polymerisation reaction to generate the complementary sequence of the target. Conditions compatible with polymerization reactions will be apparent to the skilled person.

To carry out the polymerase reaction it will usually be necessary to first anneal a primer sequence to the target polynucleotide, the primer sequence being recognised by the polymerase enzyme and acting as an initiation site for the subsequent extension of the complementary strand. The primer sequence may be added as a separate component with respect to the target polynucleotide. Alternatively, the primer and the target polynucleotide may each be part of one single stranded molecule, with the primer portion forming an intramolecular duplex with a part of the target, i.e., a hairpin loop structure. This structure may be immobilised to the solid support at any point on the molecule. Other conditions necessary for carrying out the polymerase reaction, including temperature, pH, buffer compositions etc., will be apparent to those skilled in the art.

The modified nucleotides of the invention are then brought into contact with the target polynucleotide, to allow polymerisation to occur. The nucleotides may be added sequentially, i.e., separate addition of each nucleotide type (A, T, G or C), or added together. If they are added together, it is preferable for each nucleotide type to be labelled with a different label.

This polymerisation step is allowed to proceed for a time sufficient to allow incorporation of a nucleotide.

Nucleotides that are not incorporated are then removed, for example, by subjecting the array to a washing step, and detection of the incorporated labels may then be carried out.

Detection may be by conventional means, for example if the label is a fluorescent moiety, detection of an incorporated base may be carried out by using a confocal scanning microscope to scan the surface of the array with a laser, to image a fluorophore bound directly to the incorporated base. Alternatively, a sensitive 2-D detector, such as a charge-coupled detector (CCD), can be used to visualise the individual signals generated. However, other techniques such as scanning near-field optical microscopy (SNOM) are available and may be used when imaging dense arrays. For example, using SNOM, individual polynucleotides may be distinguished when separated by a distance of less than 100 nm, e.g., 10 nm to 10 μm. For a description of scanning near-field optical microscopy, see Moyer et al., *Laser Focus World* 29:10, 1993. Suitable apparatus used for imaging polynucleotide arrays are known and the technical set-up will be apparent to the skilled person.

After detection, the label may be removed using suitable conditions that cleave the linker and the 3'OH block to allow for incorporation of further modified nucleotides of the invention. Appropriate conditions may be those described herein for allyl group and for "Z" group deprotections. These conditions can serve to deprotect both the linker (if cleavable) and the blocking group. Alternatively, the linker may be deprotected separately from the allyl group by employing methods of cleaving the linker known in the art (which do not sever the O-blocking group bond) followed by deprotection.

This invention may be further understood with reference to the following examples which serve to illustrate the invention and not to limit its scope.

3'-OH Protected with an Azidomethyl Group as a Protected Form of a Hemiaminal:

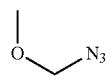

Nucleotides bearing this blocking group at the 3'position have been synthesised, shown to be successfully incorporated by DNA polymerases, block efficiently and may be subsequently removed under neutral, aqueous conditions using water soluble phosphines or thiols allowing further extension:

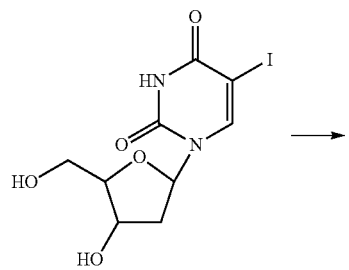

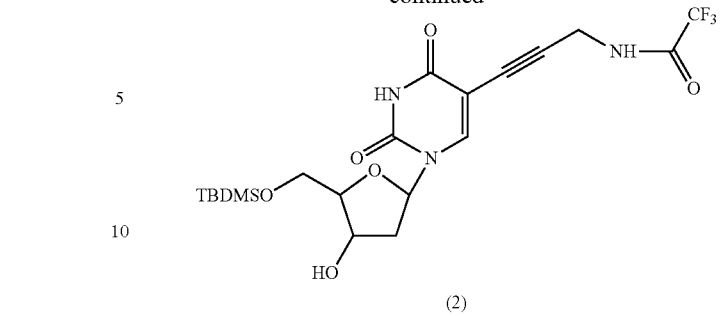

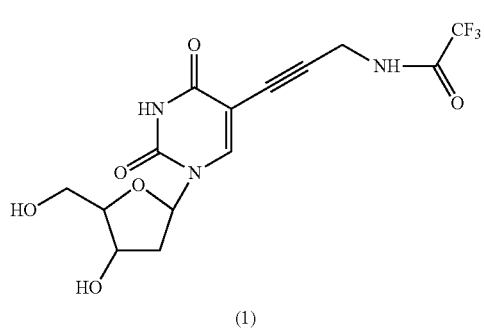

5-[3-(2,2,2-trifluoroacetamido)-prop-1-ynyl]-2'-deoxyuridine (1)

To a solution of 5-iodo-2'-deoxyuridine (1.05 g, 2.96 mmol) and CuI (114 mg, 0.60 mmol) in dry DMF (21 ml) was added triethylamine (0.9 ml). After stirring for 5 min trifluoro-N-prop-2-ynyl-acetamide (1.35 g, 9.0 mmol) and Pd(PPh$_3$)$_4$ (330 mg, 0.29 mmol) were added to the mixture and the reaction was stirred at room temperature in the dark for 16 h. Methanol (MeOH) (40 ml) and bicarbonate dowex added to the reaction mixture and stirred for 45 min. The mixture was filtered and the filtrate washed with MeOH and the solvent was removed under vacuum. The crude mixture was purified by chromatography on silica (ethyl acetate (EtOAc) to EtOAc:MeOH 95:5) to give slightly yellow crystals (794 mg, 71%). $^1$H NMR (d$_6$ dimethylsulfoxide (DMSO)) δ 2.13-2.17 (m, 2H, H-2'), 3.57-3.65 (m, 2H, H-5'), 3.81-3.84 (m, 1H, H-4'), 4.23-4.27 (m, 3H, H-3', CH$_2$N), 5.13 (t, J=5.0 Hz, 1H, OH), 5.20 (d, J=4.3 Hz, 1H, OH), 6.13 (t, J=6.7 Hz, 1H, H-1'), 8.23 (s, 1H, H-6), 10.11 (t, J=5.6 Hz, 1H, NH), 11.70 (br s, 1H, NH). Mass (−ve electrospray) calcd for C$_{14}$H$_{14}$F$_3$N$_3$O$_6$ 377.08. found 376.

5'-O-(tert-butydimethylsilyl)-5-[3-(2,2,2-trifluoroacetamido)-prop-1-ynyl]-2'-deoxyuridine (2)

To a solution of (1) (656 mg, 1.74 mmol) in dry DMF (15 ml) was added t-butyldimethylsilylchloride (288 mg, 1.91 mmol) in small portions, followed by imidazole (130 mg, 1.91 mmol). The reaction was followed by TLC and was completed after stirring for 8 h at room temperature. The reaction was quenched with sat. aq. NaCl solution. EtOAc (25 ml) was added to the reaction mixture and the aqueous layer was extracted with EtOAc three times. After drying the combined organics (MgSO$_4$), the solvent was removed under vacuum. Purification by chromatography on silica (EtOAc: petroleum ether 8:2) gave (2) as slightly yellow crystals (676 mg, 83%). $^1$H NMR (d$_6$ DMSO) δ 0.00 (s, 6H, CH$_3$), 0.79 (s, 9H, tBu), 1.93-2.00 (m, 1H, H-2'), 2.06-2.11 (m, 1H, H-2'), 3.63-3.75 (m, 2H, H-5'), 3.79-3.80 (m, 1H, H-4'), 4.12-4.14 (m, 3H, H-3', CH$_2$N), 5.22 (d, J=4.1 Hz, 1H, OH), 6.03 (t, J=6.9 Hz, 1H, H-1'), 7.86 (s, 1H, H-6), 9.95 (t, J=5.4 Hz, 1H, NH), 11.61 (br s, 1H, NH). Mass (−ve electrospray) calcd for C$_{20}$H$_{28}$F$_3$N$_3$O$_6$Si 491.17. found 490.

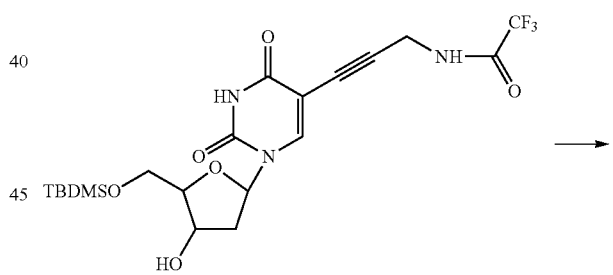

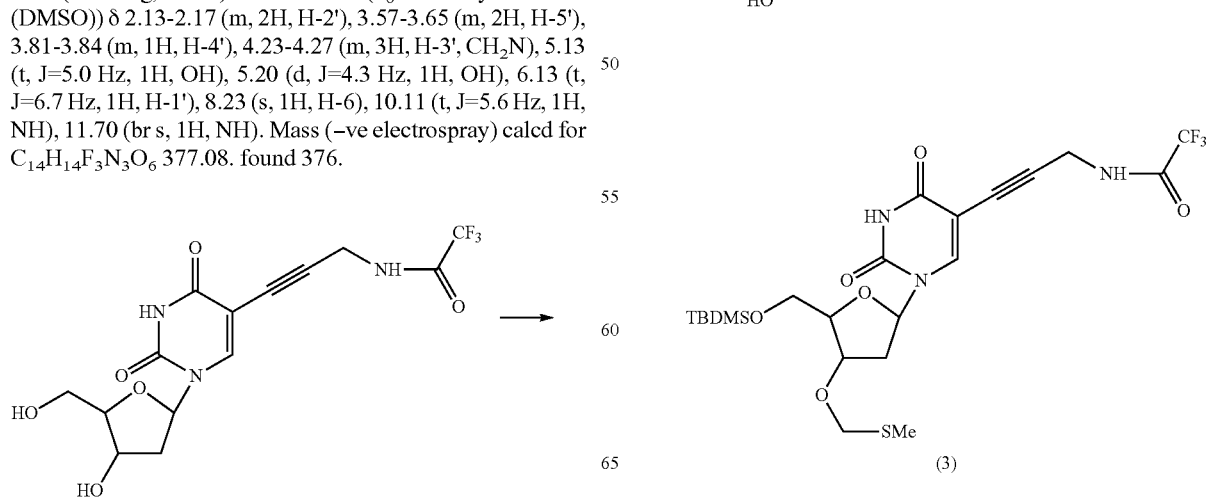

5'-O-(tert-Butydimethylsilyl)-3'-O-methylthiomethyl-5-[3-(2,2,2-trifluoroacetamido)-prop-1-ynyl]-2'-deoxyuridine (3)

To a solution of (2) (1.84 g, 3.7 mmol) in dry DMSO (7 ml) was added acetic acid (3.2 ml) and acetic anhydride (10.2 ml). The mixture was stirred for 2 days at room temperature, before it was quenched with sat. aq. NaHCO$_3$. EtOAc (50 ml) was added and the aqueous layer was extracted three times with ethyl acetate. The combined organic layers were washed with sat. aq. NaHCO$_3$ solution and dried (MgSO$_4$). After removing the solvent under reduced pressure, the product (3) was purified by chromatography on silica (EtOAc:petroleum ether 8:2) yielding a clear sticky oil (1.83 g, 89%) $^1$H NMR (d$_6$ DMSO): δ 0.00 (s, 6H, CH$_3$), 0.79 (s, 9H, tBu), 1.96-2.06 (m, 1H, H-2'), 1.99 (s, 3H, SCH$_3$), 2.20-2.26 (m, 1H, H-2'), 3.63-3.74 (m, 2H, H-5'), 3.92-3.95 (m, 1H, H-4'), 4.11-4.13 (m, 2H, CH$_2$), 4.28-4.30 (m, 1H, H-3'), 4.59 (br s, 2H, CH$_2$), 5.97 (t, J=6.9 Hz, 1H, H-1'), 7.85 (s, 1H, H-6), 9.95 (t, J=5.3 Hz, 1H, NH), 11.64 (s, 1H, NH). Mass (−ve electrospray) calcd for C$_{22}$H$_{32}$F$_3$N$_3$O$_6$SSi 551.17. found 550.

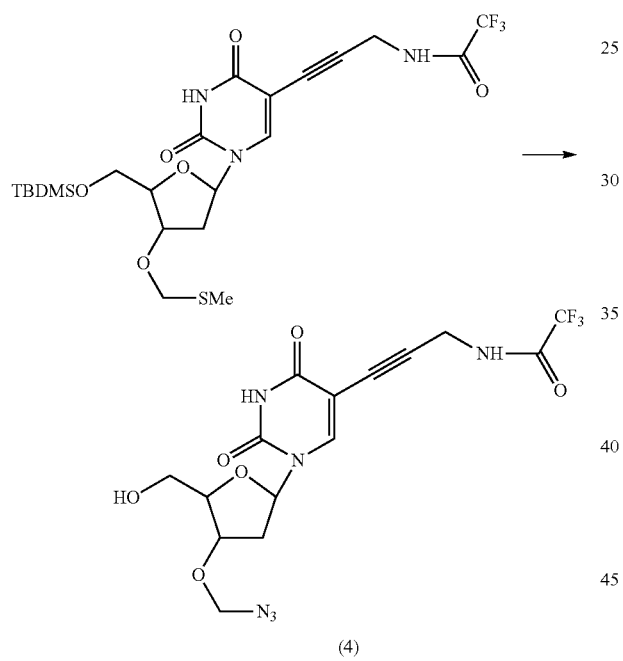

(4)

3'-O-Azidomethyl-5-[3-(2,2,2-trifluoroacetamido)-prop-1-ynyl]-2'-deoxyuridine (4)

To a solution of (3) (348 mg, 0.63 mmol) and cyclohexene (0.32 ml, 3.2 mmol) in dry CH$_2$Cl$_2$ (5 ml) at 4° C., sulfuryl chloride (1M in CH$_2$Cl$_2$, 0.76 ml, 0.76 mmol) was added drop wise under N$_2$. After 10 min TLC indicated the full consumption of the nucleoside (3). The solvent was evaporated and the residue was subjected to high vacuum for 20 min. It was then redissolved in dry DMF (3 ml) and treated with NaN$_3$ (205 mg, 3.15 mmol). The resulting suspension was stirred under room temperature for 2 h. The reaction was quenched with CH$_2$Cl$_2$ and the organic layers were washed with sat aq. NaCl solution. After removing the solvent, the resulting yellow gum was redissolved in THF (2 ml) and treated with TBAF (1 M in THF, 0.5 ml) at room temperature for 30 min. The solvent was removed and the reaction worked up with CH$_2$Cl$_2$ and sat. aq. NaHCO$_3$ solution. The aqueous layer was extracted three times with CH$_2$Cl$_2$. Purification by chromatography on silica (EtOAc:petroleum ether 1:1 to EtOAc) gave (4) (100 mg, 37%) as a pale yellow foam. $^1$H NMR (d$_6$ DMSO) δ 2.15-2.26 (m, 2H, H-2'), 3.47-3.57 (m, 2H, H-5'), 3.88-3.90 (m, 1H, H-4'), 4.14 (d, J=4.7 Hz, 2H, CH$_2$NH), 4.24-4.27 (m, 1H, H-3'), 4.75 (s, 2H, CH$_2$N$_3$), 5.14 (t, J=5.2 Hz, 1H, OH), 5.96-6.00 (m, 1H, H-1'), 8.10 (s, 1H, H-6), 10.00 (s, 1H, NHCOCF$_3$)), 11.26 (s, 1H, NH).

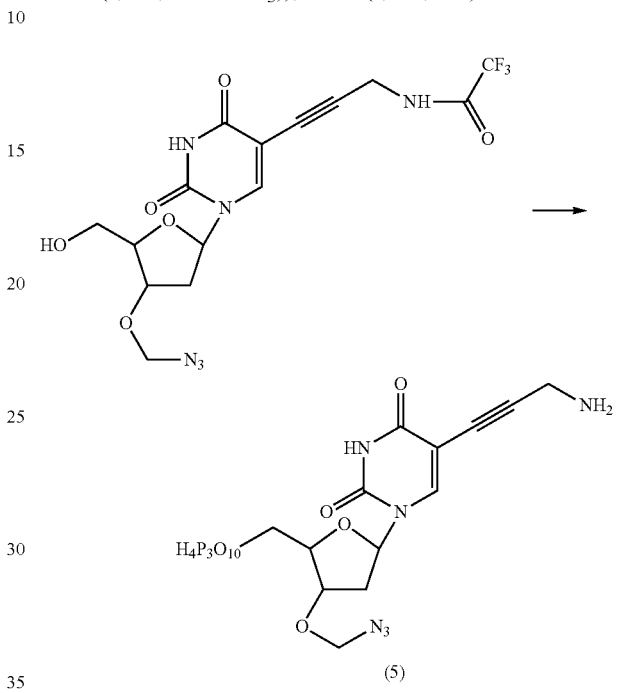

(5)

Preparation of bis(tri-n-butylammonium)pyrophosphate (0.5 M solution in DMF)

Tetrasodium diphosphate decahydrate (1.5 g, 3.4 mmol) was dissolved in water (34 ml) and the solution was applied to a column of dowex in the H$^+$ form. The column was eluted with water. The eluent dropped directly into a cooled (ice bath) and stirred solution of tri-n-butylamine (1.6 ml, 6.8 mmol) in EtOH (14 ml). The column was washed until the pH of the eluent increased to 6. The aq. ethanol solution was evaporated to dryness and then co-evaporated twice with ethanol and twice with anhydrous DMF. The residue was dissolved in DMF (6.7 ml). The pale yellow solution was stored over 4 Å molecular sieves.

3'-O-Azidomethyl-5-(3-amino-prop-1-ynyl)-2'-deoxyuridine 5'-O-nucleoside triphosphate (5)

The nucleoside (4) and proton sponge was dried over P$_2$O$_5$ under vacuum overnight. A solution of (4) (92 mg, 0.21 mmol) and proton sponge (90 mg, 0.42 mmol) in trimethylphosphate (0.5 ml) was stirred with 4 Å molecular sieves for 1 h. Freshly distilled POCl$_3$ (24 μl, 0.26 mmol) was added and the solution was stirred at 4° C. for 2 h. The mixture was slowly warmed up to room temperature and bis(tri-n-butyl ammonium) pyrophosphate (1.7 ml, 0.85 mmol) and anhydrous tri-n-butyl amine (0.4 ml, 1.7 mmol) was added. After 3 min, the reaction was quenched with 0.1 M TEAB (triethylammonium bicarbonate) buffer (15 ml) and stirred for 3 h.

The water was removed under reduced pressure and the resulting residue dissolved in concentrated ammonia (ρ 0.88, 15 ml) and stirred at room temperature for 16 h. The reaction mixture was then evaporated to dryness. The residue was dissolved in water and the solution applied to a DEAE-Sephadex A-25 column. MPLC was performed with a linear gradient of TEAB. The triphosphate was eluted between 0.7 M and 0.8 M buffer. Fractions containing the product were combined and evaporated to dryness. The residue was dissolved in water and further purified by HPLC. HPLC: $t_r(5)$: 18.8 min (Zorbax C18 preparative column, gradient: 5% to 35% B in 30 min, buffer A 0.1M TEAB, buffer B MeCN) The product was isolated as a white foam (76 O.D., 7.6 μmol, 3.8%, $\epsilon_{280}$=10000). $^1$H NMR (D$_2$O) δ 1.79 (s, CH$_2$), 2.23-2.30; 2.44-2.50 (2×m, 2H, H-2'), 3.85 (m, CH$_2$NH), 4.10-4.18 (m, 2H, H-5'), 4.27 (br s, H-4'), 4.48-4.50 (m, H-3'), 4.70-4.77 (m, CH$_2$N$_3$), 6.21 (t, J=6.6 Hz, H-1'), 8.32 (s, 1H, H-6). $^{31}$P NMR (D$_2$O) δ −6.6 (m, 1P, P$_\gamma$), −10.3 (d, J=18.4 Hz, 1P, P$_\alpha$), −21.1 (m, 1P, P$_\beta$). Mass (−ve electrospray) calcd for C$_{13}$H$_{19}$N$_6$O$_{14}$P$_3$ 576.02. found 575.

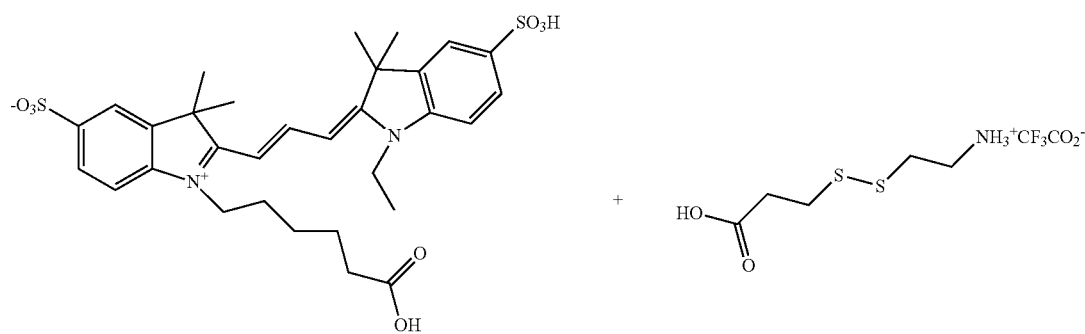

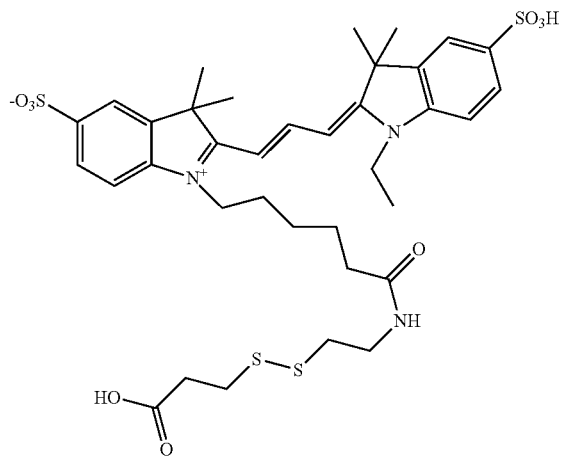

Cy-3disulfide Linker

The starting disulfide (4.0 mg, 13.1 μmol) was dissolved in DMF (300 μL) and diisopropylethylamine (4 μL) was slowly added. The mixture was stirred at room temperature and a solution of Cy-3 dye (5 mg, 6.53 μmol) in DMF (300 μL) was added over 10 min. After 3.5 h, on complete reaction, the volatiles were evaporated under reduced pressure and the crude residue was HPLC purified on a Zorbax analytical column SB-C18 with a flow rate of 1 ml/min in 0.1M triethylammonium bicarbonate buffer (buffer A) and $CH_3CN$ (buffer B) using the following gradient: 5 min 2% B; 31 min 55% B; 33 min 95% B; 37 min 95%; 39 min 2% B; 44 min. 2% B. The expected Cy3-disulfide linker was eluted with a $t_r$: 21.8 min. in 70% yield (based on a UV measurement; $\epsilon_{550}$ 150,000 $cm^{-1}$ $M^{-1}$ in $H_2O$) as a hygroscopic solid. $^1$H NMR ($D_2O$) δ 1.31-1.20 (m+t, J=7.2 Hz, 5H, $CH_2$+$CH_3$), 1.56-1.47 (m, 2H, $CH_2$), 1.67 (s, 12H, 4 $CH_3$), 1.79-1.74 (m, 2H, $CH_2$), 2.11 (t, J=6.9 Hz, 2H, $CH_2$), 2.37 (t, J=6.9 Hz, 2H, $CH_2$), 2.60 (t, J=6.3 Hz, 2H, $CH_2$), 2.67 (t, J=6.9 Hz, 2H, $CH_2$), 3.27 (t, J=6.1 Hz, 2H, $CH_2$), 4.10-4.00 (m, 4H, 2$CH_2$), 6.29 (dd, J=13.1, 8.1 Hz, 2H, 2 =CH), 7.29 (dd, 2H, J=8.4, 6.1 Hz, 2 = CH), 7.75-7.71 (m, 2H, 2 =CH), 7.78 (s, 2H, =CH), 8.42 (t, J=12.8 Hz, 1H, =CH). Mass (-ve electrospray) calcd for $C_{36}H_{47}N_3O_9S_4$ 793.22. found 792 (M−H), 396 [M/2].

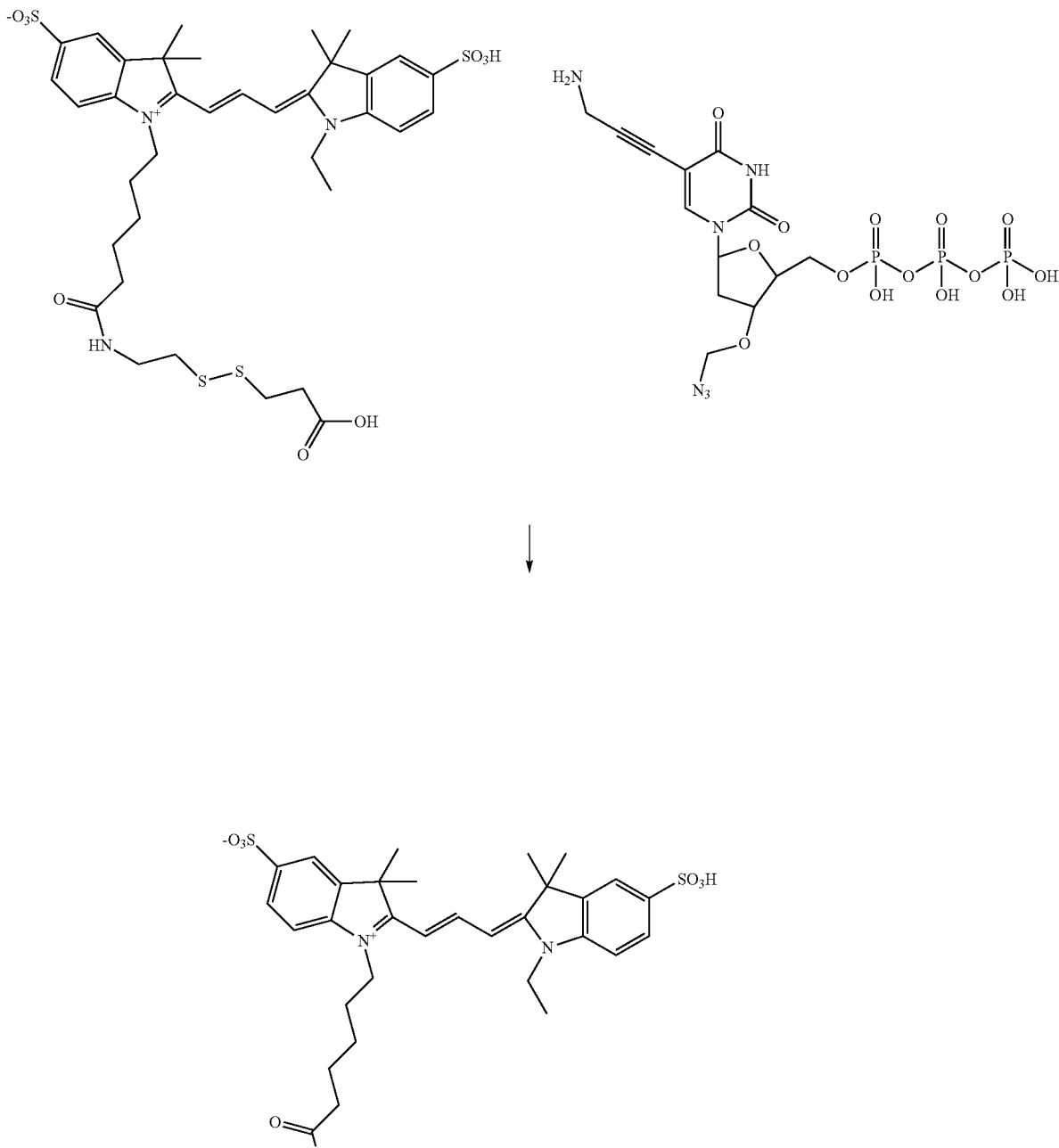

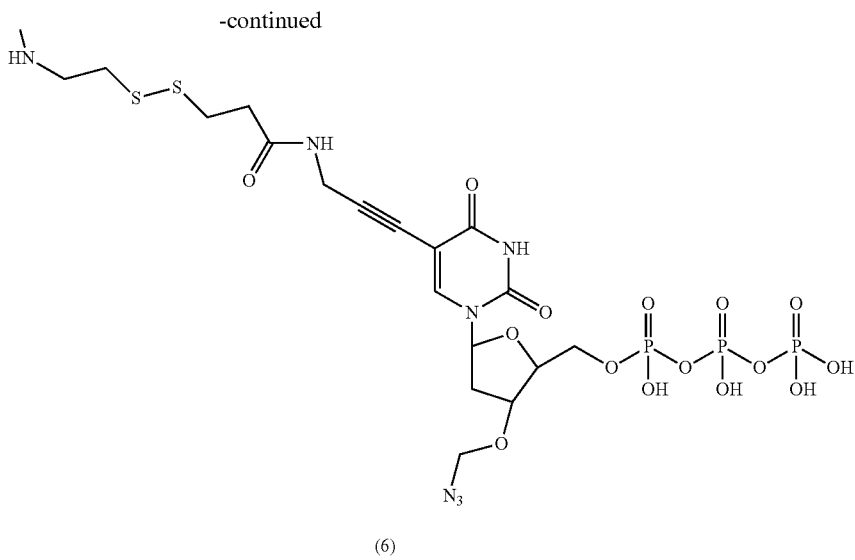

(6)

A mixture of Cy3 disulphide linker (2.5 µmol), disuccinimidyl carbonate (0.96 mg, 3.75 µmol) and DMAP (0.46 mg, 3.75 µmol) were dissolved in dry DMF (0.5 ml) and stirred at room temperature for 10 min. The reaction was monitored by TLC (MeOH:CH$_2$Cl$_2$ 3:7) until all the dye linker was consumed. Then a solution of (5) (7.5 µmol) and n-Bu$_3$N (30 µl, 125 µmol) in DMF (0.2 ml) was added to the reaction mixture and stirred at room temperature for 1 h. TLC (MeOH:CH$_2$Cl$_2$ 4:6) showed complete consumption of the activated ester and a dark red spot appeared on the baseline. The reaction was quenched with TEAB buffer (0.1M, 10 ml) and loaded on a DEAE Sephadex column (2×5 cm). The column was first eluted with 0.1 M TEAB buffer (100 ml) to wash off organic residues and then 1 M TEAB buffer (100 ml). The desired triphosphate analogue (6) was eluted out with 1 M TEAB buffer. The fraction containing the product were combined, evaporated and purified by HPLC. HPLC conditions: t$_r$ (6): 16.1 min (Zorbax C18 preparative column, gradient: 2% to 55% B in 30 min, buffer A 0.1M TEAB, buffer B MeCN). The product was isolated as dark red solid (1.35 µmol, 54%, $\epsilon_{550}$=150000). $^1$H NMR (D$_2$O) δ 1.17-1.28 (m, 6H 3×CH$_2$), 1.41-1.48 (m, 3H, CH$_3$), 1.64 (s, 12H, 4×CH$_3$), 1.68-1.71 (m, 2H, CH$_2$), 2.07-2.10 (m, 3H, H-2', CH$_2$), 2.31-2.35 (m, 1H, H-2'), 2.50-2.54 (m, 2H, CH$_2$), 2.65 (t, J=5.9 Hz, 2H, CH$_2$), 2.76 (t, J=7.0 Hz, 2H, CH$_2$), 3.26-3.31 (m, 2H, CH$_2$), 3.88-3.91 (m, 2H CH$_2$), 3.94-4.06 (m, 3H, CH$_2$N, H-5'), 4.16 (br s, 1H, H-4'), 4.42-4.43 (m, 1H, H-3'), 4.72-4.78 (m, 2H, CH$_2$N$_3$), 6.24 (dd, J=5.8, 8.2 Hz, H-1'), 6.25 (dd, J=3.5, 8.5 Hz, 2H, H$_{Ar}$), 7.24, 7.25 (2d, J=14.8 Hz, 2×=CH), 7.69-7.86 (m, 4H, H$_{Ar}$, H-6), 8.42 (t, J=13.4 Hz, =CH). $^{31}$P NMR (D$_2$O) δ −4.85 (m, 1P, P$_\gamma$), −9.86 (m, 1P, P$_\alpha$), −20.40 (m, 1P, P$_\beta$). Mass (−ve electrospray) calcd for C$_{49}$H$_{64}$N$_9$O$_{22}$P$_3$S$_4$ 1351.23. found 1372 (M−2H+Na), 1270 [M−80], 1190 [M−160].

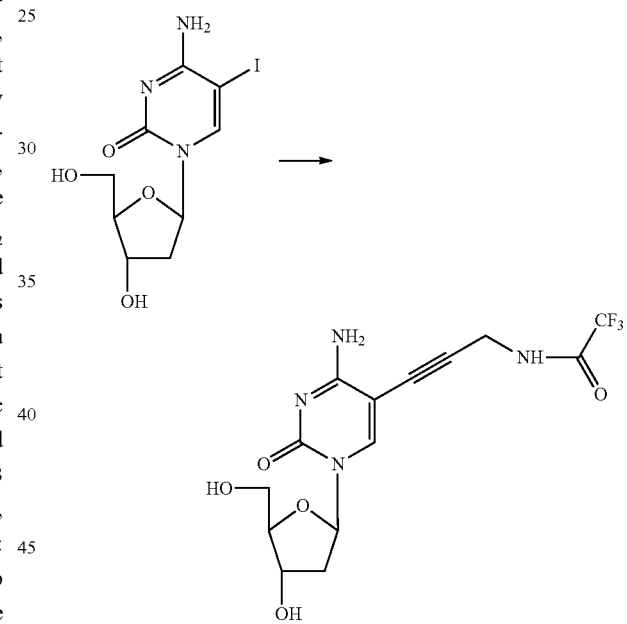

(7)

5-[3-(2,2,2-Trifluoroacetamido)-prop-1-ynyl]-2'-deoxycytidine (7)

To a solution of 5-iodo-2'-deoxycytidine (10 g, 28.32 mmol) in DMF (200 ml) in a light protected round bottom flask under Argon atmosphere, was added CuI (1.08 g, 5.67 mmol), triethylamine (7.80 ml, 55.60 mmol), 2,2,2-trifluoro-N-prop-2-ynyl-acetamide (12.8 g, 84.76 mmol) and at last Pd(PPh$_3$)$_4$ (3.27 g, 2.83 mmol). After 18 hours at room temperature, dowex bicarbonate (20 mg) was added and the mixture was stirred for a further 1 h. Filtration and evaporation of the volatiles under reduced pressure gave a residue that was purified by flash chromatography on silica gel (CH$_2$Cl$_2$, CH$_2$Cl$_2$:EtOAc 1:1, EtOAc:MeOH 9:1). The expected product (7) was obtained as a beige solid in quantitative yield. $^1$H NMR (D$_2$O) δ 2.24-2.17 (m, 1H, H-2'), 2.41-2.37 (m, 1H, H-2'), 3.68 (dd, J=12.5, 5.0 Hz, 1H, H-5'), 3.77 (dd, J=12.5, 3.2 Hz, 1H, H-5'), 3.99 (m, 1H, H-4'), 4.27 (s, 2H, CH$_2$N), 4.34 (m, 1H, H-3'), 6.11 (t, J=6.3 Hz, 1H, H-1'), 8.1 (br s, 1H, NH); MS (ES): m/z (%) (M−H) 375 (100).

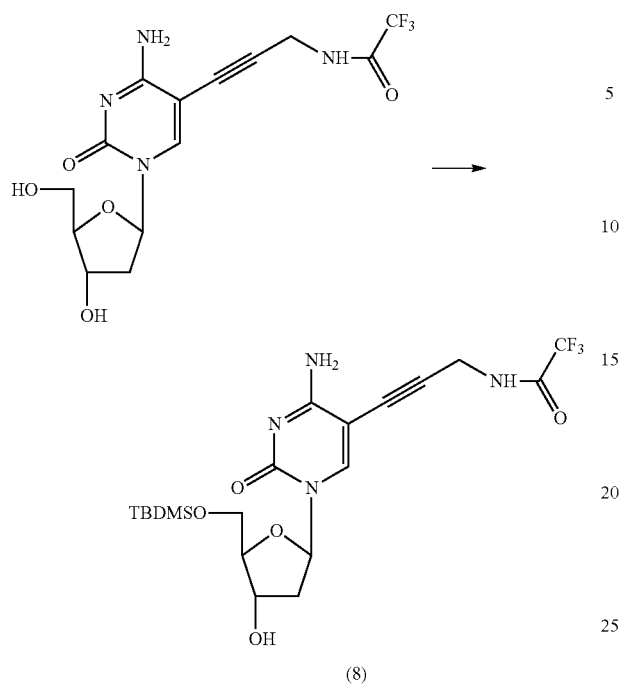

(8)

5'-O-(tert-Butyldimethylsilyl)-5-[3-(2,2,2-trifluoro-acetamido)-prop-1-ynyl]-2'-deoxycytidine (8)

To a solution of the starting material (7) (1.0 g, 2.66 mmol) and imidazole (200 mg, 2.93 mmol) in DMF (3.0 ml) at 0° C., was slowly added TBDMSCl (442 mg, 2.93 mmol) in four portions over 1 h. After 2 h, the volatiles were evaporated under reduced pressure and the residue was adsorbed on silica gel and purified by flash chromatography (EtOAc, EtOAc: MeOH 9.5:0.5). The expected product (8) was isolated as a crystalline solid (826 mg, 64%). $^1$H NMR (d$_6$ DMSO) δ 0.00 (s, 1H, CH$_3$); 0.01 (s, 1H, CH$_3$), 0.79 (s, 9H, tBu), 1.87-1.80 (m, 1H, H-2'), 2.12 (ddd, J=13.0, 5.8 and 3.0 Hz, 1H, H-2'), 3.65 (dd, J=11.5, 2.9 Hz, 1H, H-5'), 3.74 (dd, J=11.5, 2.5 Hz, 1H, H-5'), 3.81-3.80 (m, 1H, H-4'), 4.10-4.09 (m, 1H, H-3'), 4.17 (d, 2H, J=5.1 Hz, NCH$_2$), 5.19 (d, 1H, J=4.0 Hz, 3'-OH), 6.04 (t, J=6.6 Hz, 1H, H-1'), 6.83 (br s, 1H, NHH), 7.78 (br s, 1H, NHH), 7.90 (s, 1H, H-6), 9.86 (t, J=5.1 Hz, 1H, —H$_2$CNH); MS (ES): m/z (%) (MH)$^+$ 491 (40%).

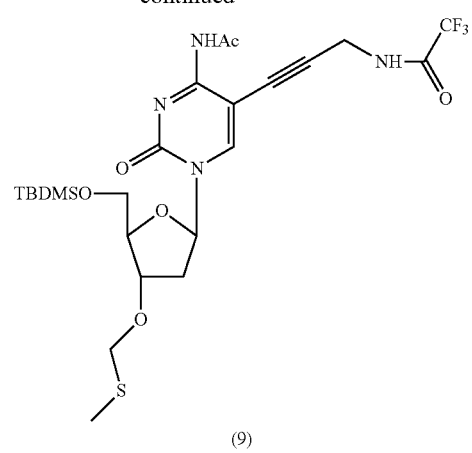

(9)

4-N-Acetyl-5'-O-(tert-butyldimethylsilyl)-3'-O-(methylthiolmethyl)-5-[3-(2,2,2-trifluoroacetamide)-prop-1-ynyl]-2'-deoxycytidine (9)

To a solution of the starting material (8) (825 mg, 1.68 mmol) in DMSO (6.3 ml) and N$_2$ atmosphere, was slowly added acetic acid (AcOH) (1.3 ml, 23.60 mmol) followed by acetic anhydride (Ac$_2$O) (4.8 ml, 50.50 mmol). The solution was stirred at room temperature for 18 h and quenched at 0° C. by addition of saturated NaHCO$_3$ (20 ml). The product was extracted into EtOAc (3×30 ml), organic extracts combined, dried (MgSO$_4$), filtered and the volatiles evaporated. The crude residue was purified by flash chromatography on silica gel (EtOAc:petroleum ether 1:1) to give the expected product as a colourless oil (9) (573 mg, 62%). $^1$H NMR (d$_6$ DMSO) δ 0.00 (s, 6H, 2×CH$_3$), 0.78 (s, 9H, tBu), 2.01 (s, 3H, SCH$_2$), 2.19-1.97 (m, 2H, 2×H2'), 2.25 (s, 3H, COCH$_2$), 3.67 (dd, 1H, J=11.5 Hz, H-5'), 3.78 (dd, 1H, J=11.5, 3.3 Hz, H-5'), 4.06-4.05 (m, 1H, H-4'), 4.17 (d, 2H, J=5.1 Hz, N—CH$_2$), 4.30-4.28 (m, 1H, H-3'), 4.63 (s, 2H; CH$_2$—S), 5.94 (t, 1H, J=6.5 Hz, H-1'), 8.17 (s, 1H, H-6), 9.32 (s, 1H, NHCO), 9.91 (t, 1H, J=5.4 Hz, NHCH$_2$); MS (ES): m/z (%) (MH)$^+$ 593.

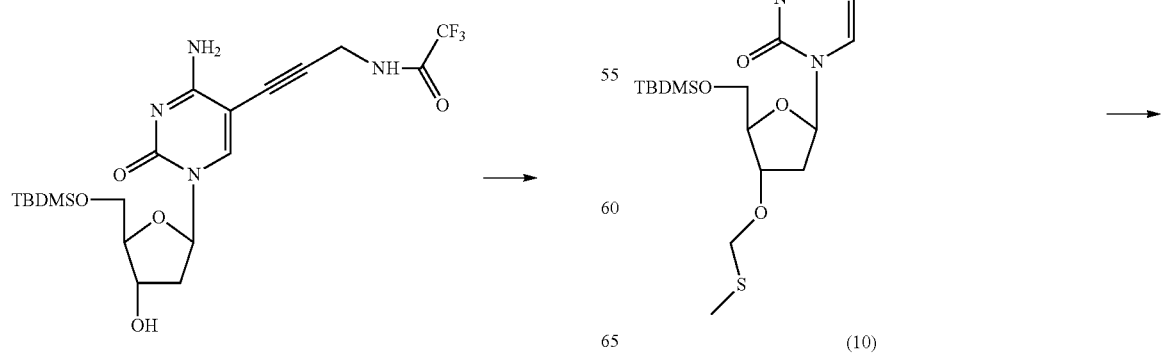

(10)

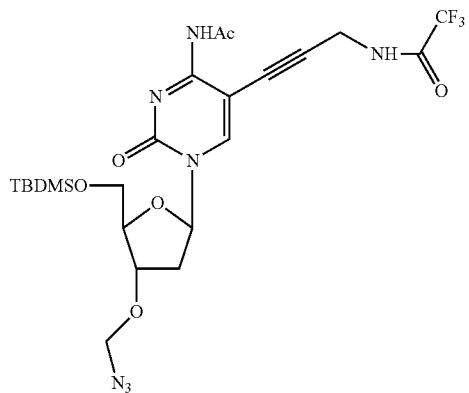

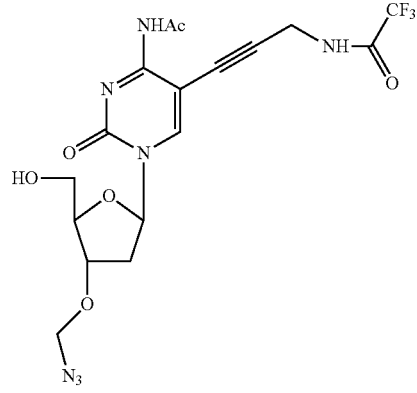

(11)

4-N-Acetyl-3'-O-(azidomethyl)-5'-O-(tert-butyldim-ethylsilyl)-5-[3-(2,2,2-trifluoroacetamide)-prop-1-ynyl]-2'-deoxycytidine (10)

To a solution of the starting material (9) (470 mg, 0.85 mmol) in dichloromethane (DCM) (8 ml) under $N_2$ atmosphere and cooled to 0° C., was added cyclohexene (430 μl, 4.27 mmol) followed by $SO_2Cl_2$ (1 M in DCM, 1.0 ml, 1.02 mmol). The solution was stirred for 30 minutes at 0° C., and the volatiles were evaporated. Residue immediately dissolved in DMF (8 ml) stirred under $N_2$ and sodium azide (275 mg, 4.27 mmol) slowly added. After 18 h, the crude product was evaporated to dryness, dissolved in EtOAc (30 ml) and washed with $Na_2CO_3$ (3×5 ml). The combined organic layer was kept separately. A second extraction of the product from the aqueous layer was performed with DCM (3×10 ml). All the combined organic layers were dried ($MgSO_4$), filtered and the volatiles evaporated under reduced pressure to give an oil identified as the expected product (10) (471 mg, 94% yield). This was used without any further purification. $^1$H NMR ($d_6$ DMSO) δ 0.11 (s, 3H, $CH_3$), 0.11 (s, 3H, $CH_3$), 0.88 (s, 9H, $^t$Bu), 2.16-2.25 (m, 1H, H-2'), 2.35 (s, 3H, $COCH_3$), 2.47-2.58 (m, 1H, H-2'), 3.79 (dd, J=11.6, 3.2 Hz, 1H, H-5'), 3.90 (dd, J=11.6, 3.0 Hz, 1H, H-5'), 4.17-4.19 (m, 1H, H-4'), 4.28 (s, 2H, $NCH_2$), 4.32-4.35 (m, 1H, H-3'), 4.89 (dd, J=14.4, 6.0 Hz, 2H, $CH_2$—$N_3$), 6.05 (t, J=6.4 Hz, 1H, H-1'), 8.25 (s, 1H, H-6), 9.46 (br s, 1H, NHH), 10.01 (br s, 1H, NHH).

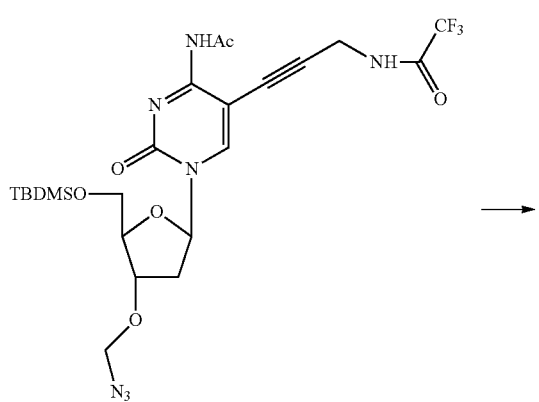

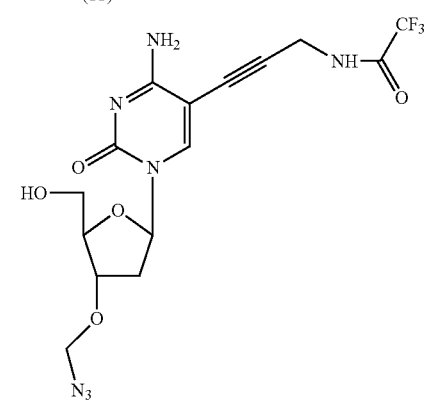

(12)

4-N-Acetyl-3'-O-(azidomethyl)-5-[3-(2,2,2-trifluoro-acetamido)-prop-1-ynyl]-2'-deoxycytidine and 3'-O-(Azidomethyl)-5-[3-(2,2,2-trifluoroacetamido)-prop-1-ynyl]-2'-deoxycytidine (11)

To a solution of the starting material (11) (440 mg, 0.75 mmol) in THF (20 ml) at 0° C. and $N_2$ atmosphere, was added TBAF in THF 1.0 M (0.82 ml, 0.82 mmol). After 1.5 h, the volatiles were evaporated under reduced pressure and the residue purified by flash chromatography on silica gel (EtOAc:petroleum ether 8:2 to EtOAc 100% to EtOAc: MeOH 8:2). Two compounds were isolated and identified as above described. The first eluted 4-N-Acetyl (11), (53 mg, 15%) and, the second one 4-$NH_2$ (12) (271 mg, 84%).

Compound 4-N-Acetyl (11): $^1$H NMR ($d_6$ DMSO) δ 1.98 (s, 3H, $CH_3CO$), 2.14-2.20 (m, 2H, HH-2'), 3.48-3.55 (m, 1H, H-5'), 3.57-3.63 (m, 1H, H-5'), 3.96-4.00 (m, 1H, H-4'), 4.19 (d, J=5.3 Hz, 2H, $CH_2$—NH), 4.23-4.28 (m, 1H, H-3'), 4.77 (s, 2H, $CH_2$—$N_3$), 5.2 (t, 1H, J=5.1 Hz, 5'-OH), 5.95 (t, J=6.2 Hz, 1H, H-1'), 8.43 (s, 1H, H-6), 9.34 (s, 1H, CONH), 9.95 (t, J=5.3 Hz, 1H, $NHCH_2$).

Compound 4-$NH_2$ (12): $^1$H NMR ($d_6$ DMSO) δ 1.98-2.07 (2H, CHH-2'), 3.50-3.63 (m, 2H, CHH-5'), 3.96-4.00 (m, 1H, H-4'), 4.09 (d, J=5.3 Hz, 2H, $CH_2$—NH), 4.24-4.28 (m, 1H, H-3'), 4.76 (s, 2H, $CH_2$—$N_3$), 5.13 (t, J=5.3 Hz, 1H, 5'-OH), 5.91 (br s, 1H, NHH), 6.11 (t, J=6.4 Hz, 1H, H-1'), 8.20 (t, J=5.3 Hz, 1H, $NCH_2$), 8.45 (s, 1H, H-6), 11.04 (br s, 1H, NHH).

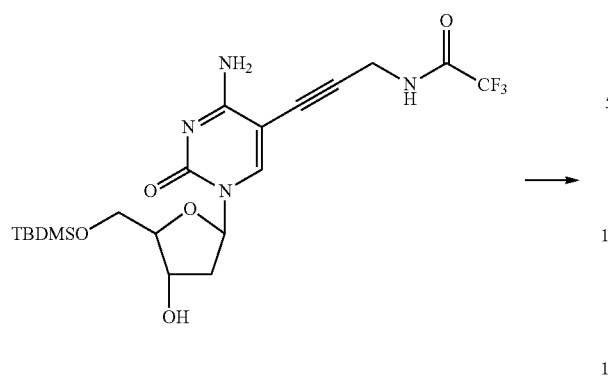

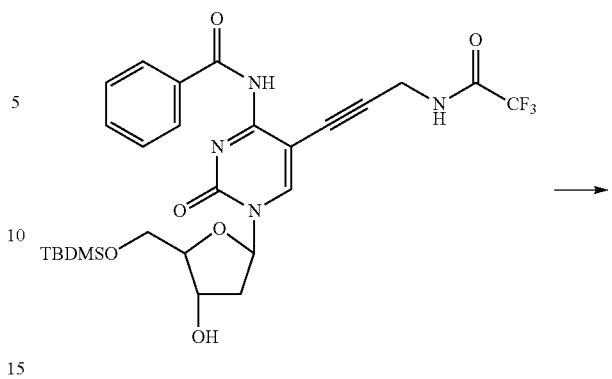

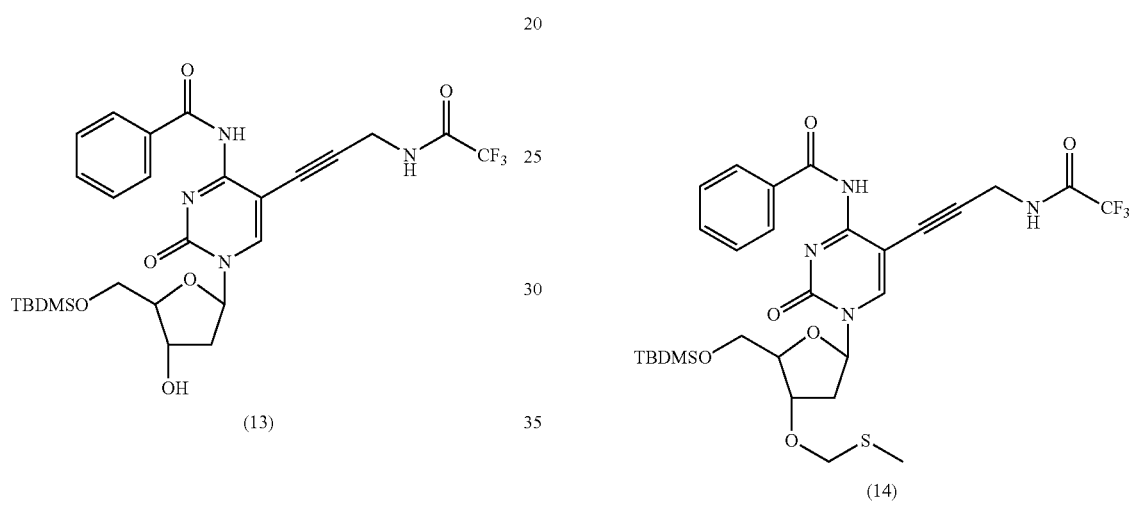

4-N-Benzoyl-5'-O-(tert-butyldimethylsilyl)-5-[3-(2,2,2-trifluoroacetamido)-prop-1-ynyl]-2'-deoxycytidine (13)

The starting material (8) (10 g, 20.43 mmol) was azeotroped in dry pyridine (2×100 ml) then dissolved in dry pyridine (160 ml) under $N_2$ atmosphere. Chlorotrimethylsilane (10 ml, 79.07 mmol) added drop wise to the solution and stirred for 2 hours at room temperature. Benzoyl chloride (2.6 ml, 22.40 mmol) was then added to solution and stirred for one further hour. The reaction mixture was cooled to 0° C., distilled water (50 ml) added slowly to the solution and stirred for 30 minutes. Pyridine and water were evaporated from mixture under high vacuum to yield a brown gel that was portioned between 100 ml of sat. aq. $NaHCO_3$ (100 ml) solution DCM. The organic phase was separated and the aqueous phase extracted with a further (2×100 ml) of DCM. The organic layers were combined, dried ($MgSO_4$), filtered and the volatiles evaporated under reduced pressure. The resulting brown oil was purified by flash chromatography on silica gel (DCM:MeOH 99:1 to 95:5) to yield a light yellow crystalline solid (13) (8.92 g, 74%). $^1$H NMR ($d_6$ DMSO): δ 0.00 (s, 6H, $CH_3$), 0.78 (s, 9H, tBu), 1.94 (m, 1H, H-2'), 2.27 (m, 1H, H-2'), 3.64 (d, 1H, J=11.6 Hz, H-5'), 3.75 (d, 1H, J=11.6 Hz, H-5'), 3.91 (m, 1H, H-4'), 4.09 (br m, 3H, $CH_2NH$, H-3'), 5.24 (s, 1H, 3'-OH), 6.00 (m, 1H, H-1'), 7.39 (m, 2H, Ph), 7.52 (m, 2H, Ph), 7.86 (m, 1H, Ph), 8.0 (s, 1H, H-6), 9.79 (t, 1H, J=5.4 Hz, $NHCH_2$), 12.67 (br s, 1H, NH). Mass (+ve electrospray) calcd for $C_{27}H_{33}F_3N_4O_6Si$ 594.67. found 595.

4-N-Benzoyl-5'-O-(tert-butyldimethylsilyl)-3'-O-methylthiomethyl-5-[3-(2,2,2-trifluoroacetamido)-prop-1-ynyl]-2'-deoxycytidine (14)

The starting material (13) (2.85 g, 4.79 mmol) was dissolved in dry DMSO (40 ml) under $N_2$ atmosphere. Acetic acid (2.7 ml, 47.9 mmol) and acetic anhydride (14.4 ml, 143.7 mmol) were added sequentially and slowly to the starting material, which was then stirred for 18 h at room temperature. Saturated $NaHCO_3$ (150 ml) solution was carefully added to the reaction mixture. The aqueous layer was extracted with EtOAc (3×150 ml). The organic layers were combined, dried ($MgSO_4$) filtered and evaporated to yield an orange liquid that was subsequently azeotroped with toluene (4×150 ml) until material solidified. Crude residue purified on silica gel (petroleum ether:EtOAc 3:1 to 2:1) to yield a yellow crystalline solid (14) (1.58 g, 50%). $^1$H NMR ($d_6$ DMSO): δ 0.00 (s, 6H, $CH_3$), 0.78 (s, 9H, tBu), 1.99 (s, 3H, $CH_3$), 2.09 (m, 1H, H-2'), 2.28 (m, 1H, H-2'), 3.66 (d, 1H, J=11.5, 2.9 Hz, H-5'), 3.74 (dd, 1H, J=11.3, 2.9 Hz, H-5'), 3.99 (m, 1H, H-4'), 4.09 (m, 1H, $CH_2NH$), 4.29 (m, 1H, H-3'), 4.61 (s, 2H, $CH_2S$), 6.00 (m, 1H, H-1'), 7.37 (m, 2H, Ph), 7.50 (m, 2H, Ph), 7.80 (d, 1H, J=7.55 Hz, $H_{Ar}$), 7.97 (s, 1H, H-6), 9.79 (br t, 1H, $NHCH_2$), 12.64 (br s, 1H, NH). Mass (−ve electrospray) calcd for $C_{29}H_{37}F_3N_4O_6SSi$ 654.79. found 653.2.

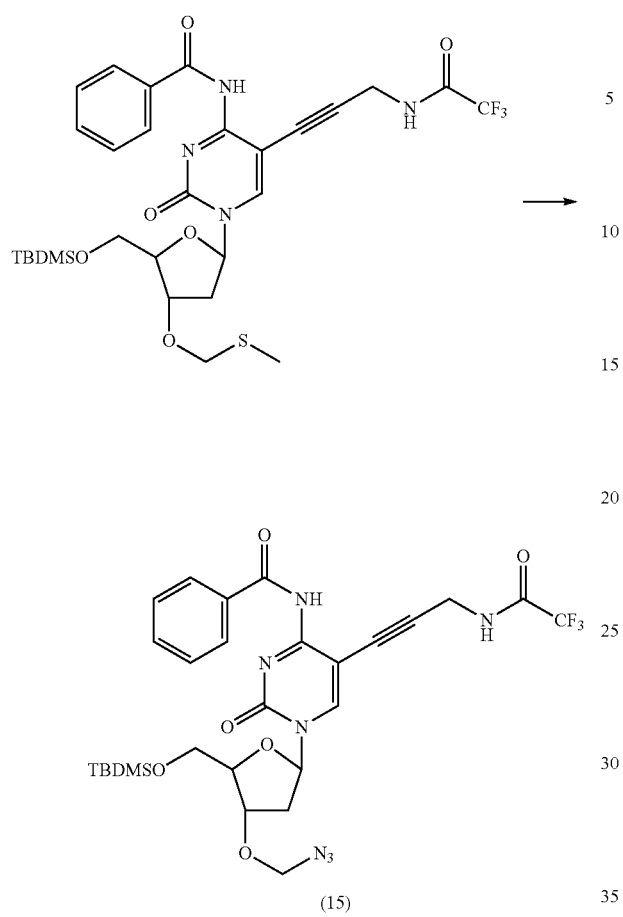

(15)

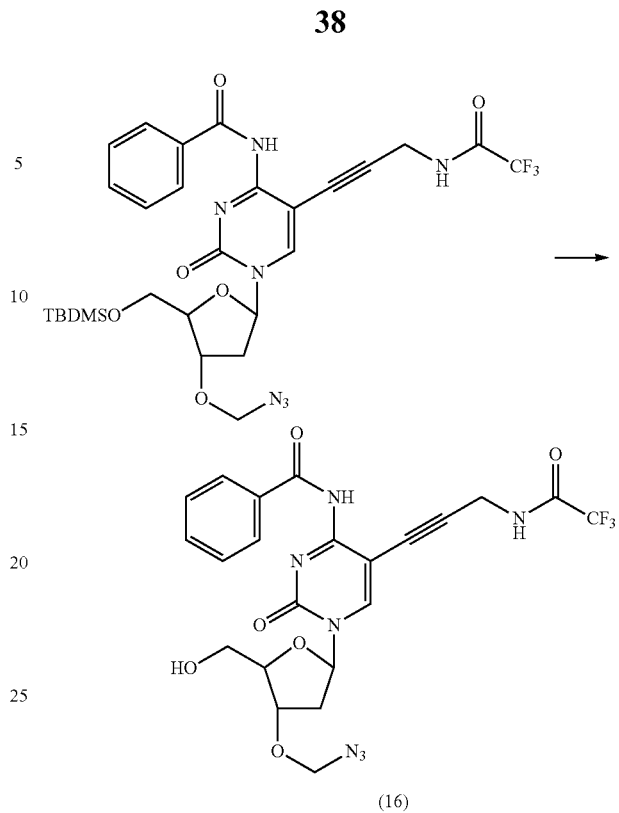

(16)

4-N-Benzoyl-5'-O-(tert-butyldimethylsilyl)-3'-O-azidomethyl-5-[3-(2,2,2-trifluoroacetamido)-prop-1-ynyl]-2'-deoxycytidine (15)

The starting material (14) (1.65 g, 2.99 mmol) was dissolved in DCM (18 ml) and cooled to 0° C. Cyclohexene (1.5 ml, 14.95 mmol) and $SO_2Cl_2$ (0.72 ml, 8.97 mmol) were added and stirred 1 h in ice bath. TLC indicated starting material still to be present whereupon a further aliquot of $SO_2Cl_2$ (0.24 ml) was added and the mixture stirred for 1 h at 0° C. Volatiles were removed by evaporation to yield a light brown solid that was redissolved in 18 ml of dry DMF (18 ml) under $N_2$. Sodium azide (0.97 g, 14.95 mmol) was then added to the solution and stirred for 2.5 h at room temperature. The reaction mixture was passed through a pad of silica and eluted with EtOAc and the volatiles removed by high vacuum evaporation. The resulting brown gel was purified by flash chromatography (petroleum ether:EtOAc 4:1 to 2:1) to yield the desired product as a white crystalline solid (15) (0.9 g, 55%). $^1$H NMR ($d_6$ DMSO): δ 0.00 (s, 6H, $CH_3$), 0.78 (s, 9H, tBu), 2.16 (m, 1H, H-2'), 2.22 (m, 1H, H-2'), 3.70 (d, 1H, J=11.5 Hz, H-5'), 3.75 (d, 1H, J=11.3 Hz, H-5'), 4.01 (m, 1H, H-4'), 4.10 (m, 1H, $CH_2NH$), 4.23 (m, 1H, H-3'), 4.76 (s, 2H, $CH_2S$), 5.99 (m, 1H, H-1'), 7.37 (m, 2H, Ph), 7.50 (m, 2H, Ph), 7.81 (d, 1H, J=7.4 Hz, Ph), 7.95 (s, 1H, H-6), 9.78 (br s, 1H, $NHCH_2$), 12.64 (br s, 1H, NH). Mass (−ve electrospray) calcd for $C_{28}H_{34}F_3N_7O_6Si$ 649.71. found 648.2.

4-N-Benzoyl-3'-O-azidomethyl-5-[3-(2,2,2-trifluoroacetamido)-prop-1-ynyl]-2'-deoxycytidine (16)

The starting material (15) (140 mg, 0.22 mmol) was dissolved in THF (7.5 ml). TBAF (1M soln. in THF, 0.25 ml) was added slowly and stirred for 2 h at room temperature. Volatile material removed under reduced pressure to yield a brown gel that was purified by flash chromatography (EtOAc:DCM 7:3) to yield the desired product (16) as a light coloured crystalline solid (0.9 g, 76%). $^1$H NMR ($d_6$ DMSO): δ2.16 (m, 1H, H-2'), 2.22 (m, 1H, H-2'), 3.70 (d, 1H, J=11.5 Hz, H-5'), 3.75 (d, 1H, J=11.3 Hz, H-5'), 4.01 (m, 1H, H-4'), 4.10 (m, 1H, $CH_2NH$), 4.23 (m, 1H, H-3'), 4.76 (s, 2H, $CH_2S$), 5.32 (s, 1H, 5' OH), 5.99 (m, 1H, H-1'), 7.37 (m, 2H, Ph), 7.50 (m, 2H, Ph), 7.81 (d, 1H, J=7.35 Hz, Ph), 7.95 (s, 1H, H-6), 9.78 (br s, 1H, $NHCH_2$), 12.64 (br s, 1H, NH). Mass (−ve electrospray) calcd for $C_{22}H_{20}F_3N_7O_6$ 535.44. found 534.

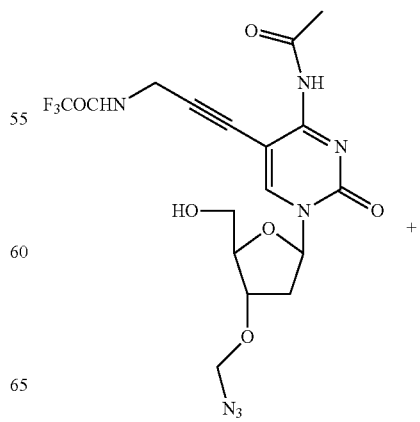

+

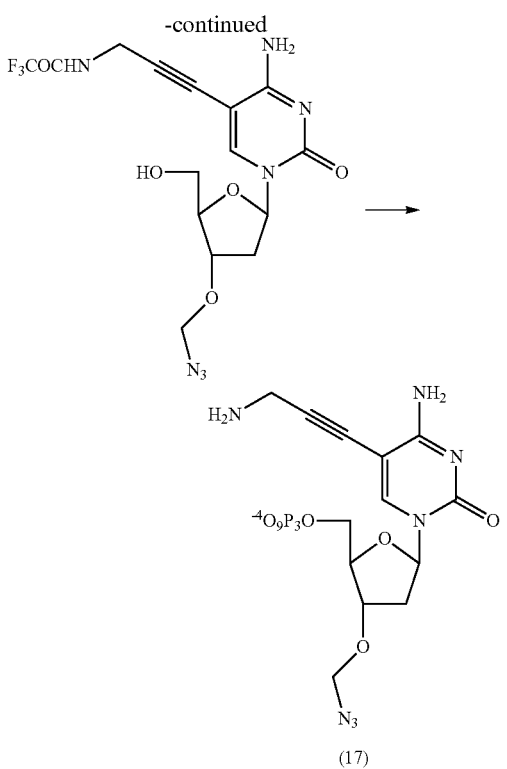

5-(3-Amino-prop-1-ynyl)-3'-O-azidomethyl-2'-deoxycytidine 5'-O-nucleoside triphosphate (17)

To a solution of (11) and (12) (290 mg, 0.67 mmol) and proton sponge (175 mg, 0.82 mmol) (both previously dried under $P_2O_5$ for at least 24 h) in $PO(OMe)_3$ (600 μl), at 0° C. under Argon atmosphere, was slowly added $POCl_2$ (freshly distilled) (82 μl, 0.88 mmol). The solution was vigorously stirred for 3 h at 0° C. and then quenched by addition of tetra-tributylammonium diphosphate (0.5 M) in DMF (5.2 ml, 2.60 mmol), followed by $nBu_3N$ (1.23 ml, 5.20 mmol) and triethylammonium bicarbonate (TEAB) 0.1 M (20 ml). After 1 h at room temperature aqueous ammonia solution (ρ 0.88, 20 ml) was added to the mixture. Solution stirred at room temperature for 15 h, volatiles evaporated under reduced pressure and the residue was purified by MPLC with a gradient of TEAB from 0.05M to 0.7M. The expected triphosphate was eluted from the column at approx. 0.60 M TEAB. A second purification was done by HPLC in a Zorbax SB-C18 column (21.2 mm i.d.×25 cm) eluted with 0.1M TEAB (pump A) and 30% $CH_3CN$ in 0.1M TEAB (pump B) using a gradient as follows: 0-5 min 5% B, Φ.2 ml; 5-25 min 80% B, Φ.8 ml; 25-27 min 95% B, Φ.8 ml; 27-30 min 95% B, Φ.8 ml; 30-32 min 5% B, Φ.8 ml; 32-35 min 95% B, Φ.2 ml, affording the product described above with a $r_t$(17): 20.8 (14.5 μmols, 2.5% yield); $^{31}P$ NMR ($D_2O$, 162 MHz) δ 5.59 (d, J=20.1 Hz, $P_\chi$), −10.25 (d, J=19.3 Hz, 1P, $P_\alpha$), −20.96 (t, J=19.5 Hz, 1P, $P_\beta$); $^1H$ NMR ($D_2O$) δ 2.47-2.54 (m, 1H, H-2'), 2.20-2.27 (m, 1H, H-2'), 3.88 (s, 2H, $CH_2N$), 4.04-4.12 (m, 1H, HH-5'), 4.16-4.22 (m, 1H, HH-5'), 4.24-4.30 (m, 1H, H-4'), 4.44-4.48 (m, 1H, H-3'), 6.13 (t, J=6.3 Hz, 1H, H-1'), 8.35 (s, 1H, H-6); MS (ES): m/z (%) (M−H) 574 (73%), 494 (100%).

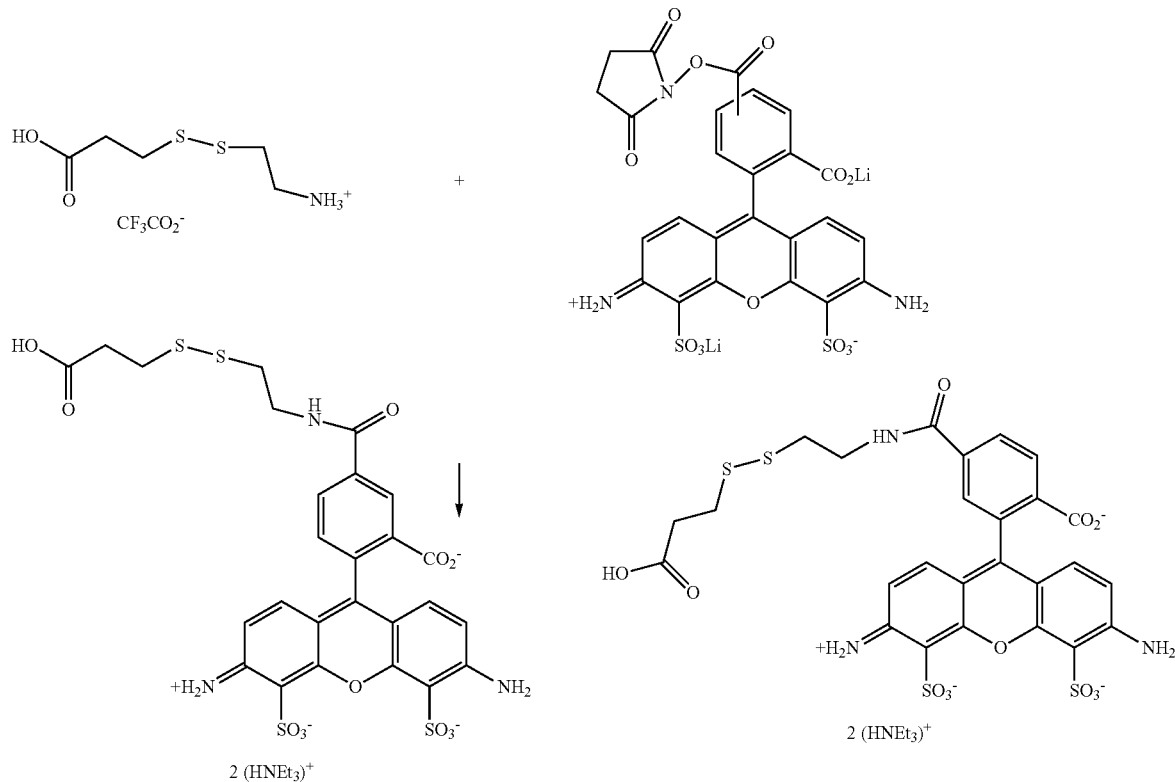

Alexa488 Disulfide Linker

Commercial available Alexa Fluor 488-NHS (35 mg, 54 µmol) was dissolved in DMF (700 µL) and, to ensure full activation, 4-DMAP (7 mg, 59 µmol) and N,N'-disuccinimidyl carbonate (15 mg, 59 µmol) were sequentially added. After 15 min on complete activation, a solution of the starting disulfide (32.0 mg, 108 µmol) in DMF (300 µL) containing diisopropylethylamine (4 µL) was added over the solution of the activated dye. Further addition of diisopropylethylamine (20 µL) to the final mixture was done, ultrasonicated for 5 min and reacted for 18 h at room temperature in the darkness. The volatiles were evaporated under reduced pressure and the crude residue was first purified passing it through a short ion exchange resin Sephadex-DEAE A-25 (40-120µ) column, first eluted with TEAB 0.1 M (25 ml) then 1.0 M TEAB (75 ml). The latest containing the two final compounds was concentrated and the residue was HPLC purified in a Zorbax SB-C18 column (21.2 mm i.d.×25 cm) eluted with 0.1M TEAB (pump A) and CH$_3$CN (pump B) using a gradient as follows: 0-2 min 2% B, Φ.2 ml; 2-4 min 2% B, Φ.8 ml; 4-15 min 23% B, Φ.8 ml; 15-24 min 23% B, Φ.8 ml; 24-26 min 95% B, Φ.8 ml; 26-28 min 95% B, Φ.8 ml, 28-30 min 2% B, Φ.8 ml, 30-33 min 2% B, Φ.2 ml affording both compounds detailed above with t$_r$: 19.0 (left regioisomer) and t$_r$: 19.5 (right regioisomer). Both regioisomers were respectively passed through a dowex ion exchange resin column, affording respectively 16.2 µmol and 10.0 µmol, 62% total yield (based in commercial available Alexa Fluor 488-NHS of 76% purity); $\epsilon_{493}$=71,000 cm$^{-1}$ M$^{-1}$ in H$_2$O. $^1$H NMR (D$_2$O) (left regioisomer) δ 2.51 (t, J=6.8 Hz, 2H, CH$_2$), 2.66 (t, J=6.8 Hz, 2H, CH$_2$), 2.71 (t, J=5.8 Hz, 2H, CH$_2$), 3.43 (t, J=5.8 Hz, 2H, CH$_2$), 6.64 (d, J=9.2 Hz, 2H, H$_{Ar}$), 6.77 (d, J=9.2 Hz, 2H, H$_{Ar}$), 7.46 (s, 1H, H$_{Ar}$), 7.90 (dd, J=8.1 and 1.5 Hz, 1H, H$_{Ar}$), 8.20 (d, J=8.1 Hz, 1H, H$_{Ar}$). $^1$H NMR (D$_2$O) (right regioisomer) δ 2.67 (t, J=6.8 Hz, 2H, CH$_2$), 2.82 (t, J=6.8 Hz, 2H, CH$_2$), 2.93 (t, J=6.1 Hz, 2H, CH$_2$), 3.68 (t, J=6.1 Hz, 2H, CH$_2$), 6.72 (d, J=9.3 Hz, 2H, H$_{Ar}$), 6.90 (d, J=9.3 Hz, 2H, H$_{Ar}$), 7.32 (d, J=7.9 Hz, 1H, H$_{Ar}$), 8.03 (dd, J=7.9, 1.7 Hz, 1H, H$_{Ar}$), 8.50 (d, J=1.8 Hz, 1H, H$_{Ar}$) Mass (-ve electrospray) calcd for C$_{26}$H$_{23}$N$_3$O$_{12}$S$_4$ 697.02. found 692 (M-H), 347 [M/2].

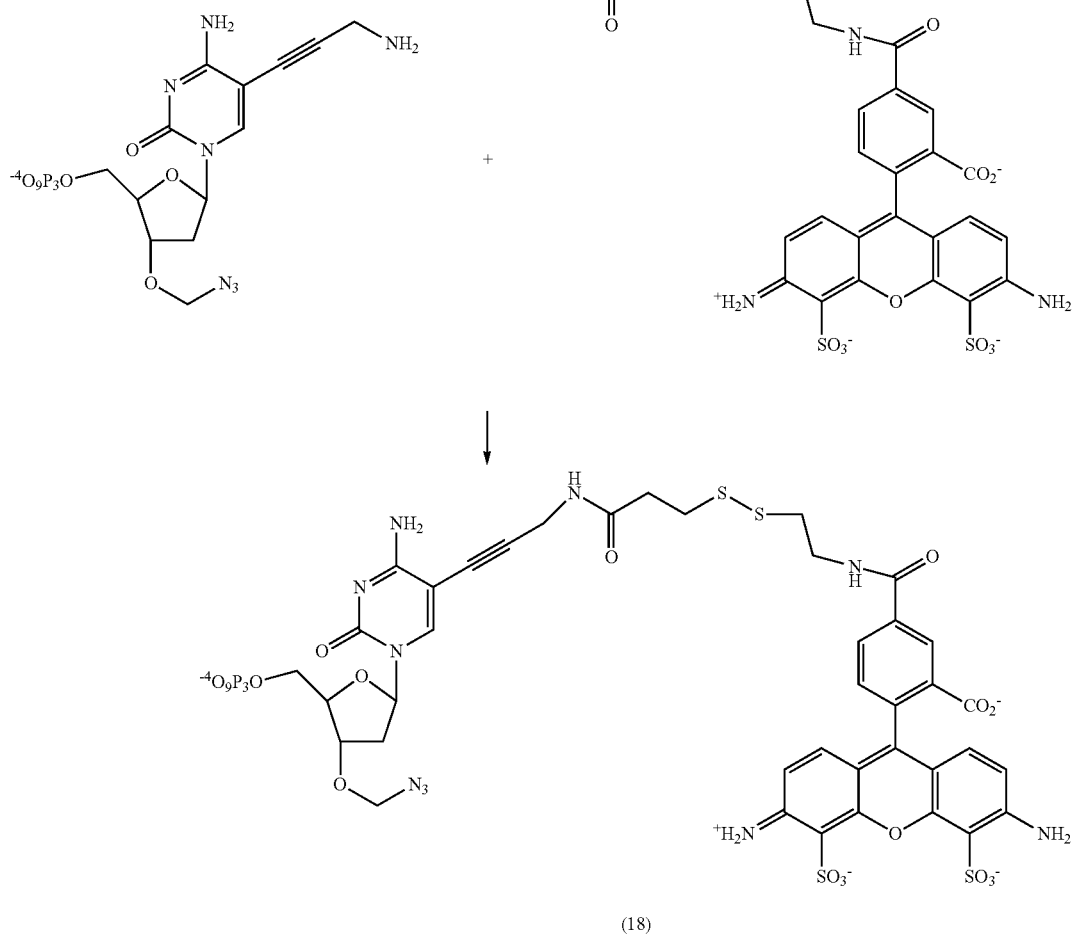

(18)

To a solution of Alexa Fluor 488 disulfide linker (3.4 µmol, 2.37 mg) in DMF (200 µL) was added 4-DMAP (0.75 mg, 5.1 µmol) and N,N-disuccinimidyl carbonate (1.70 mg, 5.1 µmol). The mixture was stirred for 15 to full activation of the acid, then it was added into the solution of the nucleotide (17) (3.45 mg, 6.0 µmol) in DMF (0.3 ml) containing nBu$_3$N (40 µL) at 0° C. The mixture was sonicated for 3 min and then continuously stirred for 16 h in the absence of light. The volatiles were evaporated under reduced pressure and the residue was firstly purified by filtration through a short ion exchange resin Sephadex-DEAE A-25 column, first eluted with TEAB 0.1 M (50 ml) removing the unreacted dye-linker, then 1.0 M TEAB (100 ml) to collect the expected product (18). After concentration and the residue was HPLC purified in a Zorbax SB-C18 column (21.2 mm i.d.×25 cm) eluted with 0.1M TEAB (pump A) and CH$_3$CN (pump B) using a gradient as follows: 0-2 min 2% B, 2 ml; 2-4 min 2% B, Φ.8 ml; 4-15 min 23% B, Φ.8 ml; 15-24 min 23% B, Φ.8 ml; 24-26 min 95% B, Φ.8 ml; 26-28 min 95% B, Φ.8 ml, 28-30 min 2% B, Φ.8 ml, 30-33 min 2% B, Φ.2 ml affording the product detailed above with a r$_f$(18): 19.8 (0.26 μmols, 12% yield based on UV measurement); λ$_{max}$=493 nm, ∈ 71,000 cm$^{-1}$ M$^{-1}$ in H$_2$O); $^{31}$P NMR (D$_2$O, 162 MHz) δ-5.06 (d, J=20.6 Hz, 1P, P$_\gamma$), −10.25 (d, J=19.3 Hz, 1P, P$_\alpha$), −21.21 (t, J=19.5 Hz, 1P, P$_\beta$); $^1$H NMR (D$_2$O) δ 2.09-2.17 (m, 1H, HH-2'), 2.43-2.50 (m, 1H, HH-2'), 2.61 (t, J=6.8 Hz, 2H, H$_2$C—S), 2.83 (2H, S—CH$_2$), 3.68 (t, J=6.0 Hz, 2H, ArCONCH$_2$), 4.06 (s, 2H, CH$_2$N), 4.08-4.17 (m, 4H, HH-5'), 4.25-4.29 (m, 1H, H-4'), 4.46-4.50 (m, 1H, H-3'), 6.09 (t, J=6.4 Hz, 1H, H-1'), 6.88 (d, J=9.1 Hz, 1H, H$_{Ar}$), 6.89 (d, J=9.3 Hz, 1H, H$_{Ar}$), 7.15 (d, J=9.3 Hz, 1H, H$_{Ar}$), 7.17 (d, J=9.1 Hz, 1H, H$_{Ar}$), 7.64 (br s, 1H, H$_{Ar}$), 8.00-7.94 (m, 2H, H$_{Ar}$), 8.04 (s, 1H, H-6); MS (ES): m/z (%) (M−H) 1253 (46%), (M−H+Na)$^-$ 1275 (100%).

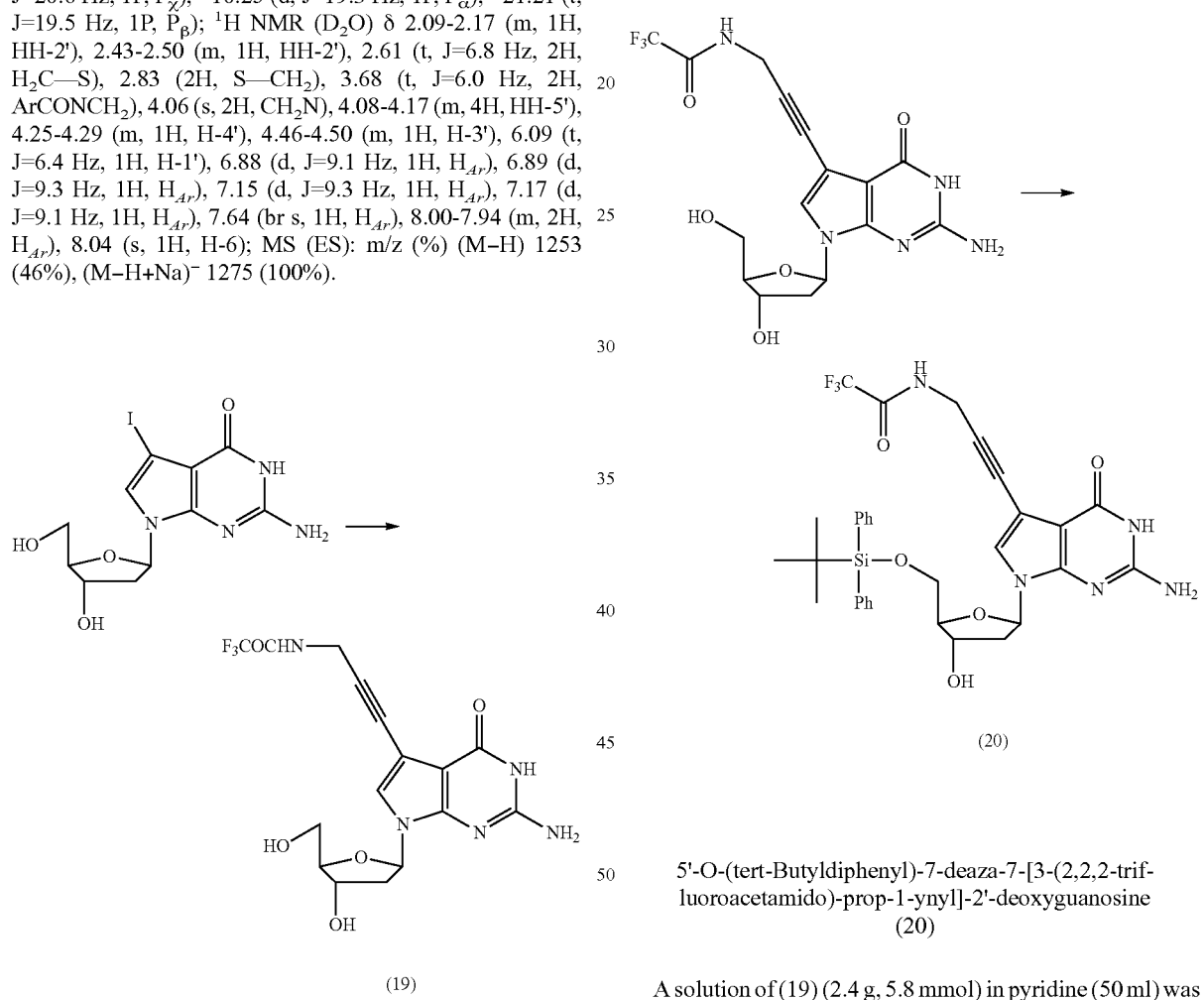

(19)

7-Deaza-[3-(2,2,2-trifluoroacetamido)-prop-1-ynyl]-2'-deoxyguanosine (19)

Under N$_2$, a suspension of 7-deaza-7-iodo-guanosine (2 g, 2.75 mmol), Pd(PPh$_3$)$_4$ (582 mg, 0.55 mmol), CuI (210 mg, 1.1 mmol), Et$_3$N (1.52 ml, 11 mmol) and the propagylamine (2.5 g, 16.5 mmol) in DMF (40 ml) was stirred at room temperature for 15 h under N$_2$. The reaction was protected from light with aluminium foil. After TLC indicating the full consumption of starting material, the reaction mixture was concentrated. The residue was diluted with MeOH (20 ml) and treated with dowex-HCO$_3$$^-$. The mixture was stirring for 30 min and filtered. The solution was concentrated and purified by silica gel chromatography (petroleum ether:EtOAc 50:50 to petroleum ether:EtOAc:MeOH 40:40:20), giving (19) as a yellow powder (2.1 g, 92%). $^1$H NMR (d$_6$ DMSO) δ 2.07-2.11 (m, 1H, H-2'), 2.31-2.33 (m, 1H, H-2'), 3.49-3.53 (m, 2H, H-5'), 3.77 (br s, 1H, H-4'), 4.25 (d, J=4.3 Hz, 2H, ≡CCH$_2$), 4.30 (br s, 1H, H-3'), 4.95 (t, J=5.2 Hz, 1H, 5'-OH), 5.25 (d, J=3.4 Hz, 1H, 3'-OH), 6.27-6.31 (m, 1H, H-1'), 6.37 (s, 2H, NH$_2$), 7.31 (s, 1H, H-8), 10.10 (br s, 1H, NHCOCF$_2$), 10.55 (s, 1H, NH). Mass (−ve electrospray) calcd for C$_{16}$H$_{16}$F$_3$N$_5$O$_5$ 415. found 414.

5'-O-(tert-Butyldiphenyl)-7-deaza-7-[3-(2,2,2-trifluoroacetamido)-prop-1-ynyl]-2'-deoxyguanosine (20)

A solution of (19) (2.4 g, 5.8 mmol) in pyridine (50 ml) was treated with tert-butyldiphenylsilyl chloride (TBDPSCl) (1.65 ml, 6.3 mmol) drop wise at 0° C. The reaction mixture was then warmed to room temperature. After 4 h, another portion of TBDPSCl (260 μL, 1 mmol) was added. The reaction was monitored by TLC, until full consumption of the starting material. The reaction was quenched with MeOH (~5 ml) and evaporated to dryness. The residue was dissolved in DCM and aq. sat. NaHCO$_3$ was added. The aqueous layer was extracted with DCM three times. The combined organic extracts were dried (MgSO$_4$) and concentrated under vacuum. Purification by chromatography on silica (EtOAc to EtOAc:MeOH 85:15) gave (20) a yellow foam (3.1 g, 82%).

$^1$H NMR (d$_6$ DMSO) δ 1.07 (s, 9H, CH$_3$), 2.19-2.23 (m, 1H, H-2'), 2.38-2.43 (m, 1H, H-2'), 3.73-3.93 (m, 2H, H-5'), 4.29 (d, J=5.0 Hz, 2H, CH$_2$N), 4.42-4.43 (m, 1H, H-3'), 5.41 (br s, 1H, OH), 6.37 (t, J=6.5 Hz, H-1'), 6.45 (br s, 2H, NH$_2$), 7.24-7.71 (m, 11H, H-8, H$_{Ar}$), 10.12 (t, J=3.6 Hz, 1H, NH), 10.62 (s, 1H, H-3). Mass (+ve electrospray) calcd for C$_{32}$H$_{34}$F$_3$N$_5$O$_5$Si 653. found 654.

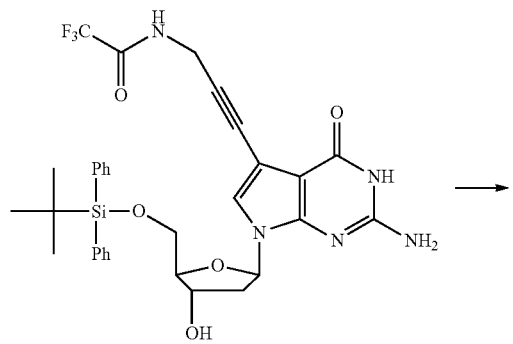

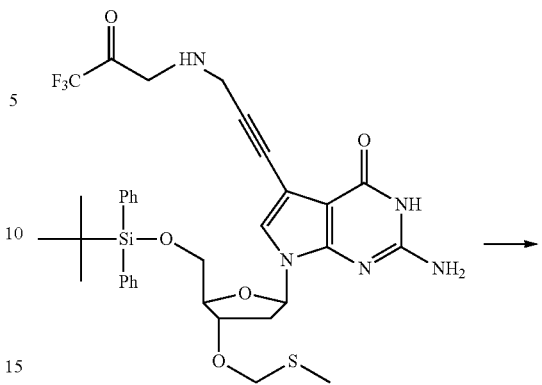

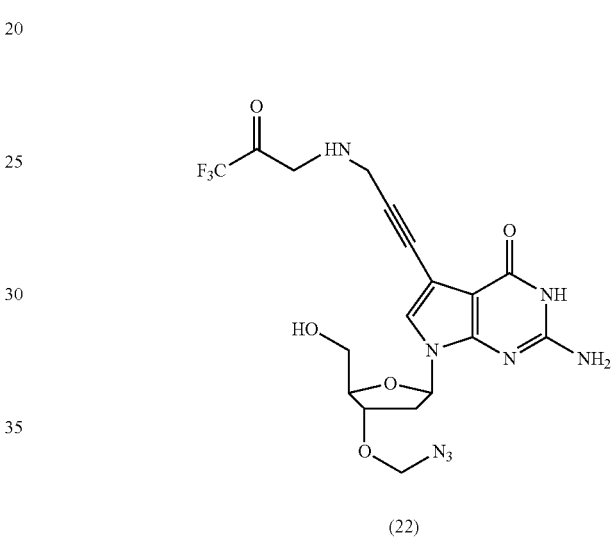

5'-O-(tert-Butyldiphenyl)-7-deaza-3'-O-methylthiol-methyl-7-[3-(2,2,2-trifluoroacetamido)-prop-1-ynyl]-2'-deoxyguanosine (21)

A solution of (20) (1.97 g, 3.0 mmol) in DMSO (15 ml) was treated with Ac$_2$O (8.5 ml, 90 mmol), and AcOH (2.4 ml, 42 mmol) and stirred at room temperature for 15 h, then 2 h at 40° C. The reaction mixture was diluted with EtOAc (200 ml) and stirred with sat, aq. NaHCO$_3$ (200 ml) for 1 h. The aqueous layer was washed with EtOAc twice. The organic layer was combined, dried (MgSO$_4$) and concentrated under vacuum. Purification by chromatography on silica (EtOAc:Hexane 1:1 to EtOAc:Hexane:MeOH 10:10:1) gave (21) as a yellow foam (1.3 g, 60%). $^1$H NMR (CDCl$_3$) δ 1.04 (s, 9H, CH$_3$), 2.08 (s, 3H, SCH$_3$), 2.19-2.35 (m, 2H, H-2), 3.67-3.71 (m, 2H, H-5'), 3.97-3.99 (m, 2H, H-4', H-3'), 4.23 (br s, 2H, CH$_2$N), 4.58 (s, 2H; CH$_2$S), 6.31 (dd, J=5.7, 7.9 Hz, H-1'), 7.19-7.62 (m, 11H, H8, H$_{Ar}$). Mass (+ve electrospray) calcd for C$_{34}$H$_{38}$F$_3$N$_5$O$_5$SSi 713. found: 714.

3'-O-Azidomethyl-7-deaza-7-[3-(2,2,2-trifluoroacetamido)-prop-1-ynyl]-2'-deoxyguanosine (22)

To a solution of (21) (1.3 mg, 1.8 mmol), cyclohexene (0.91 ml, 9 mmol) in CH$_2$Cl$_2$ (10 ml) in 4° C., sulfurylchloride (1M in CH$_2$Cl$_2$) (1.1 ml, 1.1 mmol) was added drop wise under N$_2$. After 30 min., TLC indicated the full consumption of the nucleoside (22). After evaporation to remove the solvent, the residue was then subjected to high vacuum for 20 min, and then treated with NaN$_3$ (585 mmol, 9 mmol) and DMF (10 ml). The resulted suspension was stirred under room temperature for 2 h. Extraction with CH$_2$Cl$_2$/NaCl (10%) gave a yellow gum, which was treated with TBAF in THF (1 M, 3 ml) and THF (3 ml) at room temperature for 20 min. Evaporation to remove solvents, extraction with EtOAc/sat. aq. NaHCO$_3$, followed by purification by chromatography on silica (EtOAc to EtOAc:MeOH 9:1) gave (22) as a yellow foam (420 mg, 50%). $^1$H NMR (d$_6$ DMSO): δ 2.36-2.42 (m, 1H, H-2'), 2.49-2.55 (m, 1H, H-2'), 3.57-3.59 (m, 2H, H-5'), 3.97-4.00 (m, 1H, H-4'), 4.29 (m, 2H, CH$_2$N), 4.46-4.48 (m, 1H, H-3'), 4.92-4.96 (m, 2H, CH$_2$N$_3$), 5.14 (t, J=5.4 Hz, 1H, 5'-OH), 5.96-6.00 (dd, J=5.7, 8.7 Hz, 1H, H-1'), 6.46 (br s, 2H, NH$_2$), 7.39 (s, 1H, H-6), 10.14 (s, 1H, NH), 10.63 (s, 1H, H-3).

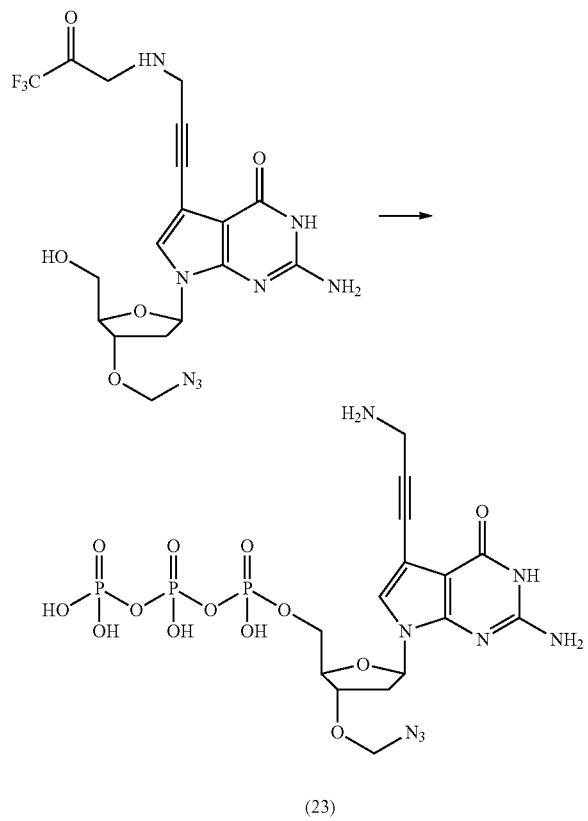

3'-O-Azidomethyl-7-deaza-7-[3-(2,2,2-trifluoroacetamido)-prop-1-ynyl]-2'-deoxyguanosine 5'-O-nucleoside triphosphate (23)

Tetrasodium diphosphate decahydrate (1.5 g, 3.4 mmol) was dissolved in water (34 ml) and the solution was applied to a column of dowex 50 in the H⁺ form. The column was washed with water. The eluent dropped directly into a cooled (ice bath) and stirred solution of tri-n-butyl amine (1.6 ml, 6.8 mmol) in EtOH (14 ml). The column was washed until the pH of the eluent increased to 6. The aqueous ethanol solution was evaporated to dryness and then co-evaporated twice with ethanol and twice with anhydrous DMF. The residue was dissolved in DMF (6.7 ml). The pale yellow solution was stored over 4 Å molecular sieves. The nucleoside (22) and proton sponge was dried over $P_2O_5$ under vacuum overnight. A solution of (22) (104 mg, 0.22 mmol) and proton sponge (71 mg, 0.33 mmol) in trimethylphosphate (0.4 ml) was stirred with 4 Å molecular sieves for 1 h. Freshly distilled $POCl_3$ (25 µl, 0.26 mmol) was added and the solution was stirred at 4° C. for 2 h. The mixture was slowly warmed up to room temperature and bis(tri-n-butyl ammonium) pyrophosphate (1.76 ml, 0.88 mmol) and anhydrous tri-n-butyl amine (0.42 ml, 1.76 mmol) were added. After 5 min, the reaction was quenched with 0.1 M TEAB (triethylammonium bicarbonate) buffer (15 ml) and stirred for 3 h. The water was removed under reduced pressure and the resulting residue dissolved in concentrated ammonia (ρ 0.88, 10 ml) and stirred at room temperature for 16 h. The reaction mixture was then evaporated to dryness. The residue was dissolved in water and the solution applied to a DEAE-Sephadex A-25 column. MPLC was performed with a linear gradient of 2 L each of 0.05 M and 1 M TEAB. The triphosphate was eluted between 0.7 M and 0.8 M buffer. Fractions containing the product were combined and evaporated to dryness. The residue was dissolved in water and further purified by HPLC. $t_r$(23)=20.5 min (Zorbax C18 preparative column, gradient: 5% to 35% B in 30 min, buffer A 0.1M TEAB, buffer B MeCN). The product was isolated as a white foam (225 O.D., 29.6 µmol, 13.4%, $\epsilon_{260}$=7,600). ¹HNMR ($D_2O$) δ 2.43-2.5 (m, 2H, H-2'), 3.85 (m, 2H, $CH_2N$), 3.97-4.07 (m, 2H, H-5'), 4.25 (br s, 1H, H-4'), 4.57 (br s, 1H, H-3'), 4.74-4.78 (m, 2H, $CH_2N_3$), 6.26-6.29 (m, 1H, H-1'), 7.41 (s, 1H, H-8). ³¹P-NMR ($D_2O$) δ −8.6 (m, 1P, $P_\gamma$), −10.1 (d, J=19.4 Hz, 1P, $P_\alpha$), −21.8 (t, J=19.4 Hz, 1P, $P_\beta$). Mass (−ve electrospray) calcd for $C_{15}H_{21}N_8O_{13}P_3$ 614. found 613.

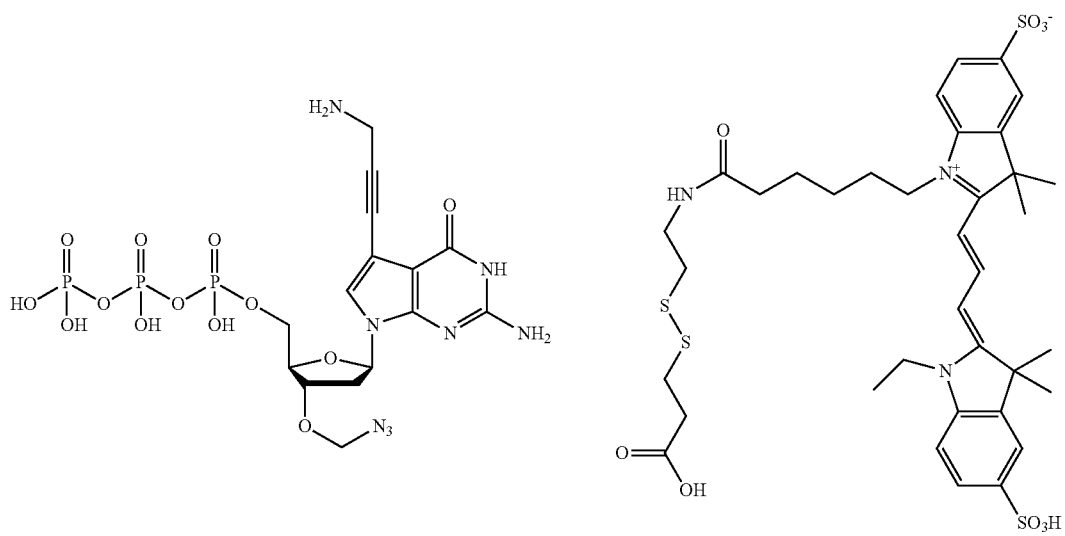

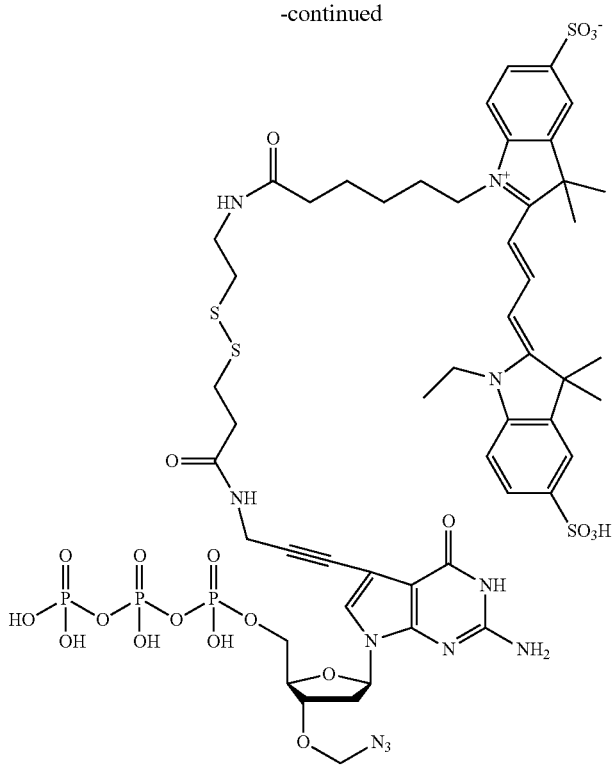

(24)

A mixture of disulphide linkered-Cy3 (2.5 µmol), 1-(3-dimethylaminopropyl)-3-ethylcarbodiimide hydrochloride (EDC) (0.95 mg, 5 µmol), 1-hydroxybenzotriazole (HOBt) (0.68 mg, 5 µmol) and N-methyl-morpholine (0.55 µL, 5 µmol) in DMF (0.9 ml) was stirred at room temperature for 1 h. A solution of (23) (44 O.D., 3.75 µmol) in 0.1 ml water was added to the reaction mixture at 4° C., and left at room temperature for 3 h. The reaction was quenched with TEAB buffer (0.1M, 10 ml) and loaded on a DEAE Sephadex column (2×5 cm). The column was first eluted with 0.1 M TEAB buffer (100 ml) and then 1 M TEAB buffer (100 ml). The desired triphosphate product was eluted out with 1 M TEAB buffer. Concentrating the fraction containing the product and applied to HPLC. $t_r$(24)=23.8 min (Zorbax C18 preparative column, gradient: 5% to 55% B in 30 min, buffer A 0.1M TEAB, buffer B MeCN). The product was isolated as a red foam (0.5 µmol, 20%, $\epsilon_{max}$=150,000). $^1$H NMR (D$_2$O) δ 1.17-1.71 (m, 20H, 4×CH$_2$, 4×CH$_3$), 2.07-2.15 (m, 1H, H-2'), 2.21-2.30 (m, 1H, H-2'), 2.52-2.58 (m, 2H, CH$_2$), 2.66-2.68 (m, 2H, CH$_2$), 2.72-2.76 (m, 2H, CH$_2$), 3.08-3.19 (m, 2H, CH$_2$), 3.81-3.93 (m, 6H, CH$_2$, H-5'), 4.08-4.16 (m, 1H, H-4'), 4.45-4.47 (m, 1H, H-3'), 4.70-4.79 (m, 2H, CH$_2$N$_3$), 6.05-6.08 (m, 2H, H$_{Ar}$), 6.15-6.18 (m, 1H, H-1'), 7.11 (s, 1H, H-8), 7.09-7.18 (m, 2H, CH), 7.63-7.72 (m, 4H, H$_{Ar}$), 8.27-8.29 (m, 1H, CH). $^{31}$P NMR (D$_2$O) δ −4.7 (m, 1P, P$_\gamma$), −9.8 (m, 1P, P$_\alpha$), −19.7 (m, 1P, P$_\beta$). Mass (−ve electrospray) calcd for C$_{51}$H$_{66}$N$_{11}$O$_{21}$P$_3$S$_4$ 1389.25. found 1388 (M−H), 694 [M−2H], 462 [M−3H].

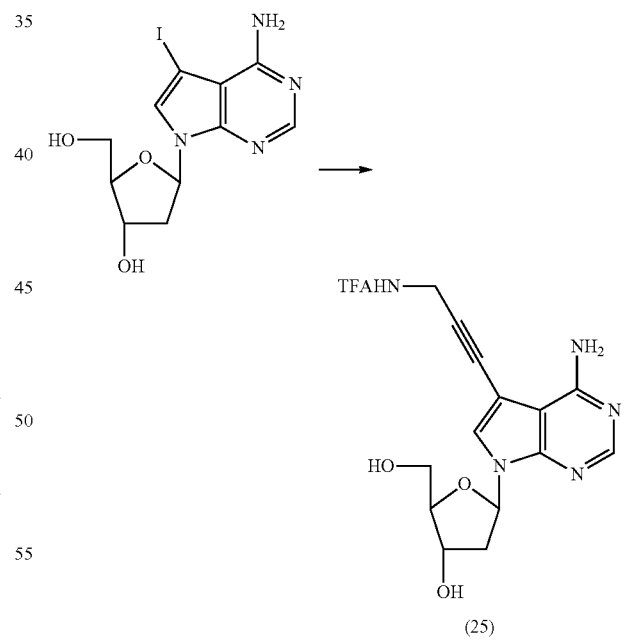

7-Deaza-7-[3-(2,2,2-trifluoroacetamido)-prop-1-ynyl]-2'-deoxyadenosine (25)

To a suspension of 7-deaza-7-iodo-2'-deoxyadenosine (1 g, 2.65 mmol) and CuI (100 mg, 0.53 mmol) in dry DMF (20 ml) was added triethylamine (740 µl, 5.3 mmol). After stirring for 5 min trifluoro-N-prop-2-ynyl-acetamide (1.2 g, 7.95 mmol) and Pd(PPh₃)₄ (308 mg, 0.26 mmol) were added to the mixture and the reaction was stirred at room temperature in the dark for 16 h. MeOH (40 ml) and bicarbonate dowex was added to the reaction mixture and stirred for 45 min. The mixture was filtered. The filtrate washed with MeOH and the solvent was removed under vacuum. The crude mixture was purified by chromatography on silica (EtOAc to EtOAc: MeOH 95:20) to give slightly yellow powder (25) (1.0 g, 95%). $^1$H NMR (d$_6$ DMSO) δ 2.11-2.19 (m, 1H, H-2'), 2.40-2.46 (m, 1H, H-2'), 3.44-3.58 (m, 2H, H-5'), 3.80 (m, 1H, H-4'), 4.29 (m, 3H, H-3', CH$_2$N), 5.07 (t, J=5.5 Hz, 1H, OH), 5.26 (d, J=4.0 Hz, 1H, OH), 6.45 (dd, J=6.1, 8.1 Hz, 1H, H-1'), 7.74 (s, 1H, H-8), 8.09 (s, 1H, H-2), 10.09 (t, J=5.3 Hz, 1H, NH).

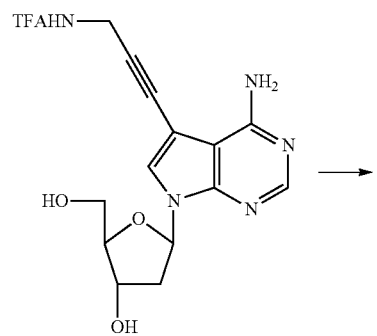

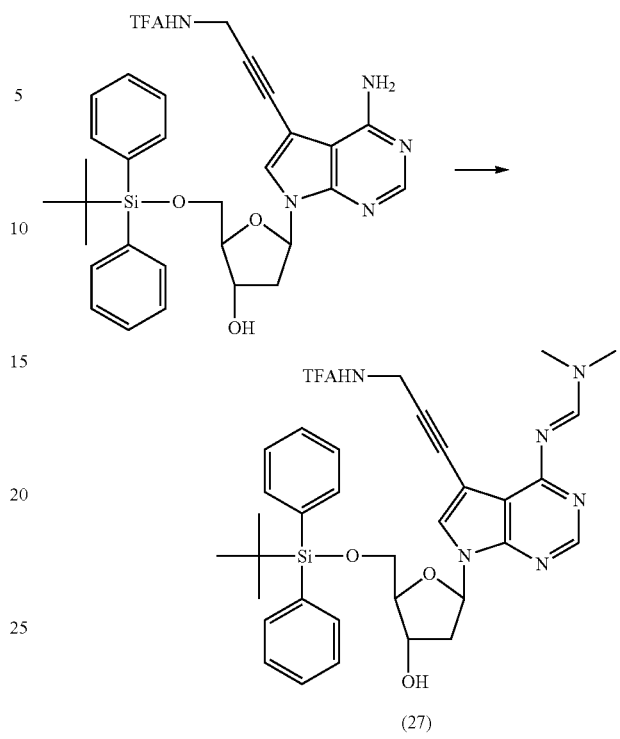

(26)

5'-O-(tert-Butyldiphenylsilyl)-7-deaza-7-[3-(2,2,2-trifluoroacetamido)-prop-1-ynyl]-2'-deoxyadenosine (26)

The nucleoside (25) (1.13 g, 2.82 mmol) was coevaporated twice in dry pyridine (2×10 ml) and dissolved in dry pyridine (18 ml). To this solution was added t-butyldiphenylsilylchloride (748 μl, 2.87 mmol) in small portions at 0° C. The reaction mixture was let to warm up at room temperature and left stirring overnight. The reaction was quenched with sat. aq. NaCl solution. EtOAc (25 ml) was added to reaction mixture and the aqueous layer was extracted with EtOAc three times. After drying the combined organic extracts (MgSO$_4$) the solvent was removed under vacuum. Purification by chromatography on silica (DCM then EtOAc to EtOAc:MeOH 85:15) gave (26) as a slightly yellow powder (1.76 g, 97%). $^1$H NMR (d$_6$ DMSO) δ 1.03 (s, 9H, tBu), 2.25-2.32 (m, 1H, H-2'), 2.06-2.47 (m, 1H, H-2'), 3.71-3.90 (m, 2H, H-5'), 3.90-3.96 (m, 1H, H-4'), 4.32 (m, 2H, CH$_2$N), 4.46 (m, 1H, H-3'), 5.42 (br s, 1H, OH), 6.53 (t, J=6.7 Hz, 1H, H-1'), 7.38-7.64 (m, 11H, H-8 and H$_{Ar}$), 8.16 (s, 1H, H-2), 10.12 (t, J=5.3 Hz, 1H, NH).

5'-O-(tert-Butyldiphenylsilyl)-7-deaza-4-N,N'-dimethylformadin-7-[3-(2,2,2-trifluoroacetamido)-prop-1-ynyl]-2'-deoxyadenosine (27)

A solution of the nucleoside (26) (831 mg, 1.30 mmol) was dissolved in a mixture of MeOH:N,N-dimethylacetal (30 ml: 3 ml) and stirred at 40° C. The reaction monitored by TLC, was complete after 1 h. The solvent was removed under vacuum. Purification by chromatography on silica (EtOAc: MeOH 95:5) gave (27) as a slightly brown powder (777 mg, 86%). $^1$H NMR (d$_6$ DMSO) δ 0.99 (s, 9H, tBu), 2.22-2.29 (m, 1H, H-2'), 2.50-2.59 (m, 1H, H-2'), 3.13 (s. 3H, CH$_3$), 3.18 (s. 3H, CH$_3$), 3.68-3.87 (m, 2H, H-5'), 3.88-3.92 (m, 1H, H-4'), 4.25 (m, 2H, CH$_2$N), 4.43 (m, 1H, H-3'), 6.56 (t, J=6.6 Hz, 1H, H-1'), 7.36-7.65 (m, 10H, H$_{Ar}$), 7.71 (s, 1H, H-8), 8.33 (s, 1H, CH), 8.8 (s, 1H, H-2), 10.12 (t, J=5.3 Hz, 1H, NH).

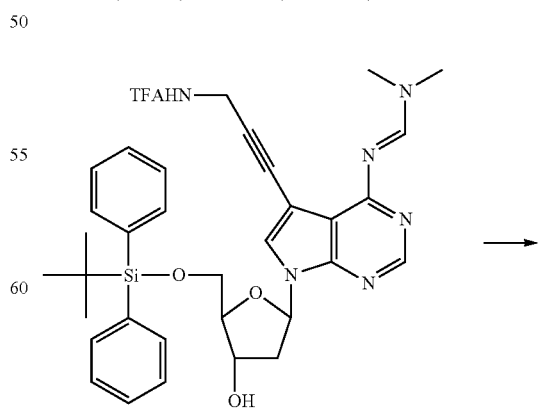

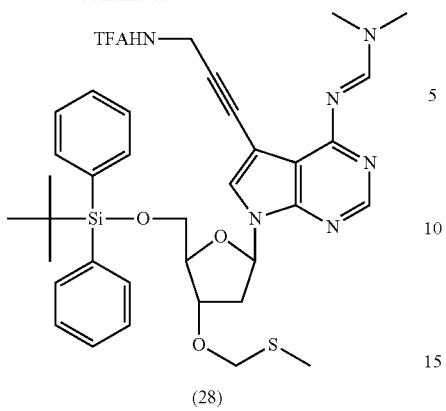

(28)

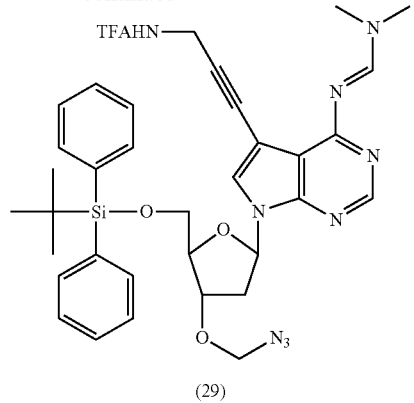

(29)

5'-O-(tert-Butyldiphenylsilyl)-7-deaza-4-N,N'-dimethylformadin-3'-O-methylthiomethoxy-7-[3-(2,2,2-trifluoroacetamido)-prop-1-ynyl]-2'-deoxyadenosine (28)

To a solution of (27) (623 mg, 0.89 mmol) in dry DMSO (8 ml) was added acetic acid (775 µl, 13.35 mmol) and acetic anhydride (2.54 ml, 26.7 mmol). The mixture was stirred overnight at room temperature. The reaction was then poured into EtOAc and sat. aq. NaHCO$_3$ (1:1) solution and stirred vigorously. The organic layer was washed one more time with sat. aq. NaHCO$_3$ and dried over MgSO$_4$. After removing the solvent under reduced pressure, the product (28) was purified by chromatography on silica (EtOAc:petroleum ether 1:2, then EtOAc) yielding (28) (350 mg, 52%). $^1$H NMR (d$_6$ DMSO): δ, 1.0 (s, 9H, tBu), 2.09 (s, 3H, SCH$_3$), 2.41-2.48 (m, 1H, H-2'), 2.64-2.72 (m, 1H, H-2'), 3.12 (s, 3H, CH$_3$), 3.17 (s, 3H, CH$_3$), 3.66-3.89 (m, 2H, H-5'), 4.04 (m, 1H, H-4'), 4.26 (m, J=5.6 Hz, 2H, CH$_2$), 4.67 (m, 1H, H-3'), 4.74 (br s, 2H, CH$_2$), 6.49 (t, J=6.1, 8.1 Hz, 1H, H-1'), 7.37-7.48 (m, 5H, H$_{Ar}$), 7.58-7.67 (m, 5H, H$_{Ar}$), 7.76 (s, 1H, H-8), 8.30 (s, 1H, CH), 8.79 (s, 1H, H-2), 10.05 (t, J=5.6 Hz, 1H, NH).

3'-O-Azidomethyl-5'-O-(tert-butyldiphenylsilyl)-7-deaza-4-N,N-dimethylformadin-7-[3-(2,2,2-trifluoroacetamido)-prop-1-ynyl]-2'-deoxyadenosine (29)

To a solution of (28) (200 mg, 0.26 mmol) and cyclohexene (0.135 ml, 1.3 mmol) in dry CH$_2$Cl$_2$ (5 ml) at 0° C., sulfurylchloride (32 µl, 0.39 mmol) was added under N$_2$. After 10 min, TLC indicated the full consumption of the nucleoside (28). The solvent was evaporated and the residue was subjected to high vacuum for 20 min. It was then redissolved in dry DMF (3 ml), cooled to 0° C. and treated with NaN$_3$ (86 mg, 1.3 mmol). The resulting suspension was stirred under room temperature for 3 h. The reaction was partitioned between EtOAc and water. The aqueous phases were extracted with EtOAc. The combined organic extracts were combined and dried over MgSO$_4$. After removing the solvent under reduced pressure, the mixture was purified by chromatography on silica (EtOAc) yielding an oil (29) (155 mg, 80%). $^1$H NMR (d$_6$ DMSO): δ 0.99 (s, 9H, tBu), 2.45-2.50 (m, 1H, H-2'), 2.69-2.78 (m, 1H, H-2'), 3.12 (s, 3H, CH$_2$), 3.17 (s, 3H, CH$_2$), 3.67-3.88 (m, 2H, H-5'), 4.06 (m, 1H, H-4'), 4.25 (m, 2H, CH$_2$), 4.61 (m, 1H, H-3'), 4.84-4.97 (m, 2H, CH$_2$), 6.58 (t, J=6.6 Hz, 1H, H-1'), 7.35-7.47 (m, 5H, H$_{Ar}$), 7.58-7.65 (m, 5H, H$_{Ar}$), 7.77 (s, 1H, H-8), 8.30 (s, 1H, CH), 8.79 (s, 1H, H-2), 10.05 (br s, 1H, NH).

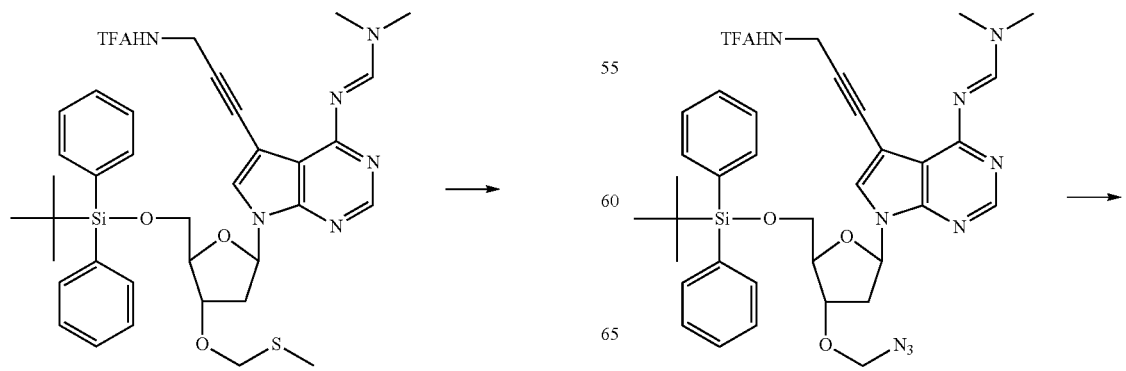

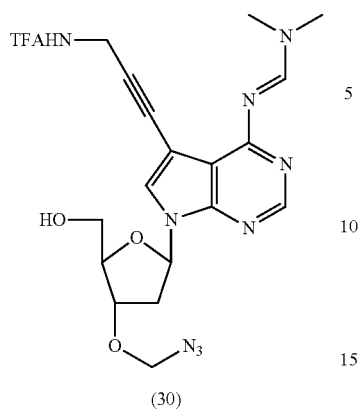

(30)

3'-O-Azidomethyl-7-deaza-4-N,N-dimethylformadin-7-[3-(2,2,2-trifluoroacetamido)-prop-1-ynyl]-2'-deoxyadenosine (30)

A solution of (29) (155 mg, 0.207 mmol) in solution in tetrahydrofuran (THF) (3 ml) was treated with TBAF (1 M in THF, 228 μl) at 0° C. The ice-bath was then removed and the reaction mixture stirred at room temperature. After 2 h-TLC indicated the full consumption of the nucleoside. The solvent was removed. Purification by chromatography on silica (EtOAc:MeOH 95:5) gave (30) (86 mg, 82%) as a pale brown oil. $^1$H NMR (d$_6$ DMSO) δ 2.40-2.48 (dd, J=8.1, 13.6 Hz, 1H, H-2'), 2.59-2.68 (dd, J=8.3, 14 Hz, 1H, H-2'), 3.12 (s, 3H, CH$_3$), 3.17 (s, 3H, CH$_3$), 3.52-3.62 (m, 2H, H-5'), 4.02 (m, 1H, H-4'), 4.28 (d, J=5.6 Hz, 2H, CH$_2$NH), 4.47 (m, 1H, H-3'), 4.89 (s, 2H, CH$_2$N$_3$), 5.19 (t, J=5.6 Hz, 1H, OH), 6.49 (dd, J=8.1, 8.7 Hz, 1H, H-1'), 7.88 (s, 1H, H-8), 8.34 (s, 1H, CH), 8.80 (s, 1H, H-2), 10.08 (s, 1H, NH).

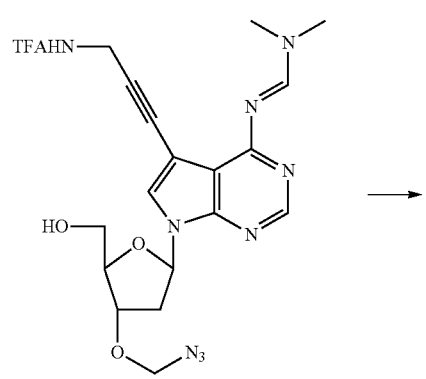

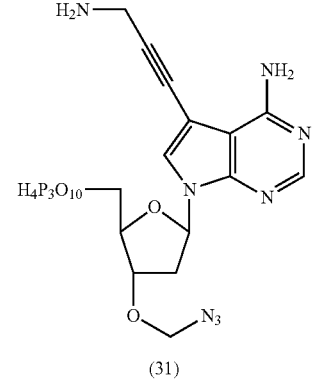

(31)

7-(3-Aminoprop-1-ynyl)-3'-O-azidomethyl-7-deaza-2'-deoxyadenosine 5'-O-nucleoside triphosphate (31)

The nucleoside (30) and proton sponge was dried over P$_2$O$_5$ under vacuum overnight. A solution of (30) (150 mg, 0.294 mmol) and proton sponge (126 mg, 0.588 mmol) in trimethylphosphate (980 μl) was stirred with 4 Å molecular sieves for 1 h. Freshly distilled POCl$_3$ (36 μl, 0.388 mmol) was added and the solution was stirred at 4° C. for 2 h. The mixture was slowly warmed up to room temperature and bis(tri-n-butyl ammonium) pyrophosphate 0.5 M solution in DMF (2.35 ml, 1.17 mmol) and anhydrous tri-n-butyl amine (560 μl, 2.35 mmol) was added. After 5 min, the reaction was quenched with 0.1 M TEAB (triethylammonium bicarbonate) buffer (15 ml) and stirred for 3 h. The water was removed under reduced pressure and the resulting residue dissolved in concentrated ammonia (ρ 0.88, 15 ml) and stirred at room temperature for 16 h. The reaction mixture was then evaporated to dryness. The residue was dissolved in water and the solution applied to a DEAE-Sephadex A-25 column. MPLC was performed with a linear gradient of 0.05 M to 1 M TEAB. Fractions containing the product were combined and evaporated to dryness. The residue was dissolved in water and further purified by HPLC. HPLC: t$_r$(31): 19.94 min (Zorbax C18 preparative column, gradient: 5% to 35% B in 20 min, buffer A 0.1M TEAB, buffer B MeCN). The product (31) was isolated as a white foam (17.5 μmol, 5.9%, ε$_{280}$=15000). $^1$H NMR (D$_2$O) δ 2.67-2.84 (2m, 2H, H-2'), 4.14 (m, 2H, CH$_2$NH), 4.17-4.36 (m, 2H, H-5'), 4.52 (br s, H-4'), 6.73 (t, J=6.6 Hz, H-1'), 8.06 (s, 1H, H-8), 8.19 (s, 1H, H-2). $^{31}$P NMR (D$_2$O) δ −5.07 (d, J=21.8 Hz, 1P, P$_γ$), −10.19 (d, J=19.8 Hz, 1P, P$_α$), −21.32 (t, J=19.8 Hz, 1P, P$_β$). Mass (−ve electrospray) calcd for C$_{15}$H$_{21}$N$_8$O$_{12}$P$_3$ 598.05. found 596.

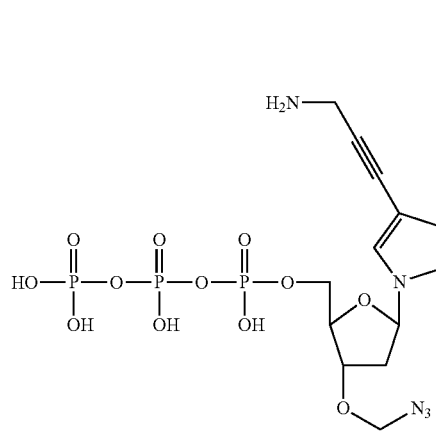
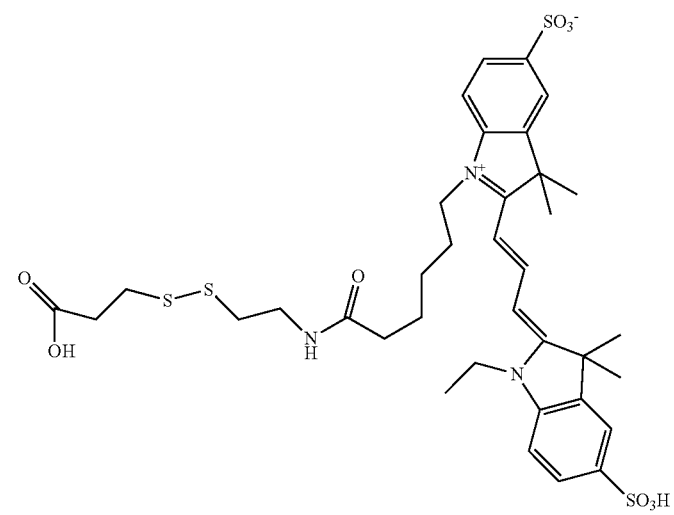

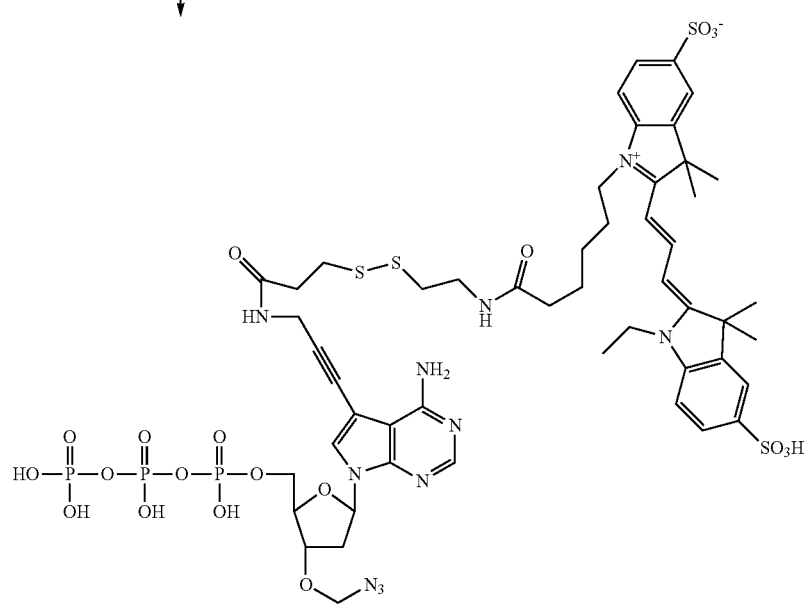

(32)

To the Cy3 disulphide linker (1.3 µmol) in solution in DMF (450 µl) is added at 0° C. 50 µl of a mixture of 1-(3-dimethylaminopropyl)-3-ethylcarbodiimide hydrochloride, 1-hydroxybenzotriazole hydrate and N-methylmorpholine (26 µM each) in DMF. The reaction mixture was stirred at room temperature for 1 h. The reaction was monitored by TLC (MeOH:CH$_2$Cl$_2$ 3:7) until all the dye linker was consumed. Then DMF (400 µl) was added at 0° C., followed by the nucleotide (31) (1.2 µmol) in solution in water (100 µl) and the reaction mixture and stirred at room temperature overnight. TLC (MeOH:CH$_2$Cl$_2$ 4:6) showed complete consumption of the activated ester and a dark red spot appeared on the baseline. The reaction was quenched with TEAB buffer (0.1M, 10 ml) and loaded on a DEAE Sephadex column (2×5 cm). The column was first eluted with 0.1 M TEAB buffer (100 ml) to wash off organic residues and then 1 M TEAB buffer (100 ml). The desired triphosphate (32) was eluted out with 1 M TEAB buffer. The fraction containing the product were combined, evaporated and purified by HPLC. HPLC conditions: t$_r$(32): 22.44 min (Zorbax C18 preparative column, gradient: 5% to 35% B in 20 min, buffer A 0.1M TEAB, buffer B MeCN). The product was isolated as dark pink solid (0.15 µmol, 12.5%, $\epsilon_{550}$=150000). $^1$H NMR (D$_2$O) δ 2.03 (t, 2H, CH$_2$), 2.25 (m, 1H, H-2'), 2.43 (m, 1H, H-2'), 2.50 (m, 2H, CH$_2$), 2.66 (m, 2H, CH$_2$), 3.79 (m, 2H CH$_2$), 3.99 (m, 4H, CH$_2$N, H-5'), 4.18 (br s, 1H, H-4'), 6.02, 6.17 (2d, J=13.64 Hz, 2H, H$_{Ar}$), 6.30 (dd, J=6.06, 8.58 Hz, H-1'), 7.08, 7.22 (2d, 2H, 2×=CH), 7.58-7.82 (m, 5H, H$_{Ar}$, H-2, H-8), 8.29 (m, =CH). $^{31}$P NMR (D$_2$O) δ −4.83 (m, 1P, P$_\gamma$), −10.06 (m, 1P, P$_\alpha$), −20.72 (m, 1P, P$_\beta$).

Enzyme Incorporation of 3'-Azidomethyl dNTPs

To a 100 nM DNA primer/template (primer previously labelled with P32 and T4 polynucleotide kinase) in Tris-HCl pH 8.8 50 mM, Tween-20 0.01%, and MgSO₄ 4 mM, add 2 μM compound 6 and 100 nM polymerase (*Thermococcus* sp. 9°N exo⁻Y409V A485L supplied by New England Biolabs). The template consists of a run of 10 adenine bases to show the effect of the block. The reaction is heated to 65 C for 10 mins. To show complete blocking, a chase is performed with the four native, unblocked nucleoside triphosphates. Quantitative incorporation of a single azidomethyl blocked dTTP can be observed and thus the azidomethyl group can be seen to act as an effective block to further incorporation.

Figure 5:
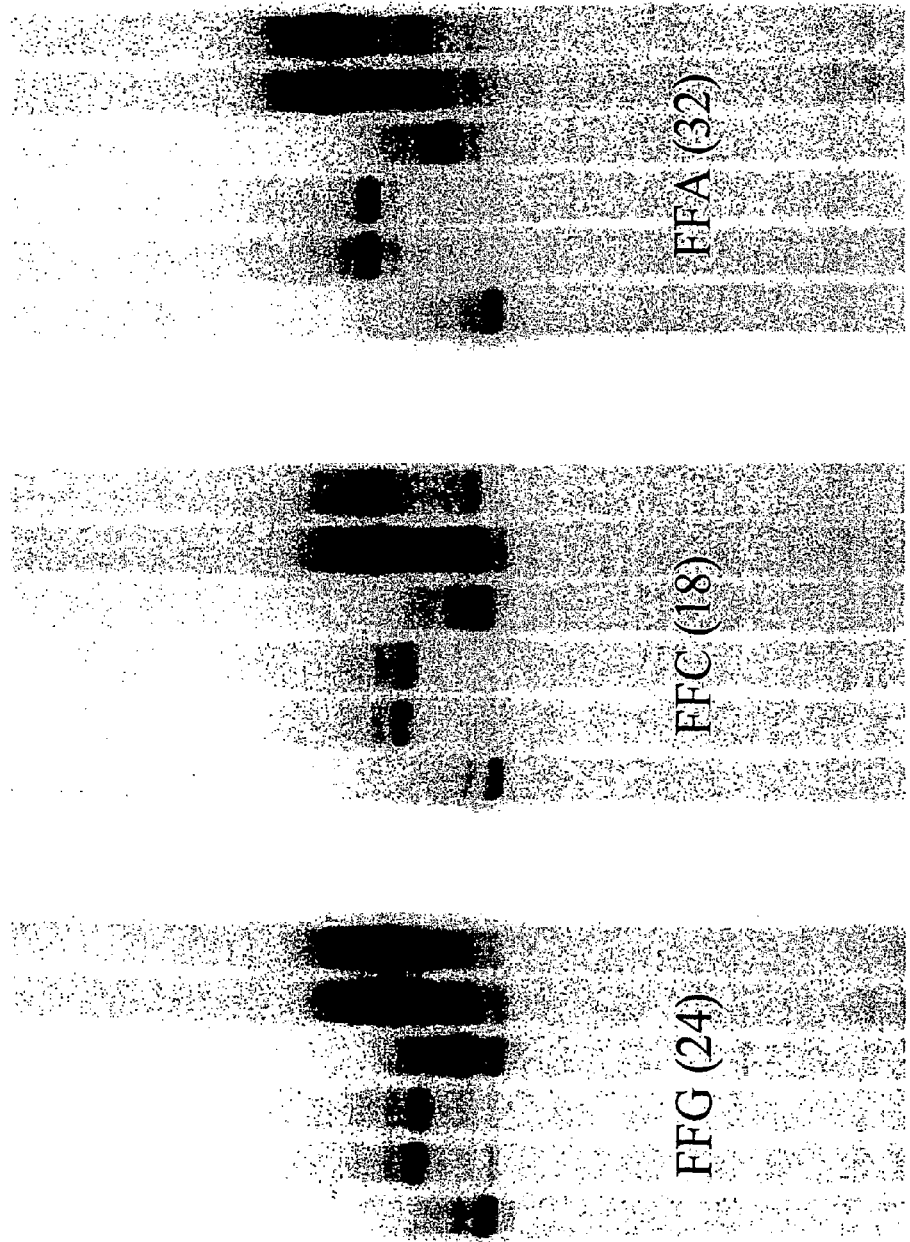
FIG. 5 shows two cycles of incorporation of labelled and blocked DGTP, DCTP and dATP respectively (compounds 18, 24 and 32).
Figure 6:
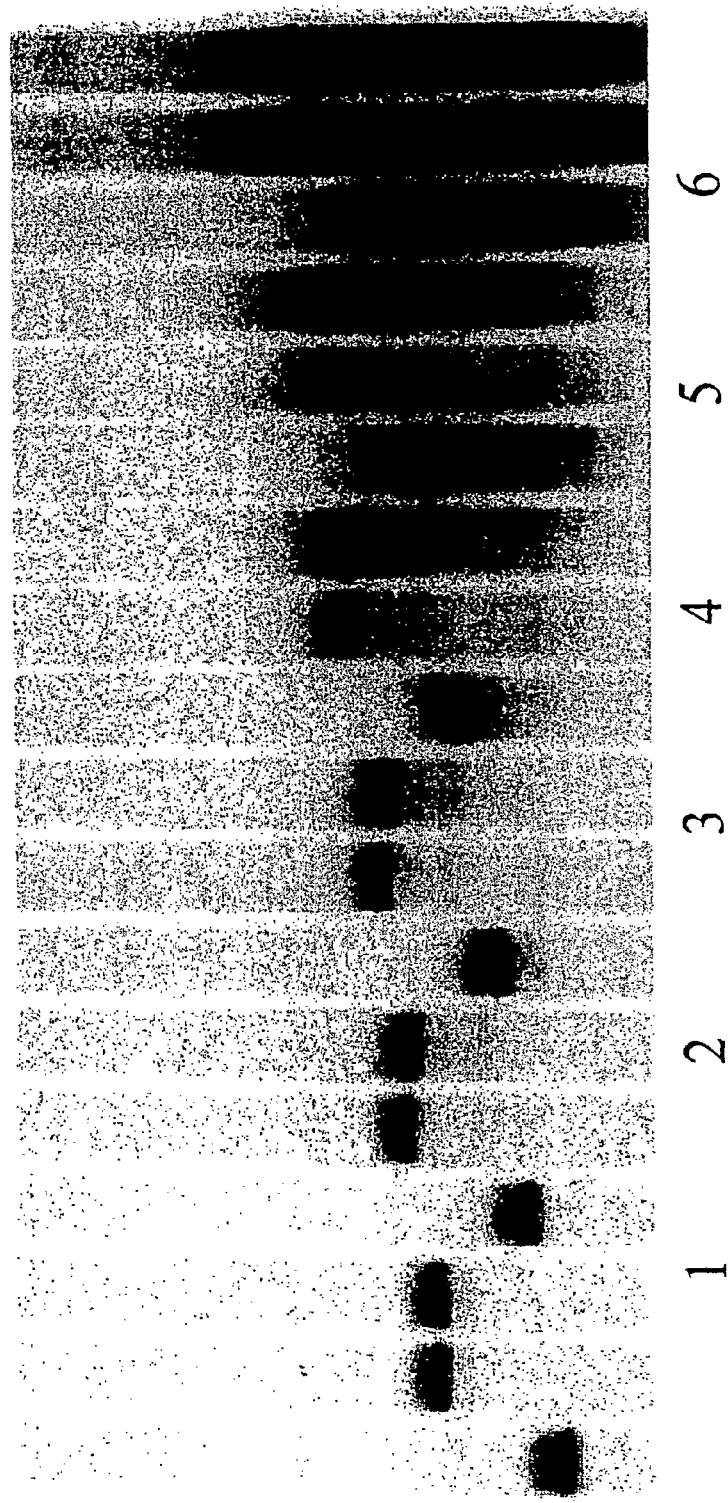
FIG. 6 shows six cycles of incorporation of labelled and blocked DTTP (compound 6).

By attaching a hairpin DNA (covalently attached self complementary primer/template) to a streptavidin bead The reaction can be performed over multiple cycles as shown in FIGS. 5 and 6.

Preparation of the Streptavidin Beads

Remove the storage buffer and wash the beads 3 times with TE buffer (Tris-HCl pH 8, 10 mM and EDTA, 1 mM). Resuspend in B & W buffer (10 mM Tris-HCl pH 7.5, 1 mM EDTA and 2.0 M NaCl), add biotinylated ³²P labelled hairpin DNA with appropriate overhanging template sequence. Allow to stand at room temperature for 15 minutes. Remove buffer and wash beads 3 times TE buffer.

Incorporation of the Fully Functional Nucleoside Triphosphate (FFN)

To a solution of Tris-HCl pH 8.8 50 mM, Tween-20 0.01%, MgSO₄ 4 mM, MnCl₂ 0.4 mM (except cycle 1, 0.2 mM), add 2 μM FFN and 100 nM polymerase. This solution is then added to the beads and mixed thoroughly and incubated at 65° C. for 10-15 minutes. The reaction mixture is removed and the beads washed 3 times with TE buffer.

Deblocking Step

Tris-(2-carboxyethyl)phosphines trisodium salt (TCEP) (0.1M) is added to the beads and mixed thoroughly. The mixture was then incubated at 65° C. for 15 minutes. The deblocking solution is removed and the beads washed 3 times with TE buffer.

Capping Step

Iodoacetamide (431 mM) in 0.1 mM phosphate pH 6.5 is added to the beads and mixed thoroughly, this is then left at room temperature for 5 minutes. The capping solution is removed and the beads washed 3 times with TE buffer.

Repeat as Required

The reaction products can be analysed by placing the bead solution in the well of a standard 12% polyacrylamide DNA sequencing gel in 40% formamide loading buffer. Running the gel under denaturing conditions causes the DNA to be released from the beads and onto the gel. The DNA band shifts are affected by both the presence of dye and the addition of extra nucleotides and thus the cleavage of the dye (and block) with the phosphine cause a mobility shift on the gel.

Two cycles of incorporation with compounds 18 (C), 24 (G) and 32 (A) and six cycles with compound 6 can be seen in figures FIG. 5 and FIG. 6.

3'-OH Protected with an Allyl Group:

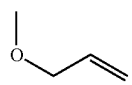

Nucleotides bearing this blocking group at the 3'position have been synthesised, shown to be successfully incorporated by DNA polymerases, block efficiently and may be subsequently removed under neutral, aqueous conditions using water soluble phosphines or thiols allowing further extension.

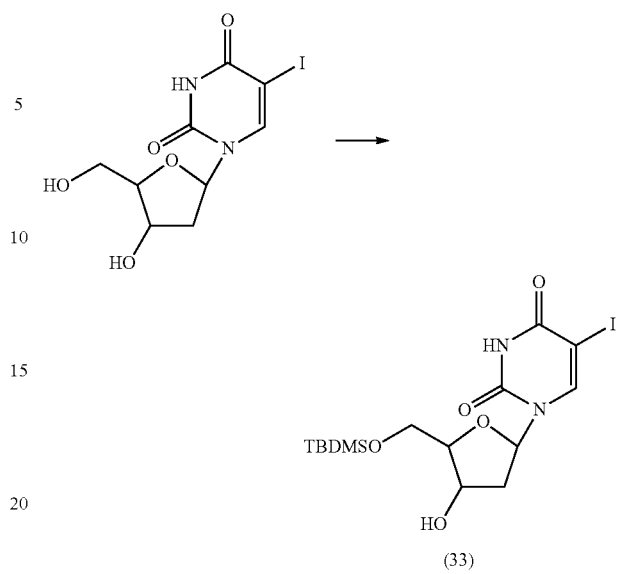

5'-O-(t-Butyldimethylsilyl)-5-iodo-2'-deoxyuridine (33)

To a solution of 5-iodo-2'-deoxyuridine (5.0 g, 14 mmol) in 70 ml in dry N,N-dimethylformamide (DMF) was added imidazole (1.09 g, 16 mmol), followed by (2.41 g, 16 mmol) TBDMSCl at 0° C. The mixture was left in the ice bath and stirred overnight. The reaction was quenched with sat. aq. NaCl solution and extracted with EtOAc. After drying (MgSO₄), the solvent was removed and the crude mixture was purified by chromatography on silica (EtOAc:petroleum ether 3:7). The product (33) (5.9 g, 90%) was obtained as a colourless solid. ¹H NMR (d₆ DMSO) δ 0.00 (s, 3H, CH₃), 0.79 (s, 9H, tBu), 1.88-1.97 (m, 1H, H-2'), 2.00-2.05 (m, 1H, H-2'), 3.59-3.71 (m, 2H, H-5'), 3.75 (br s, 1H, H-4'), 4.06 (br s, 1H, H-3'), 5.18 (d, J=4.0 Hz, 1H, OH), 5.98 (t, J=5.9 Hz, 1H, H-1'), 7.89 (s, 1H, H-6), 11.62 (s, 1H, NH). Mass (−ve electrospray) calcd for C₁₅H₂₅IN₂O₆Si 468.06. found 467.

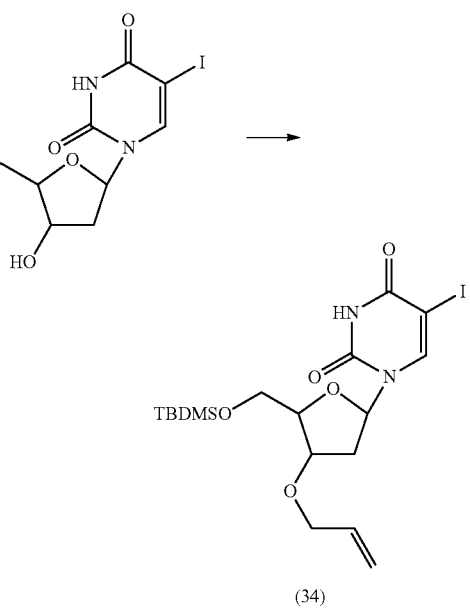

3'-O-Allyl-5'-O-t-butyldimethylsilyl-5-iodo-2'-deoxyuridine (34)

To a suspension of NaH (497 mg, 12.4 mmol, 60% in mineral oil) in dry THF (20 ml) a solution of 5'-TBDMS protected 5-iodo-2'-deoxyuridine (2.8 g, 5.9 mmol) in dry THF (50 ml) was added drop wise. After the gas evolution had stopped the mixture was stirred for another 10 min and then allylbromide (561 µl, 6.5 mmol) was added drop wise. After the complete addition the milky reaction mixture was stirred at room temperature for 16 h. The reaction was quenched by addition of sat. aq. NaCl solution (30 ml). The aqueous layer was extracted three times using EtOAc and after washing with sat. aq. NaCl solution the organic phase was dried (MgSO$_4$). After removing of the solvents the crude product was purified by chromatography (EtOAc:petroleum ether 1:1). The allylated product (2.39 g, 80%) was obtained as a colourless foam. $^1$H NMR (d$_6$ DMSO) δ −0.01 (s, 3H, CH$_3$), 0.78 (s, 9H, tBu), 1.94-2.01 (m, 1H, H-2'), 2.16-2.21 (m, 1H, H-2'), 3.61-3.71 (m, 2H, H-5'), 3.87-3.94 (m, 4H, H-3', H-4', OCH$_2$), 5.04 (dd, J=1.6, 10.4 Hz, 1H, =CH$_2$), 5.15 (dd, J=1.8, 17.3 Hz, 1H, =CH$_2$), 5.72-5.81 (m, 1H, CH=), 5.92 (t, J=5.7 Hz, 1H, H-1'), 7.88 (s, 1H, 6-H), 11.6 (s, 1H, NH). Mass (−ve electrospray) calcd for C$_{18}$H$_{29}$IN$_2$O$_5$Si 508.09. found 507.

3'-O-Allyl-5-iodo-2'-deoxyuridine (35)

To a solution of (34) (2.34 g, 4.71 mmol) in dry THF (40 ml) was added at 0° C. TBAF (5.2 ml, 5.2 mmol, 1 M solution in THF). The reaction mixture was allowed to warm up to room temperature and was then stirred for 16 h. The reaction was quenched by adding sat. NaCl solution (20 ml) and extracted with EtOAc three times. The combined organic layers were dried over MgSO$_4$. The crude mixture was purified by chromatography on silica (EtOAc:petrol 7:3). Product (35) (1.4 g, 75%) was isolated as a colourless solid. $^1$H NMR (d$_6$ DMSO) δ 2.02-2.39 (m, 2H, H-2'), 3.42-3.52 (m, 2H, H-5'), 3.84-3.88 (m, 3H, H-4', CH$_2$], 3.97-4.00 (m, 1H, H-3'), 5.02-5.09 (m, 2H, OH, =CH$_2$), (dd, J=1.9, 17.3 Hz, 1H, =CH$_2$), 5.73-5.82 (m, 1H, CH=), 5.94 (t, J=6.8 Hz, 1H, H-1'), 8.24 (s, 1H, H-6), 11.56 (s, 1H, NH). Mass (−ve electrospray) calcd for C$_{12}$H$_{16}$IN$_2$O$_5$ 394.0. found 393.

3'-O-Allyl-5-[3-(2,2,2-trifluoroacetamido)-prop-1-ynyl]-2'-deoxyuridine

To a solution of (35) (400 mg, 1.0 mmol) in dry DMF (10 ml) was added CuI (38 mg, 20 µmol) and triethylamine (300 µl, 2.0 mmol). The propargyltrifluoroacetamide (453 mg, 3.0 mmol) was added drop wise, followed by Pd(PPh$_3$)$_4$ (110 mg, 9.5 µmol). The reaction was stirred for 16 h in the dark. The reaction was quenched by adding MeOH (10 ml), DCM (10 ml) and bicarbonate dowex. The mixture was stirred for 30 min and then filtered. The solvents were removed under vacuum and the crude product was purified by chromatography on silica (EtOAc:petrol 3:7 to 7:3). The product was isolated as slightly yellow crystals (398 mg, 95%). $^1$H NMR (d$_6$ DMSO) δ 2.25-2.43 (m, 2H, H-2'), 3.65-3.76 (m, 2H, H-5'), 4.07-4.17 (m, 3H, H-4', CH$_2$), 4.21-4.23 (m, 1H, H-3'), 4.34 (d, J=5.5 Hz, 2H, CH$_2$N), 5.25-5.27 (m, 2H, =CH$_2$, OH), 5.38 (dd, J=1.83, 17.3 Hz, 1H, =CH$_2$), 5.96-6.06 (m, 1H, =CH), 6.17 (t, J=6.9 Hz, 1H, H-1'), 8.29 (s, 1H, H-6), 10.17 (t, J=5.5 Hz, 1H, NHTFA), 11.78 (s, 1H, NH). Mass (−ve electrospray) calcd for C$_{17}$H$_{18}$F$_3$N$_3$O$_6$ 417.11. found 416.

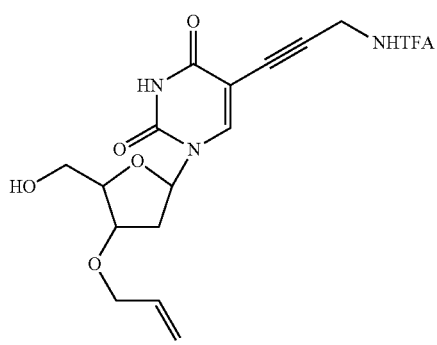

3'-O-Allyl-5-[3-(2,2,2-trifluoroacetamido)-prop-1-ynyl]-2'-deoxyuridine 5'-O-nucleoside triphosphate (37)

Under nitrogen (36) (100 mg, 0.24 mmol) and proton sponge (61.5 mg, 0.28 mmol), both dried under vacuum over $P_2O_5$ for 24 h, were dissolved in OP(OMe)$_3$ (225 µl). At 0° C. freshly distilled POCl$_3$ was added drop wise and the mixture was stirred for 1.5 h. Then pyrophosphate (1.44 ml, 0.72 gmol, 0.5 M in DMF) and nBu$_3$N (0.36 ml, 1.5 mmol) were added and the resulting mixture stirred for another 1.5 h. Triethylammonium bicarbonate solution (4.5 ml, 0.1 M solution, TEAB) was added and the reaction mixture was left stirring for 2 h. Then aq. NH$_3$ (4.5 ml) was added and the mixture was stirred for 16 h. After removing the solvents to dryness, the residue was redissolved in water, filtered and purified by MPLC, followed by HPLC purification. The desired triphosphate (37) (10.2 µmol, 4%, $\epsilon_{280}$=10000) was isolated as a colourless foam. MPLC conditions: a gradient was run from 0.05M TEAB to 0.7 M TEAB using 2 l of each on a DEAE sephadex column. The product containing fractions came off with ~0.4 M TEAB. After removing the solvent, the product was HPLC purified. HPLC conditions: t$_r$(t-riphosphate): 21.9 min (Zorbax C-18 preparative column, buffer A 0.1 M TEAB, buffer B 0.1 M TEAB+30% Acetonitrile, gradient 5-35% buffer B in 35 min). $^1$H NMR (D$_2$O) δ 2.17-2.23 (m, 1H, H-2'), 2.40-2.45 (m, 1H, H-2'), 3.67 (s, 2H, CH$_2$N), 3.99 (d, J=5.9 Hz, 2H, OCH$_2$), 4.02-4.17 (m, 2H, H-5'), 4.25 (br s, 1H, H-4'), 4.32-4.33 (m, 1H, H-3'), 5.13 (d, J=10.3 Hz, 1H, =CH$_2$), 5.23 (d, J=17.2 Hz, 1H, =CH$_2$), 5.78-5.88 (m. 1H, =CH), 6.16 (t, J=6.7 Hz, 1H, H-1'), 8.33 (s, 1H, H-6). $^{31}$P NMR (161.9 MHz, D$_2$O) δ −21.3 (t, J=19.5 Hz, 1P, P$_\gamma$), −10.3 (d, J=19 Hz, 1P, P$_\alpha$), −7.1 (d, J=15.5 Hz, 1P, P$_\beta$). Mass (−ve electrospray) calcd for C$_{15}$H$_{22}$N$_3$O$_{14}$P$_3$ 561.03. found 560, 480 [M-phosphate], 401 [M-2× phosphate].

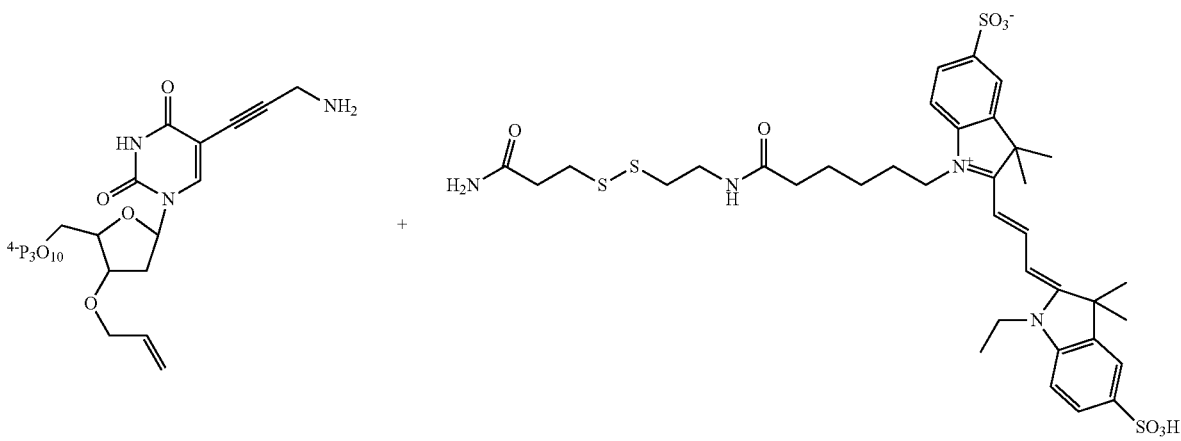

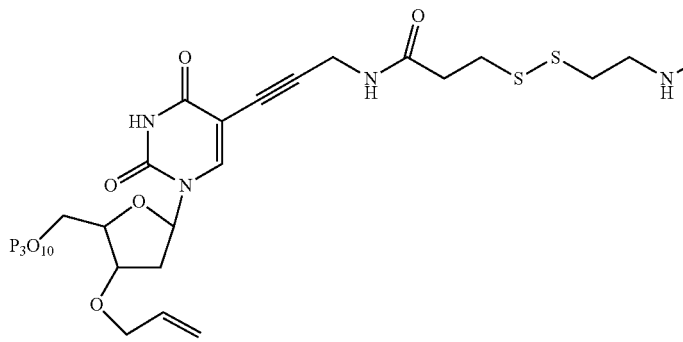
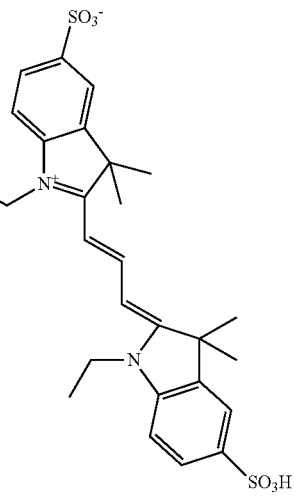

(38)

To a solution of Cy3 disulfide linker (2.5 μmol) in DMF (0.2 ml) at 0° C. was added. Disuccinimidyl carbonate (0.96 mg 3.75 gmol) and 4-(dimethylamino) pyridine (DMAP) (0.46 mg 3.75 gmol). The reaction mixture was stirred for 10 min and then checked by TLC (MeOH:DCM 3:7) (activated ester $r_f$=0.5). In a separate flask the 3'-O-allyl thymidine triphosphate (37) (532 μl, 14.1 mM in water, 7.5 gmol) were mixed with Bu$_3$N (143 μl) and evaporated to dryness. After this the triphosphate (37) was dissolved in dry DMF (0.2 ml). To the triphosphate (37) solution at 0° C. was added the activated dye and the reaction mixture was allowed to warm to room temperature and then stirred for 16 h. The solvent was removed and the residue was dissolved in water. The reaction mixture was passed through a small DEAE sephadex column (2×5 cm) using 0.1 M TEAB (100 ml) to remove the coupling reagents and unreacted linker. With 1 M TEAB (100 ml) the triphosphate (38) was eluted. The mixture was then separated by HPLC. Yield: 1.41 gmol (56%, $\epsilon_{550}$=150000) product as a dark red solid were isolated. HPLC conditions: t$_r$ (38): 19.6 min (Zorbax C-18 preparative column, buffer A 0.1 M TEAB, buffer B Acetonitrile, gradient: 2-58% buffer B in 29 min). $^1$H (d$_6$ DMSO) δ 0.75-0.79 (m, 3H, CH$_3$), 1.17-1.28 (m, 2H, CH$_2$), 1.48-1.55 (m, 2H, CH$_2$), 1.64 (s, 12H, 4×CH$_3$), 1.70-1.77 (m, 2H, CH$_2$), 1.96-2.02 (m, 1H, H-2'), 2.07-2.11 (m, 2H, CH$_2$), 2.25-2.30 (m, 1H, H-2'), 2.51-2.55 (m, 2H, CH$_2$), 2.64-2.68 (m, 2H, CH$_2$), 2.75-2.81 (m, 2H, CH$_2$), 3.27-3.31 (m, 2H, CH$_2$), 3.91-4.05 (m, 9H, H-5', OCH$_2$, NCH$_2$, 2×NCH$_2$-dye), 4.13 (s, 1H, H-4'), 4.22-4.24 (m, 1H, H-3'), 5.06 (d, J=10.5 Hz, 1H, =CH$_2$), 5.15 (dd, J=1.4 Hz, 17.3 Hz, 1H, =CH$_2$), 5.72-5.82 (m, 1H, =CH), 6.03-6.06 (m, 1H, H-1'), 6.20-6.29 (m, 2H, αH), 7.23-7.31 (m, 2H, H$_{Ar}$), 7.63-7.79 (m, 5H, H-6, 4×H$_{Ar}$), 8.31-8.45 (m, 1H, βH). $^{31}$P (161.9 MHz, d$_6$ DMSO) δ −20.2 (m, 1P, P$_β$), −10.0 (d, J=18.5 Hz, 1P, P$_α$), −4.8 (d, J=19.5 Hz, 1P, P$_γ$). Mass (−ve electrospray) calcd for C$_{51}$H$_{67}$S$_4$N$_6$O$_{22}$P$_3$ 1336.24. found 1335.1, 688.1 [cleaved disulfide (dye), 647.9 [cleaved disulfide (nucleotide)].

Enzyme Incorporation of Compound 38

Figure 7:
FIG. 7 shows the effective blocking by compound 38 (a 3'-0allyl nucleotide of the invention).

To a 100 nM DNA primer/template (primer previously labelled with P32 and T4 polynucleotide kinase) in Tris-HCl pH 8.8 50 mM, Tween-20 0.01%, and MgSO$_4$ 4 mM, add 2 μM compound 38 and 100 nM polymerase (*Thermococcus sp. 9°N exo $^-$Y409V A485L* supplied by New England Biolabs). The template consists of a run of 10 adenine bases to show the effect of the block. The reaction is heated to 65 C for 10 mins. To show complete blocking, a chase is performed with the four native, unblocked nucleoside triphosphates. Quantitative incorporation of the allyl block can be observed (see FIG. 7) and this can be seen to act as an effective block to further incorporation.

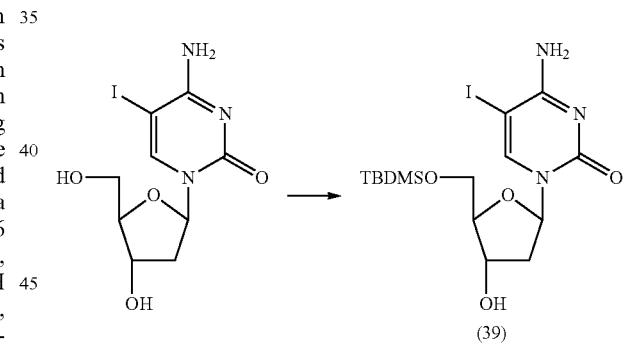

(39)

5'-O-(tert-Butyldimethylsilyl)-5-iodo-2'-deoxycytidine (39)

To a solution of 5-iodo-2'-deoxycytidine (2.2 g, 6.23 mmol) in DMF (130 ml) was added imidazole (467 mg, 6.85 mmol). The mixture was cooled at 0° C. and tert-butyldimethylsilyl chloride (TBDMSCl) (1.33 g, 6.85 mmol) added over 5 minutes. After 18 h at room temperature, the volatiles were evaporated under reduced pressure and the residue purified by flash chromatography on silica gel with EtOAc:MeOH (95:5 to 90:10) to give the expected product (39) (2.10 g, 72%) together with unreacted starting material (490 mg) $^1$H NMR (d$_6$ DMSO) δ 0.11 (s, 3H, CH$_3$), 0.12 (s, 3H, CH$_3$), 0.89 (s, 9H, 3CH$_3$), 1.90 (ddd, J=13.2, 7.7 and 5.7 Hz, 1H, 2.18 (ddd, J=13.2, 5.7 and 2.3 Hz, 1H, HH-2'), 3.72 (dd, J=11.5, 3.6 Hz, 1H, HH-5'), 3.80 (dd, J=11.5, 2.8 Hz, 1H, HH-5'), 3.86-3.89 (m, 1H, H-4'), 4.14-4.18 (m, 1H, H-3'), 5.22 (1H, d, J=4.1 Hz, OH), 6.09 (1H, dd, J=7.8, 5.8 Hz, H-1'), 6.60 (br s, 1H, NHH), 7.81 (br s, 1H, NHH), 7.94 (s, 1H, H-6); MS (ES): m/z (%) (M+H) 468 (90%).

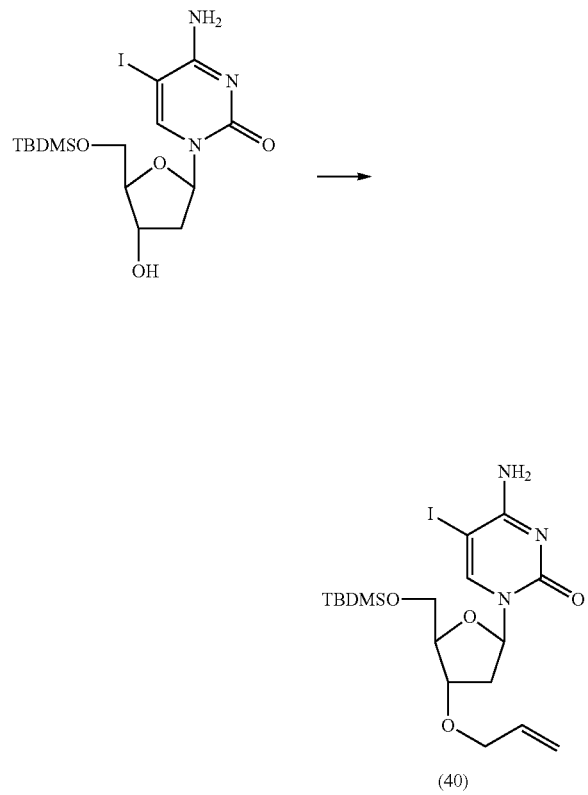

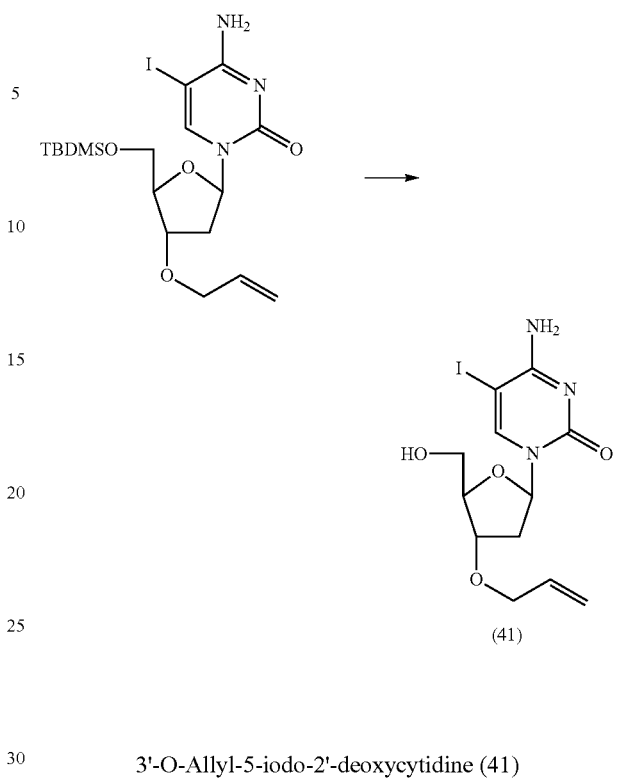

3'-O-Allyl-5'-O-(tert-butyldimethylsilyl)-5-iodo-2'-deoxycytidine (40)

To a solution of NaH (60%, 113 mg, 2.84 mmol) in THF (26 ml) under N₂ atmosphere, was slowly added a solution of the starting nucleoside (39) (669 mg, 1.43 mmol) in THF (6 ml). The mixture was stirred at room temperature for 45 minutes, cooled at 0° C. and allyl bromide (134 µL, 1.58 mmol) was slowly added. After 15 h at room temperature, the solution was cooled to 0° C. and quenched by addition of H₂O (5 ml). THF evaporated under reduced pressure and the product extracted into EtOAc (3×25 ml). Combined organic extracts were dried (MgSO₄) filtered and the volatiles evaporated under reduced pressure to give a residue that was purified by flash chromatography on silica gel with EtOAc affording the expected 3'-O-allyl product (40) (323 mg, 44%) as a colourless oil, together with some unreacted starting material (170 mg); ¹H NMR (d₆ DMSO) 0.00 (s, 3H, CH₃), 0.01 (s, 3H, CH₃), 0.79 (s, 9H, 3CH₃), 1.84 (ddd, J=13.3, 8.2 and 5.5 Hz, 1H, H-2'), 2.20-2.25 (m, 1H, H-2'), 3.62-3.72 (m, 2H, H-5'), 3.88-3.93 (m, 4H, H-3',4', HHC═CH═), 5.1 (dd, J=8.5, 1.7 Hz, 1H, CH═CHH), 5.16 (dd, J=17.2, 1.7 Hz, 1H, CH═CHH), 5.75-5.83 (m, 1H, CH═CHH), 5.94 (dd, J=8.4, 5.6 Hz, 1H, H-1'), 6.53 (br s, 1H, NHH), 7.74 (br s, 1H, NHH), 7.83 (s, 1H, H-6); MS (ES): m/z (%) (M−H) 506 (100%).

3'-O-Allyl-5-iodo-2'-deoxycytidine (41)

To a solution of the starting nucleoside (40) (323 mg, 0.64 mmol) in THF (15 ml) under N₂ protected atmosphere was added at room temperature tetrabutylammonium fluoride (TBAF) 1M in THF (0.7 ml, 0.7 mmol). Mixture stirred for one hour and then quenched by addition of H₂O (5 ml). THF was evaporated and aqueous residue extracted into EtOAc (3×25 ml). Combined organic extracts were dried (MgSO₄), filtered and the volatiles evaporated under reduced pressure giving a crude material which was purified by flash chromatography on a pre-packed silica column eluted with EtOAc. The product (41) was obtained as a white solid (233 mg, 93%). ¹H NMR (d₆ DMSO) δ 1.96-2.05 (m, 1H, H-2') 2.24 (ddd, J=13.5, 5.8 and 2.8 Hz, 1H, H-2'), 3.50-3.62 (m, 2H, H5'), 3.91-3.97 (m, 2H, H3', H4'), 4.03-4.07 (m, 2H, HHC—CH═), 5.11-5.16 (m, 2H, OH, CH═CHH), 5.24 (dd, J=17.2, 1.6 Hz, 1H, CH═CHH), 5.82-5.91 (m, 1H, CH═CHH), 6.02 (dd, J=7.6, 6.0 Hz, 1H, H-1'), 6.60 (s, 1H, NHH), 7.79 (s, 1H, NHH), 8.21 (s, 1H, H-6). MS (ES): m/z (%) (M−H) 392 (100%).

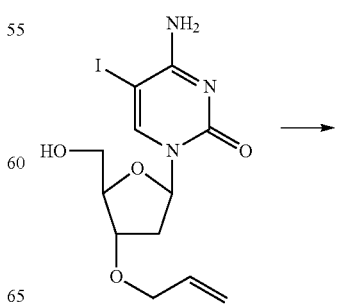

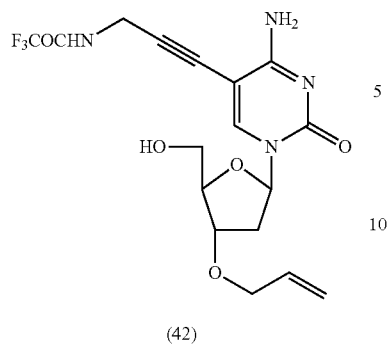

(42)

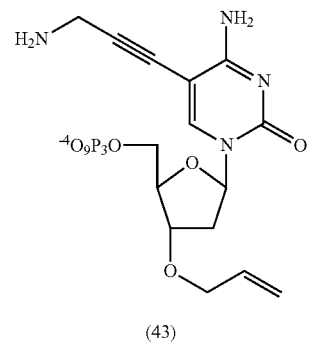

(43)

3'-O-Allyl-5-[3-(2,2,2-trifluoroacetamide)-prop-1-ynyl]-2'-deoxycytidine (42)

To a solution of the starting nucleoside (41) (200 mg, 0.51 mmol) in dry DMF (8.5 ml) at room temperature and Argon atmosphere, was slowly added CuI (19 mg, 0.10 mmol), NEt$_3$ (148 µl, 1.02 mmol), prop-2-ynyl-acetamide (230 mg, 1.53 mmol) and Pd(PPh$_3$)$_4$ (58 mg, 0.05 mmol). The mixture was stirred at room temperature and protected from light during four hours, quenched by addition of dowex bicarbonate and stirred for a 1 h, then filtered and the volatiles evaporated under reduced pressure. The residue was further evaporated from MeOH (15 ml) and then purified by flash chromatography on silica gel (CH$_2$Cl$_2$, CH$_2$Cl$_2$:EtOAc 1:1, EtOAc:MeOH 97.5:2.5). The expected product (42) was obtained as a beige solid (180 mg, 85%). $^1$H NMR (d$_6$ DMSO) δ 1.90 (ddd, J=13.6, 7.7 and 6.0 Hz, 1H, H-2'), 2.16 (ddd, J=13.6, 5.7 and 2.4 Hz, 1H, H-2'), 3.42-3.50 (m, 2H, H-5'), 3.84-3.87 (m, 3H, H-4', OHHC—CH=), 3.94-3.96 (m, 1H, H-3'), 4.16 (d, J=5.1 Hz, 2H, H$_2$C—N), 4.98-5.05 (m, 2H, OH, CH=CHH), 5.14 (dd, J=17.3, 1.7 Hz, 1H, CH=CHH), 5.72-5.82 (m, 1H, CH=CHH), 5.95 (dd, J=7.7, 5.8 Hz, 1H, H-1'), 6.74 (br s, 1H, NHH), 7.72 (br s, 1H, NHH), 8.01 (1H, s, H-6), 9.82 (br t, 1H, HN—CH$_2$). MS (ES): m/z (%) (M–H) 415 (100%).

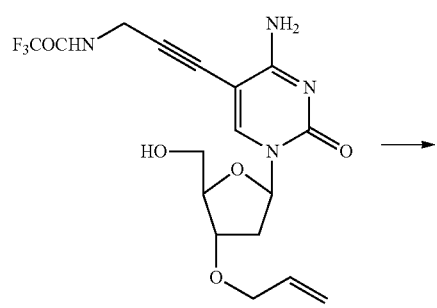

3'-O-Allyl-5-(3-amino-prop-1-ynyl)-5'-O-triphosphate-2'-deoxycytidine (43)

To a solution of the nucleoside (42) (170 mg, 0.41 mmol) and proton sponge (105 mg, 0.50 mmol) (both previously dried under P$_2$O$_5$ for at least 24 h) in PO(OMe)$_3$ (360 µl), at 0° C. under Argon atmosphere, was slowly added POCl$_3$ (freshly distilled) (50 µl, 0.54 mmol). The solution was vigorously stirred for 3 h at 0° C. and then quenched by addition of tetra-tributylammonium diphosphate 0.5 M in DMF (3.20 ml, 1.60 mmol), followed by nBu$_3$N (0.75 ml, 3.2 mmol) and triethylammonium bicarbonate (TEAB) 0.1 M (12 ml). The mixture was stirred at room temperature for 3 h and then an aqueous ammonia solution (ρ 0.88 1.0 ml) (12 ml) was added. The solution was stirred at room temperature for 15 h, volatiles evaporated under reduced pressure and the residue was purified by MPLC with a gradient of TEAB from 0.05M to 0.7M. The expected triphosphate (43) was eluted from the column at approx. 0.51 M TEAB. A second purification was done by HPLC in a Zorbax SB-C18 column (21.2 mm i.d.×25 cm) eluted with 0.1M TEAB (pump A) and 30% CH$_3$CN in 0.1M TEAB (pump B) using a gradient as follows: 0-5 min 5% B, Φ.2 ml; 5-25 min 80% B, Φ.8 ml; 25-27 min 95% B, Φ.8 ml; 27-30 min 95% B, Φ.8 ml; 30-32 min 5% B, Φ.8 ml; 32-35 min 95% B, Φ.2 ml, affording the product (43) detailed above with a t$_r$(43): 20.5 (20 µmols, 5% yield); $^{31}$P NMR (D$_2$O) δ –6.01 (d, J=19.9 Hz, 1P, P$_\gamma$), –10.24 (d, J=19.3 Hz, 1P, P$_\alpha$), –21.00 (t, J=19.6 Hz, 1P, P$_\beta$); $^1$H NMR (D$_2$O) δ 2.19-2.26 (m, 1H, H-2'), 2.51 (1H, ddd, J=14.2, 6.1 and 3.2 Hz, H-2'), 3.96-4.07 (m, 4H, NCH$_2$, OHHC—CH=), 4.09-4.14 (m, 1H, 1H, H-5') 4.22-4.26 (m, 1H, H-5'), 4.30-4.37 (m, 2H, H-3', 4'), 5.20 (d, J=10.4 Hz, 1H, CH=CHH), 5.30 (1H, dd, J=17.3, 1.5 Hz, CH=CHH), 5.85-5.95 (m, 1H, CH=CHH), 6.18 (t, J=6.5 Hz, 1H, H-1'), 8.40 (s, 1H, H-6); MS (ES): m/z (%) (M–H) 559 (100%).

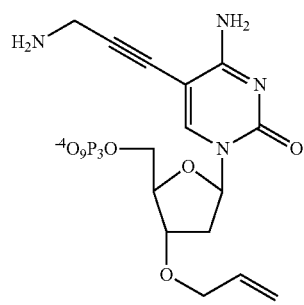
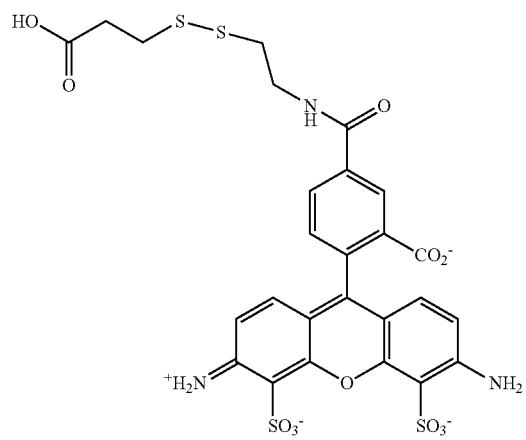
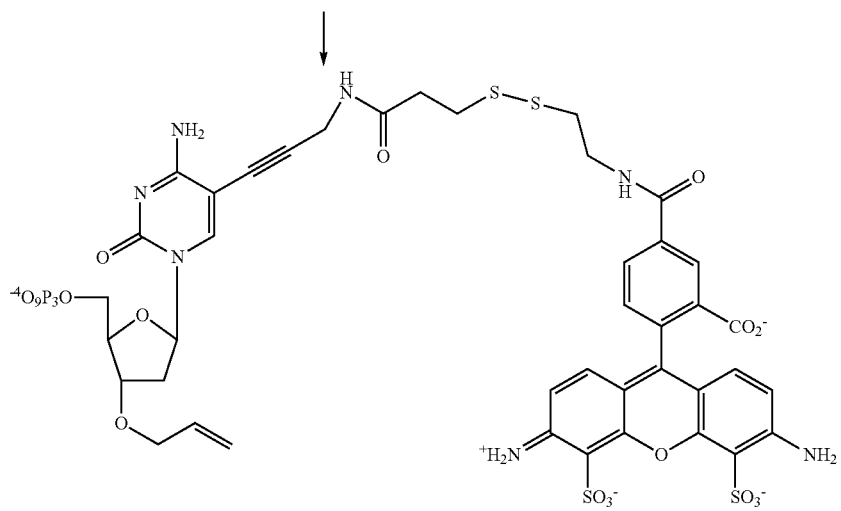

(44)

To a solution of Alexa Fluor 488 disulfide linker (2.37 mg, 3.4 μmol) in DMF (500 μl) was added N,N-disuccinimidyl carbonate (1.3 mg, 5.1 μmol) and 4-DMAP (0.6 mg, 5.1 μmol). The mixture was stirred for 10 minutes, then it was added into the solution of the nucleotide (43) (3.23 mg, 5.8 μmol) in DMF (100 μl) containing nBu$_3$N (30 μl). The mixture was continuously stirred for 16 h at room temperature. The volatiles were evaporated under reduced pressure and the residue was firstly purified by passing it through a short ion exchange resin Sephadex-DEAE A-25 (40-120μ)-column, first eluted with TEAB 0.1 M (70 ml) then 1.0 M TEAB (100 ml). The latest containing the expected product (44) was concentrated and the residue was HPLC purified in a Zorbax SB-C18 column (21.2 mm i.d.×25 cm) eluted with 0.1M TEAB (pump A) and CH$_3$CN (pump B) using a gradient as follows: 0-2 min 2% B, Φ.2 ml; 2-4 min 2% B, Φ.8 ml; 4-15 min 23% B, Φ.8 ml; 15-24 min 23% B, Φ.8 ml; 24-26 min 95% B, Φ.8 ml; 26-28 min 95% B, Φ.8 ml, 28-30 min 2% B, Φ.8 ml, 30-33 min 2% B, Φ.2 ml affording the product detailed above with a r$_t$(44): 19.9 (0.56 μmols, 17% yield based on UV measurement); $\lambda_{max}$=493 nm, $\in$ 71,000 cm$^{-1}$ M$^{-1}$ in H$_2$O); $^{31}$P NMR (D$_2$O) δ −5.07 (d, J=22.2 Hz, 1P, P$_\chi$), −10.26 (d, J=19.4 Hz, 1P, P$_\alpha$), −21.09 (t, J=19.7 Hz, 1P, P$_\beta$); $^1$H NMR (D$_2$O) δ 2.44-2.26 (m, 2H, HH-2'), 2.50 (t, J=6.7 Hz, 2H, CH$_2$), 2.83 (4H, CH$_2$, CH$_2$), 3.58 (t, J=6.0 Hz, 2H, CH$_2$), 4.07-3.91 (m, 6H, HH-5', NCH$_2$, OHHC—CH=), 4.16-4.12 (m, 1H, H-4'), 4.23-4.17 (m, 1H, H-3'), 5.24-5.09 (m, 2H, CH=CHH, CH=CHH), 5.84-5.74 (m, 1H, CH=CHH), 5.98 (t, J=8.1 Hz, 1H, H-1'), 6.79 (d, J=9.1 Hz, 1H, H$_{Ar}$), 6.80 (d, J=9.3 Hz, 1H, H$_{Ar}$), 7.06 (t, J=8.8 Hz, 2H, H$_{Ar}$), 7.55 (br s, 1H, H$_{Ar}$), 7.90-7.85 (m, 2H, H$_{Ar}$), 7.94 (s, 1H, H-6); MS (ES): m/z (%) (M−H)$^-$ 1239 (27%).

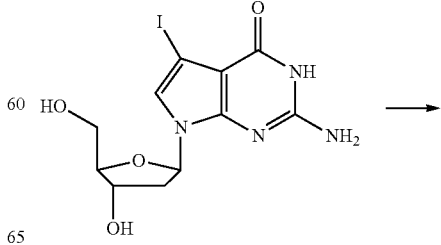

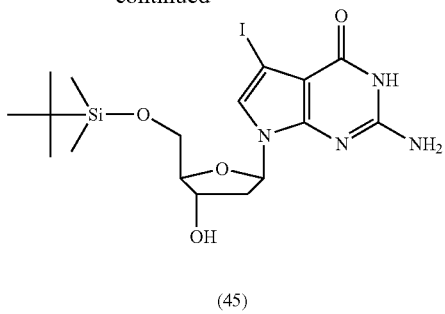

5'-O-(tert-Butyldimethylsilyl)-7-deaza-7-iodo-2'-deoxyguanosine (45)

A solution of (44) (0.55 g, 1.4 mmol) in DMF (10 ml) was treated with imidazole (190 mg, 2.8 mmol) and TBDMSCl (274 mg, 1.82 mmol) at r.t. for 15 h. The reaction was quenched with MeOH (~5 ml). The mixture was evaporated to dryness. Water (~300 ml) was added to the residue and stirred for at least 1 h to fully dissolve imidazole. Filtration gave a brown solid, which was dried and purified by silica gel chromatography (DCM to DCM:MeOH 90:10), giving (45) as pale yellow powder (394 mg, 56%). $^1$H NMR (d$_6$ DMSO) δ 0.00, 0.01 (2s, 6H, CH$_3$), 0.82 (s, 9H, CH$_3$), 1.99-2.05, 2.16-2.22 (2m, 2H, H-2'), 3.58-3.66 (m, 2H, H-5'), 3.72-3.74 (m, 1H, H-4'), 4.18-4.19 (m, 1H, H-3'), 5.16 (d, J=3.0 Hz, 1H, OH), 6.20 (dd, J=6.0, 8.0 Hz, 1H, H-1'), 6.25 (br s, 2H, NH$_2$), 7.58 (s, 1H, H-8), 10.37 (s, 1H, HN). Mass (–ve electrospray) calcd for C$_{17}$H$_{27}$IN$_4$O$_4$Si 506. found 505.

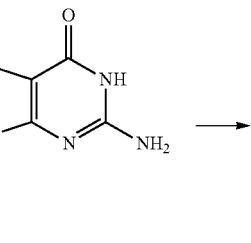

(46)

3'-O-Allyl-5'-O-(tert-butyldimethylsilyl)-7-deaza-7-iodo-2'-deoxyguanosine (46)

A solution of (45) (354 mg, 0.7 mmol) in THF (25 ml) was treated with NaH (42 mg, 1.75 mmol) at r.t. for 1 h. Allyl bromide was added and the suspension was stirred at r.t. for 2 days. ~60% of the starting material (45) was converted to the product (46). The reaction was quenched with sat. aq. NaCl and extracted with DCM three times. The combined organic layer were dried (MgSO$_4$) and concentrated under vacuum. The residue was treated with TBAF in THF (1 ml) and THF (1 ml) for 30 min. Evaporation to remove of THF. The residue was dissolved in DCM and aqueous NaHCO$_3$ (sat.) was added. The aqueous layer was extracted with DCM three times. The combined organics was dried over MgSO$_4$ and concentrated under vacuum. Purification by chromatography on silica (EtOAc to EtOAc:MeOH 85:15) gave (46) as a yellow foam (101 mg, 35%). $^1$H NMR (d$_6$ DMSO) δ 2.15-2.31 (m, 2H, H-2'), 3.41-3.45 (m, 2H, H-5'), 3.82-3.85 (m, 1H, H-4'), 3.93 (d, J=2.6 Hz, 2H, OCH$_2$), 4.04-4.06 (m, 1H, H-3'), 4.99 (t, J=5.4 Hz, OH), 5.08-5.24 (m, 2H, =CH$_2$), 5.79-5.89 (m, 1H, CH=), 6.15 (dd, J=5.9, 9.1 Hz, 1H, H-1'), 6.27 (br s, 2H, NH$_2$), 7.07 (s, H-8), 10.39 (s, 1H, NH). Mass (–ve electrospray) calcd for C$_{14}$H$_{17}$IN$_4$O$_4$ 432. found 431.

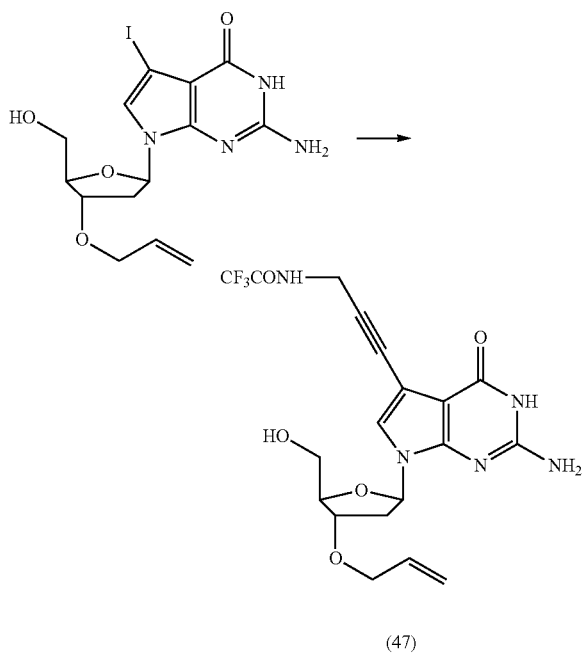

(47)

3'-O-Allyl-5'-O-(tert-butyldimethylsilyl)-7-deaza-7-[3-(2,2,2-trifluoroacetamido)-prop-1-ynyl]-2'-deoxyguanosine (47)

Under N$_2$, a suspension of (46) (104 mg, 0.24 mmol), Pd(PPh$_3$)$_4$ (24 mg, 0.024 mmol), CuI (9.1 mg, 0.048 mmol), Et$_3$N (66 μL, 0.48 mmol) and CH≡CCH$_2$NHCOCF$_3$ (89 μL, 0.72 mmol) in DMF (2 ml) was stirred at r.t. for 15 h. The reaction was protected from light with aluminium foil. After TLC indicating the full consumption of starting material, the reaction mixture was concentrated. The residue was diluted with MeOH (20 ml) and treated with dowex-HCO$_3$$^-$. The mixture was stirring for 30 min and filtered. The solution was concentrated and purified by silica gel chromatography (petroleum ether:EtOAc 50:50 to petroleum ether:EtOAc:MeOH 40:40:20) giving (47) as a yellow powder (74 mg, 70%). $^1$H NMR (d$_6$ DMSO) δ 2.15-2.39 (m, 2H, H-2'), 3.42-3.44 (m, 2H, H-5'), 3.83-3.87 (m, 1H, H-4'), 3.93-3.95 (m, 2H, OCH$_2$), 4.0-4.07 (m, 1H, H-3'), 4.15 (d, J=5.3 Hz, 2H, ≡CCH$_2$), 4.91 (t, J=5.4 Hz, OH), 5.08-5.24 (m, 2H, =CH$_2$), 5.80-5.89 (m, 1H, CH=), 6.15 (dd, J=5.6, 8.9 Hz, 1H, H-1'), 6.28 (br s, 2H, NH$_2$), 7.24 (s, H-8), 9.98 (t, J=5.3 Hz, 1H, NH), 10.44 (s, 1H, NH). Mass (−ve electrospray) calcd for C$_{19}$H$_{20}$F$_3$N$_5$O$_5$ 455. found 454.

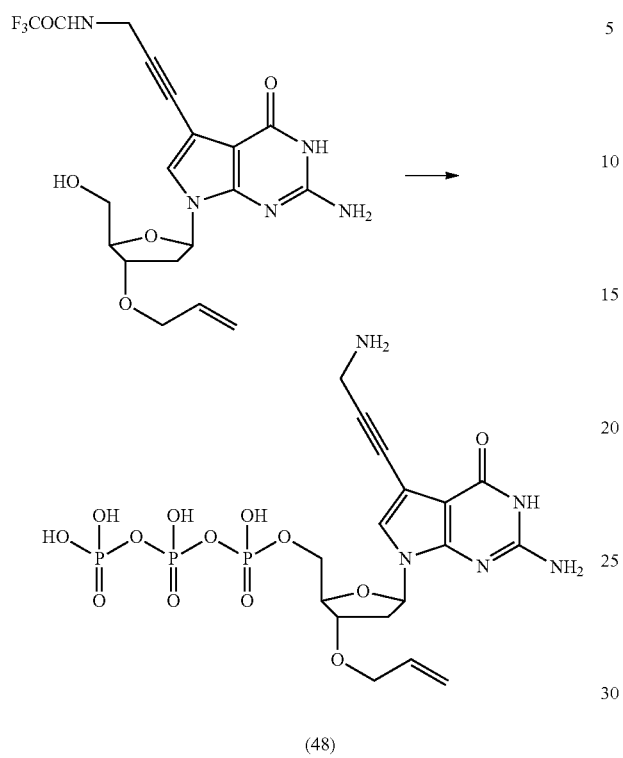

(48)

The nucleoside (47) and proton sponge was dried over P$_2$O$_5$ under vacuum overnight. A solution of (47) (73 mg, 0.16 mmol) and proton sponge (69 mg, 0.32 mmol) trimethylphosphate (0.5 ml) was stirred with 4 Å molecular sieves for 1 h. Freshly distilled POCl$_3$ (18 μl, 0.19 mmol) was added and the solution was stirred at 4° C. for 2 h. The mixture was slowly warmed up to room temperature and bis(tri-n-butyl ammonium) pyrophosphate (1.3 ml, 0.88 mmol) and anhydrous tri-n-butyl amine (0.3 ml, 1.28 mmol) was added. After 5 min, the reaction was quenched with 0.1 M TEAB (triethylammonium bicarbonate) buffer (10 ml) and stirred for 3 h. The water was removed under reduced pressure and the resulting residue dissolved in concentrated ammonia (ρ 0.88, 10 ml) and stirred at room temperature for 16 h. The reaction mixture was then evaporated to dryness. The residue was dissolved in water and the solution applied to a DEAE-Sephadex A-25 column. MPLC was performed with a linear gradient of 2 L each of 0.05 M and 1 M TEAB. The triphosphate was eluted between 0.7 M and 0.8 M buffer. Fractions containing the product were combined and evaporated to dryness. The residue was dissolved in water and further purified by HPLC. t$_r$(48)=20.3 min (Zorbax C18 preparative column, gradient: 5% to 35% B in 30 min, buffer A 0.1 M TEAB, buffer B MeCN). The product (48) was isolated as a white foam (147 O.D., 19.3 mmol, 12%, ε$_{260}$=7,600). $^1$H NMR (D$_2$O) δ 2.38-2.46 (m, 2H, H-2'), 3.91 (m, 2H, ≡CCH$_2$), 3.98-4.07 (m, 4H, H-5', 2H, OCH$_2$), 4.25 (br s, 1H, H-4'), 4.40 (br s, 1H, H-3'), 5.16-5.30 (m, 1H, =CH$_2$), 5.83-5.91 (m, 1H, =CH), 6.23-6.27 (m, 1H, H-1'), 7.44 (s, 1H, H-8). $^{31}$P NMR δ −7.1 (d, J=16.5 Hz, 1P, P$_\gamma$), −10.1 (d, J=19.9 Hz, 1P, P$_\alpha$), −21.5 (t, J=18.0 Hz, 1P, P$_\beta$). Mass (−ve electrospray) calcd for C$_{17}$H$_{24}$N$_5$O$_{13}$P$_3$ 599. found 598.

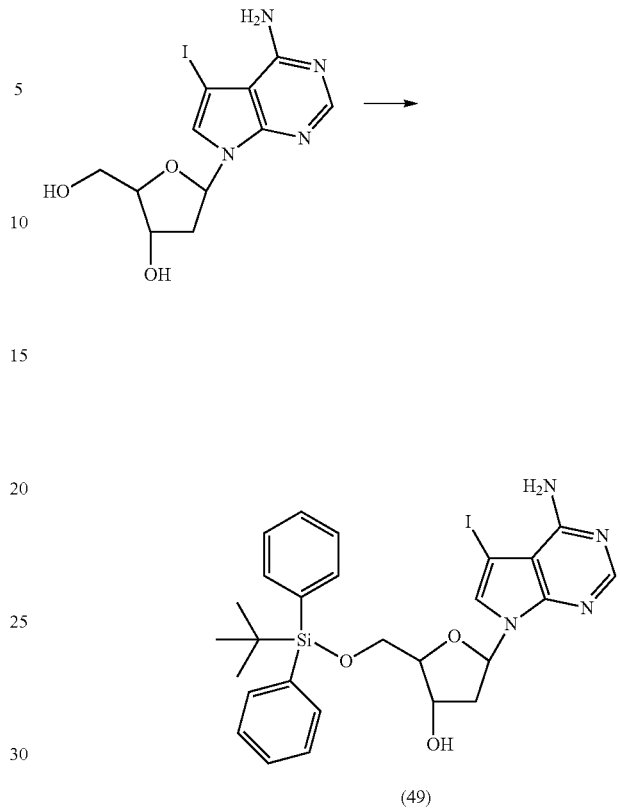

(49)

7-Deaza-5'-O-diphenylsilyl-7-iodo-2'-deoxyadenosine (49)

TBDPSCl (0.87 g, 2.78 mmol) was added to a stirred solution of 7-deaza-7-iodo-2'-deoxyadenosine (1.05 g, 2.78 mmol) in dry pyridine (19 ml) at 5° C. under N$_2$. After 10 min the solution was allowed to rise to room temperature and stirred for 18 h. The solution was evaporated under reduced pressure and the residue purified by flash chromatography on silica (DCM to DCM:MeOH 19:1). This gave the desired product (49) (1.6 g, 83%). $^1$H NMR (d$_6$ DMSO) δ 1.07 (s, 9H), 2.31-2.36 (m, 1H), 3.76-3.80 (dd, 1H, J=11.1, 4.7 Hz), 3.88-3.92 (dd, 1H, J=11.2, 3.9 Hz), 3.97-4.00 (m, 1H), 4.49-4.50 (m, 1H), 5.83 (s, 1H), 6.58-6.61 (t, 1H, J=6.7 Hz), 7.44-7.55 (m, 6H), 7.68-7.70 (m, 5H), 8.28 (s, 1H). Mass (electrospray) calcd for C$_{27}$H$_{31}$IN$_4$O$_3$Si 614.12. found 613.

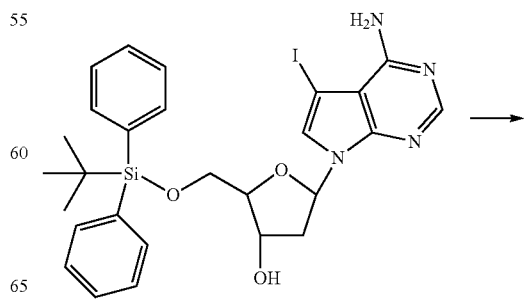

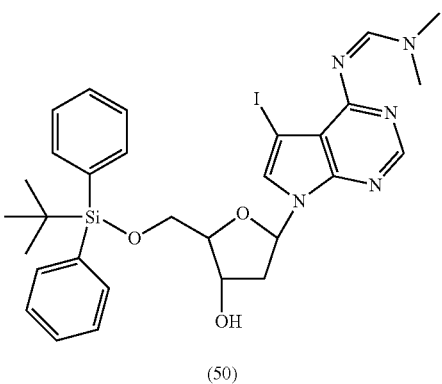

(50)

7-Deaza-6-N,N-dimethylformadine-5'-O-diphenylsi-lyl-7-Iodo-2'-deoxyadenosine (50)

A solution of (49) (1.6 g, 2.61 mmol) in MeOH (70 ml) containing dimethylformamide dimethylacetal (6.3 g, 53 mmol) was heated at 45° C. for 18 h. The solution was cooled, evaporated under reduced pressure and purified by flash chromatography on silica gel (EtOAc to EtOAc:MeOH 98:2). This resulted in 1.52 g (87%) of the desired product (50). $^1$H NMR (d$_6$ DMSO) δ 0.85 (s, 9H), 2.05-2.11 (m, 1H), 3.03 (s, 3H), 3.06 (s, 3H), 3.53-3.57 (dd, 1H, J=11.1, 4.8 Hz), 3.65-3.69 (dd, 1H, J=11.1, 4 Hz), 3.73-3.76 (q, 1H, J=4 Hz), 4.26-4.28 (m, 1H), 5.21-5.22 (d, 1H, J=4.3 Hz), 6.39-6.42 (t, 1H, J=6.8 Hz), 7.21-7.32 (m, 6H), 7.46 (s, 1H), 7.45-7.48 (m, 4H), 8.15 (s, 1H), 8.68 (s, 1H). Mass (+ve electrospray) calcd for C$_{30}$H$_{36}$IN$_5$O$_3$Si 669.16. found 670.

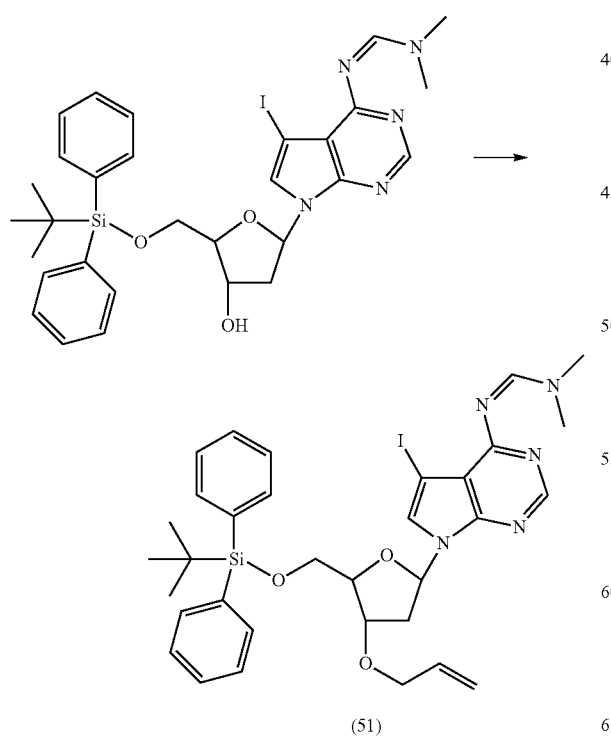

(51)

3'-O-Allyl-7-deaza-6-N,N-dimethylformadine-5'-O-diphenylsilyl-7-iodo-2'-deoxyadenosine (51)

A solution of (50) (1.52 g, 2.28 mmol) in dry THF (5 ml) was added drop wise at room temperature to a stirred suspension of sodium hydride (60%, 109 mg, 2.73 mmol) in dry THF (35 ml). After 45 min the yellow solution was cooled to 5° C. and allyl bromide (0.413 g, 3.41 mmol) added. The solution was allowed to rise to room temperature and stirred for 18 h. After adding isopropanol (10 drops) the solution was partitioned between water (5 ml) and EtOAc (50 ml). The organic layer was separated and the aqueous solution extracted further with EtOAc (2×50 ml). The combined organic solutions were dried (MgSO$_4$) and evaporated under reduced pressure. The residue was purified by flash chromatography on silica (petroleum ether:EtOAc 1:3 to EtOAc) to give 1.2 g (74%) of the desired product (51) as a gum. $^1$H NMR (d$_6$ DMSO) δ 1.03 (s, 9H), 2.39-2.45 (m, 1H), 2.60-2.67 (m, 1H), 3.2 (s, 3H), 3.23 (s, 3H), 3.70-3.74 (dd, 1H, J=11.2, 4.6 Hz), 3.83-3.87 (dd, 1H, J=11, 5.4 Hz), 4.03-4.08 (m, 3H), 4.30-4.31 (m, 1H), 5.18-5.21 (m, 1H), 5.28-5.33 (m, 1H), 5.89-5.98 (m, 1H), 6.49-6.53 (dd, 1H, J=8.4, 5.8 Hz), 7.41-7.51 (m, 6H), 7.62-7.66 (m, 5H), 8.31 (s, 1H), 8.85 (s, 1H). Mass (+ve electrospray) calcd for C$_{33}$H$_{40}$IN$_5$O$_3$Si 709.19. found 710.

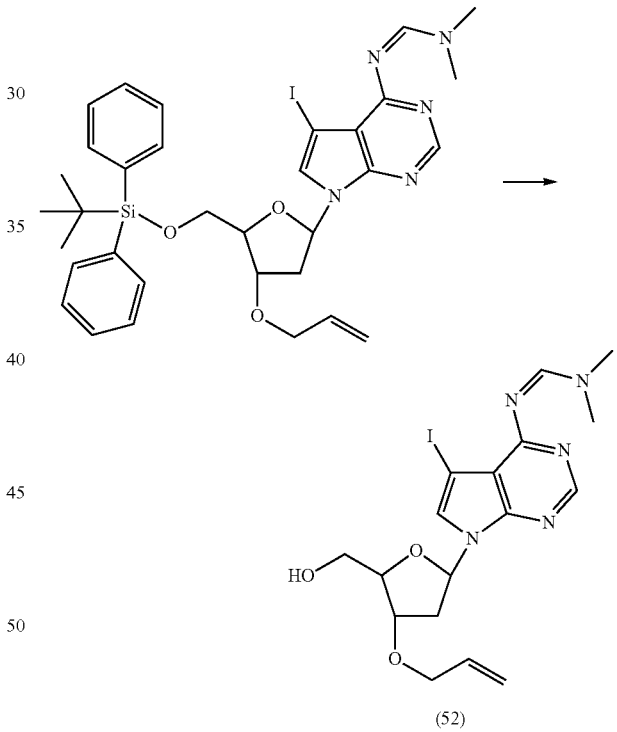

(52)

3'-O-Allyl-7-deaza-6-N,N-dimethylformadine-7-iodo-2'-deoxyadenosine (52)

A 1M solution of TBAF in THF (4.4 ml, 4.4 mmol) was added to a solution of (51) (1.2 g, 1.69 mmol) in THF (100 ml) at 5° C. under N$_2$. The solution was allowed to rise to room temperature and stirred for 2d. The solution was evaporated under reduced pressure and purified by flash chromatography on silica (EtOAc to EtOAc:MeOH 97:3). This gave 593 mg (77%) of the desired product (52). $^1$H NMR (d$_6$ DMSO) δ 2.54 (m, 2H), 3.40 (s, 3H), 3.44 (s, 3H), 3.72-3.8 (m, 2H), 4.18-4.21 (m, 1H), 4.23-4.27 (m, 3H), 4.4-4.42 (d, 1H, J=5.7 Hz), 5.35-5.41 (m, 2H), 5.49-5.5 (q, 1H, J=1.7 Hz), 5.53-5.55 (q, 1H, J=1.7 Hz), 6.1-6.2 (m, 1H), 6.67-6.70 (dd, 1H, J=8.8, 5.5 Hz), 7.96 (s, 1H), 8.53 (s, 1H), 9.06 (s, 1H). Mass (+ve electrospray) calcd for $C_{17}H_{22}IN_5O_3$ 471.08. found 472.

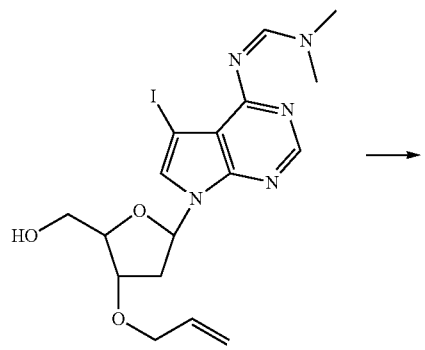

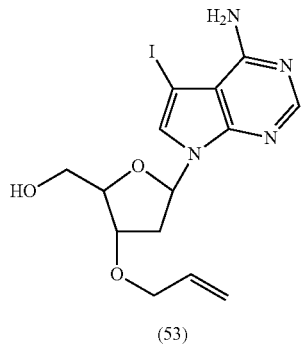

(53)

3'-O-Allyl-7-deaza-7-iodo-2'-deoxyadenosine (53)

A solution of (52) (593 mg, 1.3 mmol) in MeOH (20 ml) containing 35% aqueous ammonia (20 ml) was heated at 50° C. for 2d. After cooling the solution was evaporated under reduced pressure and then azeotroped with toluene (3×10 ml). This resulted in 530 mg (98%) of the desired product (53) as a solid. $^1$H NMR ($d_6$ DMSO) δ 2.39 (m, 1H), 3.56-3.65 (m, 2H), 4.03-4.05 (m, 1H), 4.09-4.11 (m, 2H), 5.23-5.25 (d, 1H, J=10.6 Hz), 5.35-5.4 (d, 1H, J=15.4 Hz), 5.95-6.05 (m, 1H), 6.48-6.51 (dd, 1H, J=8.9, 5.5 Hz), 6.6-6.95 (s, 1H), 7.75 (s, 1H), 8.16 (s, 1H). Mass (+ve electrospray) calcd for $C_{14}H_{17}IN_4O_3$ 416.03. found 417.

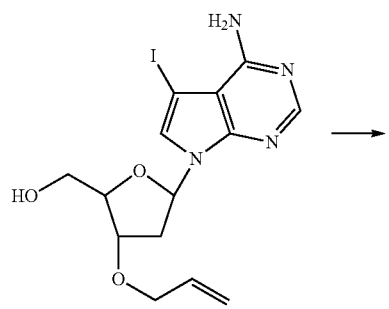

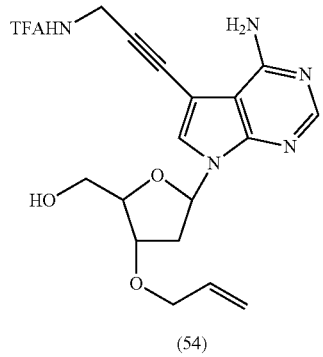

(54)

3'-O-Allyl-7-deaza-7-[3-(2,2,2-trifluoroacetamide)]-7 2'-deoxyadenosine (54)

To a solution of (53) (494 mg, 1.19 mmol) in dry DMF (17 ml) was added sequentially copper (I) iodide (45.1 mg, 0.24 mmol), N-2,2,2-trifluoro-N-prop-2-ynylacetamide (538 mg, 3.56 mmol), $Et_3N$ (240 mg, 2.38 mmol) and $Pd(Ph_3P)_4$ (137 mg, 0.12 mmol) at room temperature. The flask was wrapped in foil to exclude light and stirred under $N_2$ for 18 h. Then MeOH (10 ml) and a small spatula of dowex bicarbonate form were added and the mixture stirred for 30 min. The mixture was filtered, evaporated under reduced pressure and the residue triturated with MeOH to remove palladium salts. The filtrate was evaporated under reduced pressure and purified by flash chromatography on silica (DCM to DCM:MeOH 97:3). The desired product (54) was obtained as brown solid (490 mg, 94%). $^1$H NMR ($d_6$ DMSO) δ 2.25-2.31 (m, 1H), 2.98-3.04 (m, 1H), 3.41-3.49 (m, 2H), 3.88-3.95 (m, 3H), 4.10-4.12 (d, 1H, J=5.2 Hz), 4.22-4.23 (d, 2H, J=5.3 Hz), 5.07-5.12 (m, 2H), 5.19-5.24 (dd, 1H, J=17.3, 1.9 Hz), 5.79-5.89 (m, 1H), 6.31-6.35 (dd, 1H, J=8.6, 5.6 Hz), 7.69 (s, 1H), 8.02 (S, 1H). Mass (−ve electrospray) calcd for $C_{19}H_{20}F_3N_5O_4$ 439.15. found 438.

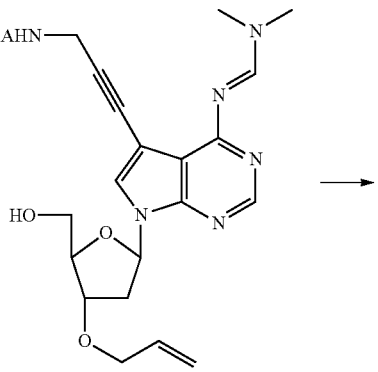

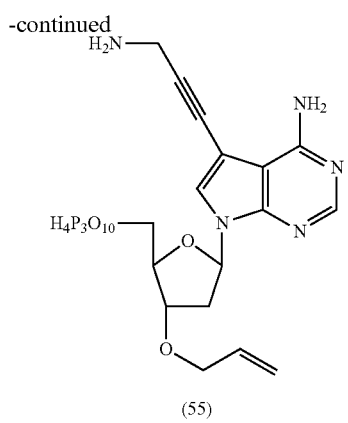

(55)

3'-O-Allyl-7-[3-aminoprop-1-ynyl]-7-deaza-2'-deoxyadenosine 5'-O-nucleoside triphosphate (55)

The nucleoside (54) and proton sponge was dried over $P_2O_5$ under vacuum overnight. A solution of (54) (84 mg, 0.191 mmol) and proton sponge (49 mg, 0.382 mmol) in trimethylphosphate (600 μl) was stirred with 4 Å molecular sieves for 1 h. Freshly distilled $POCl_3$ (36 μl, 0.388 mmol) was added and the solution was stirred at 4° C. for 2 h. The mixture was slowly warmed up to room temperature and bis(tri-n-butyl ammonium) pyrophosphate 0.5 M in solution in DMF (1.52 ml, 0.764 mmol) and anhydrous tri-n-butyl amine (364 μl, 1.52 mmol) was added. After 5 min, the reaction was quenched with 0.1 M TEAB (triethylammonium bicarbonate) buffer (5 ml) and stirred for 3 h. The water was removed under reduced pressure and the resulting residue dissolved in concentrated ammonia (ρ 0.88, 5 ml) and stirred at room temperature for 16 h. The reaction mixture was then evaporated to dryness. The residue was dissolved in water and the solution applied to a DEAE-Sephadex A-25 column. MPLC was performed with a linear gradient of 0.05 M to 1 M TEAB. Fractions containing the product were combined and evaporated to dryness. The residue was dissolved in water and further purified by HPLC. HPLC: $t_r$(55) 22.60 min (Zorbax C18 preparative column, gradient: 5% to 35% B in 20 min, buffer A 0.1M TEAB, buffer B MeCN) The product was isolated as a white foam (17.5 μmol, 5.9%, $\epsilon_{280}$=15000). $^1$H NMR ($D_2O$) δ 2.67-2.84 (2m, 2H, H-2'), 4.14 (br s, 2H, $CH_2NH$), 4.17-4.36 (m, 2H, H-5'), 4.52 (br s, 1H, H-4'), 6.73 (t, J=6.6 Hz, 1H, H-1'), 8.06 (s, 1H, H-8), 8.19 (s, 1H, H-2). $^{31}$P NMR ($D_2O$) δ -5.07 (d, J=21.8 Hz, 1P, $P_\gamma$), -10.19 (d, J=19.8 Hz, 1P, $P_\alpha$), -21.32 (t, J=19.8 Hz, 1P, $P_\beta$). Mass (-ve electrospray) calcd for $C_{15}H_{21}N_8O_{12}P_3$ 598.05. found 596.

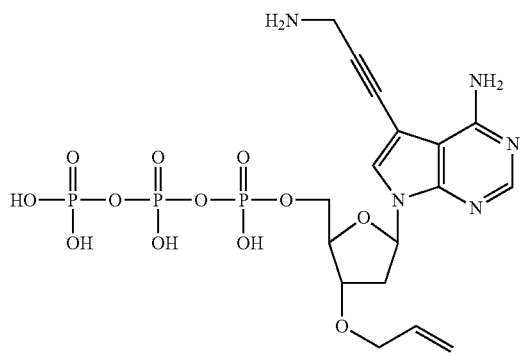

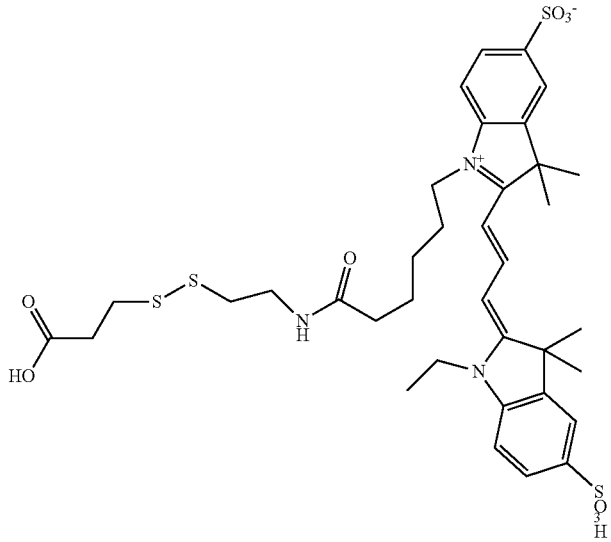

-continued

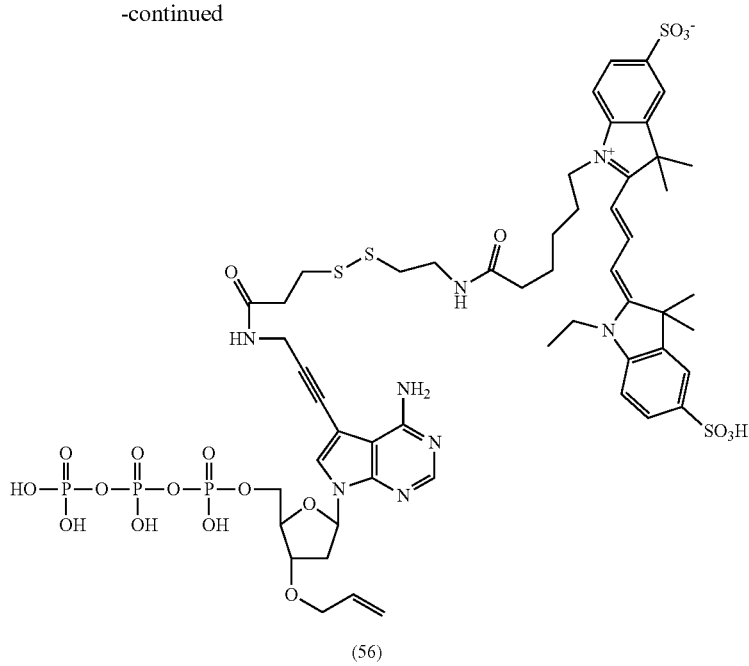

(56)

To the Cy3 disulphide linker (2.6 μmol) in solution in DMF (450 μl) is added at 0° C. 100 μl of a mixture of 1-(3-dimethylaminopropyl)-3-ethylcarbodiimide hydrochloride, 1-hydroxybenzotriazole hydrate and N-methylmorpholine (26 μM each) in DMF. The reaction mixture was stirred at room temperature for 1 h. The reaction was monitored by TLC (MeOH:CH$_2$Cl$_2$ 4:6) until all the dye linker was consumed. Then 400 μl of DMF are added at 0° C., followed by the nucleotide (55) (3.9 μmol), in solution in water (100 μl) and the reaction mixture and stirred at room temperature overnight. TLC (MeOH:CH$_2$Cl$_2$ 4:6) showed complete consumption of the activated ester and a dark red spot appeared on the baseline. The reaction was quenched with TEAB buffer (0.1M, 10 ml) and loaded on a DEAE Sephadex column (2×5 cm). The column was first eluted with 0.1 M TEAB buffer (100 ml) to wash off organic residues and then 1 M TEAB buffer (100 ml). The desired triphosphate (56) was eluted out with 1 M TEAB buffer. The fraction containing the product were combined, evaporated and purified by HPLC. HPLC conditions: t$_r$(56)=: 21.38 min (Zorbax C18 preparative column, gradient: 5% to 15% B in 1 min, then 4 min at 15% B, then 15 to 35% B in 15 min, buffer A 0.1M TEAB, buffer B MeCN). The product was isolated as dark pink solid (0.15 μmol, 12.5%, ε$_{550}$=15000). $^1$H NMR (D$_2$O) δ 2.03 (t, J=6.4 Hz, 2H, CH$_2$), 2.21-2.33 (m, 1H, H-2'), 2.37-2.49 (m, 1H, H-2'), 2.50 (t, J=6.3 Hz, 2H, CH$_2$), 2.66 (t, J=5.4 Hz, 2H, CH$_2$), 3.79 (t, J=6.4 Hz, 2H CH$_2$), 3.99 (m, 4H, CH$_2$N, H-5'), 4.18 (br s, 1H, H-4'), 6.02, 6.17 (2d, J=13:6 Hz, 2H, H$_{ar}$) 6.30 (dd, J=6.1, 8.6 Hz, H-1'), 7.08, 7.22 (2d, J=7.8, 8.6 Hz, 2H, 2×=CH), 7.58-7.82 (m, 6H, 2H$_{Ar}$, H-2, H-8), 8.29 (t, J=13.6 Hz, =CH). $^{31}$P NMR (D$_2$O) δ −4.83 (m, 1P, P$_γ$), −10.06 (m, 1P, P$_α$), −20.72 (m, 1P, P$_β$).

Cleavage of 3'-Allyl Group in Aqueous Conditions

The following shows a typical deblocking procedure for a 3'blocked nucleoside in which approximately 0.5 equivalents of Na$_2$PdCl$_4$ and 4 equivalents of the water-soluble phosphine ligand L were employed, in water, at 50° C. Tfa stands for trifluoracetyl:

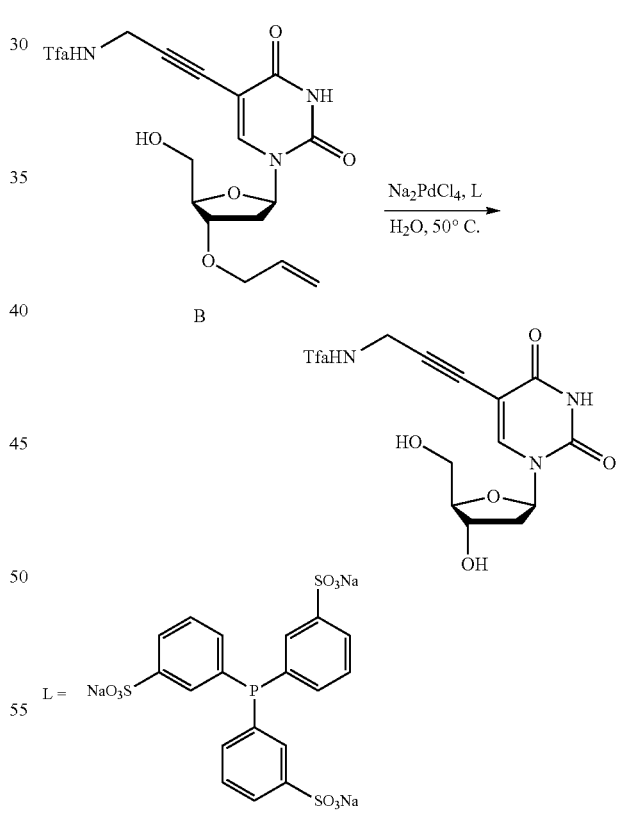

To a solution of Ligand L (7.8 mg, 13.7 μmol) in degassed H$_2$O (225 μl) was added a solution of Na$_2$PdCl$_4$ (0.5 mg, 1.6 μmol) in degassed H$_2$O (25 μl) in an eppendorff vial. The two solutions were mixed well and after 5 min a solution of B (1 mg, 2.3 μmol) in H$_2$O (250 μl) was added. The reaction mixture was then placed in a heating block at 50° C. The reaction could be followed by HPLC. Aliquots of 50 μl were taken from the reaction mixture and filtered through an eppendorff filter vial (porosity 0.2 μm); 22 μl of the solution were injected in the HPLC to monitor the reaction. The reaction was purified by HPLC. In a typical experiment the cleavage was finished (i.e. >98% cleavage had occurred after 30 min).

3'-OH Protected with a 3,4 Dimethoxybenzyloxymethyl Group as a Protected Form of a Hemiacetal:

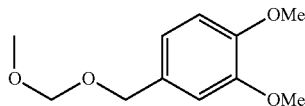

Nucleotides bearing this blocking group have similar properties to the allyl example, though incorporate less rapidly. Deblocking can be achieved efficiently by the use of aqueous buffered cerium ammonium nitrate or DDQ, both conditions initially liberating the hemiacetal (1) which decomposes to the required (2) prior to further extension:

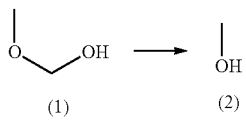

The 3'-OH may also be protected with benzyl groups where the phenyl group is unsubstituted, e.g. with benzyloxymethyl, as well as benzyl groups where the phenyl group bears electron-donating substituents; an example of such an electron-rich benzylic protecting group is 3,4-dimethoxybenzyloxymethyl.

In contrast, electron-poor benzylic protecting groups, such as those in which the phenyl ring is substituted with one or more nitro groups, are less preferred since the conditions required to form the intermediate groups of formulae —C(R')$_2$—OH, —C(R')$_2$—NH$_2$, and —C(R')$_2$—SH are sufficiently harsh that the integrity of the polynucleotide can be affected by the conditions needed to deprotect such electron-poor benzylic protecting groups.

3'-OH Protected with a Fluoromethyloxymethyl Group as a Protected Form of a Hemiacetal:

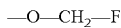

Nucleotides bearing this blocking group may be converted to the intermediate hemiacetal using catalytic reactions known to those skilled in the art such as, for example, those using heavy metal ions such as silver.

The invention claimed is:

1. A method of controlling the incorporation of a nucleotide having a ribose or deoxyribose sugar moiety, and said nucleotide is complementary to a second nucleotide in a target single-stranded polynucleotide in a synthesis or sequencing reaction, comprising incorporating into the growing complementary polynucleotide said nucleotide, the incorporation of said nucleotide preventing or blocking introduction of subsequent nucleoside or nucleotide molecules into said growing complementary polynucleotide and said nucleotide comprises a detectable label linked by a linker; and reacting the nucleotide with a water-soluble phosphine to cleave the linker.

2. The method of claim 1, wherein said detectable label is a fluorophore.

3. The method of claim 1, wherein said linker contains a disulfide linkage.

4. The method of claim 1, wherein said linker is a phosphine-cleavable azide-containing linker.

5. The method of claim 1, wherein said water-soluble phosphine also cleaves said protecting group.

6. The method of claim 5, further comprising repeating said incorporating and reacting steps one or more times, thereby incorporating multiple nucleotides into the growing complementary polynucleotide.

7. The method of claim 1, wherein said incorporating comprises contacting the growing complementary polynucleotide with a polymerase.

8. The method of claim 1, wherein said protecting group is attached to the 3' oxygen atom of the ribose or deoxyribose sugar moiety of said nucleotide.

9. The method of claim 1, wherein said protecting group is attached to the 2' oxygen atom of the ribose or deoxyribose sugar moiety of said nucleotide.

10. A method of controlling the incorporation of a nucleotide having a ribose or deoxyribose sugar moiety, and said nucleotide is complementary to a second nucleotide in a target single-stranded polynucleotide in a synthesis or sequencing reaction, comprising incorporating said nucleotide into the growing complementary polynucleotide with a polymerase, the incorporation of said nucleotide preventing or blocking introduction of subsequent nucleoside or nucleotide molecules into said growing complementary polynucleotide; wherein a protecting group is attached to the 3' oxygen atom of the ribose or deoxyribose sugar moiety of said nucleotide; and said nucleotide comprises a detectable label linked by a linker; and reacting the nucleotide with a water-soluble phosphine to cleave the linker.

11. The method of claim 10, wherein said detectable label is a fluorophore.

12. The method of claim 10, wherein said linker contains a disulfide linkage.

13. The method of claim 10, wherein said linker is a phosphine-cleavable azide-containing linker.

14. The method of claim 10, wherein said water-soluble phosphine also cleaves said protecting group.

15. The method of claim 14, further comprising repeating said incorporating and reacting steps one or more times, thereby incorporating multiple nucleotides into the growing complementary polynucleotide.

* * * * *